US010052304B2

(12) United States Patent
Allen et al.

(10) Patent No.: US 10,052,304 B2
(45) Date of Patent: Aug. 21, 2018

(54) COMPOSITIONS AND METHODS FOR CANCER THERAPY

(71) Applicant: UNIVERSITY OF IOWA RESEARCH FOUNDATION, Iowa City, IA (US)

(72) Inventors: Bryan G. Allen, Iowa City, IA (US); Douglas R. Spitz, Iowa City, IA (US); Garry R. Buettner, Iowa City, IA (US); Joseph Cullen, Iowa City, IA (US); Joshua Schoenfeld, Iowa City, IA (US); Michael Schultz, Iowa City, IA (US); Fenghuang Zhan, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 30 days.

(21) Appl. No.: 15/291,833

(22) Filed: Oct. 12, 2016

(65) Prior Publication Data

US 2017/0100370 A1  Apr. 13, 2017

Related U.S. Application Data

(60) Provisional application No. 62/240,372, filed on Oct. 12, 2015.

(51) Int. Cl.
| | |
|---|---|
| *A61N 5/10* | (2006.01) |
| *A61K 31/282* | (2006.01) |
| *A61K 31/337* | (2006.01) |
| *A61K 31/375* | (2006.01) |
| *A61K 31/7068* | (2006.01) |
| *A61K 45/06* | (2006.01) |
| *A61K 9/00* | (2006.01) |
| *A61K 31/295* | (2006.01) |
| *A61K 31/704* | (2006.01) |
| *A61K 31/198* | (2006.01) |
| *A61K 31/555* | (2006.01) |
| *A61K 47/22* | (2006.01) |

(52) U.S. Cl.
CPC .......... *A61K 31/375* (2013.01); *A61K 9/0019* (2013.01); *A61K 31/198* (2013.01); *A61K 31/282* (2013.01); *A61K 31/295* (2013.01); *A61K 31/337* (2013.01); *A61K 31/555* (2013.01); *A61K 31/704* (2013.01); *A61K 31/7068* (2013.01); *A61K 45/06* (2013.01); *A61N 5/10* (2013.01); *A61K 47/22* (2013.01); *A61N 2005/1098* (2013.01)

(58) Field of Classification Search
None
See application file for complete search history.

(56) References Cited

U.S. PATENT DOCUMENTS

| | | |
|---|---|---|
| 5,639,787 A | 6/1997 | Riordan et al. |
| 8,003,634 B2 | 8/2011 | Adams et al. |
| 8,703,755 B2 | 4/2014 | Adams et al. |
| 2011/0086110 A1* | 4/2011 | Adams ................ C07D 211/60 424/649 |

OTHER PUBLICATIONS

Olney, Free Radic Res. Mar. 2013 ; 47(3): 154-1633 (Year: 2013).*
Sundstrom, J Clin Oncol 22:801-810, 2004. (Year: 2004).*
Ahmad, et al., "2-Deoxyglucose combined with wild-type p53 overexpression enhances cytotoxicity in human prostate cancer cells via oxidative stress", Free Radic Biol Med 44, 826-834 (2008).
Ahmad, et al., "Mitochondrial O2*- and H2O2 mediate glucose deprivation-induced stress in human cancer cells", J Biol Chem 280, 4254-4263 (2005).
Aykin-Burns, et al., "Increased levels of superoxide and H2O2 mediate the differential susceptibility of cancer cells versus normal cells to glucose deprivation", Biochem J, 418(1), 29-37 (2009).
Baader, et al., "Ascorbic-acid-mediated iron release from cellular ferritin and its relation to the formation of DNA strand breaks in neuroblastoma cells", J Cancer Res Clin Oncol 120(7), 415-421 (1994).
Birch-Machin, et al., "An evaluation of the measurement of the activities of complexes I-IV in the respiratory chain of human skeletal muscle mitochondria", Biochem Med Metab Biol 51(1), 35-42 (1994).
Bize, et al., "Superoxide Dismutase and Superoxide Radical in Morris Hepatomas", Cancer Res 40(10), 3686-3693 (1980).
Boyer, et al., "Reductive release of ferritin iron: a kinetic assay", Anal Biochem 174(1), 17-22 (1988).
Boyer, et al., "Superoxide ion as a primary reductant in ascorbate-mediated ferritin iron release", Free Radic Biol Med 3, 389-395 (1987).
Buettner, "Ascorbate autoxidation in the presence of iron and copper chelates", Free Radic Res Commun 1, 349-353 (1986).
Buettner, et al., "Catalytic metals, ascorbate and free radicals: combinations to avoid", Radiat Res 145, 532-541 (1996).
Buettner, "In the absence of catalytic metals ascorbate does not autoxidize at pH 7: ascorbate as a test for catalytic metals", J Biochem Biophys Methods 16, 27-40 (1988).
Caltagirone, et al., "Modulation of cellular iron metabolism by hydrogen peroxide. Effects of H2O2 on the expression and function of iron-responsive element-containing mRNAs in B6 fibroblasts".
Cameron, et al., "Ascorbic Acid, Cell Proliferation, and Cancer", The Lancet 299(7749), 542 (1972).
Cameron, et al., "Supplemental ascorbate in the supportive treatment of cancer: Prolongation of survival times in terminal human cancer", Proc Natl Acad Sci 73(10), 3685-3689 (1976).
Cameron, et al., "Supplemental ascorbate in the supportive treatment of cancer: reevaluation of prolongation of survival times in terminal human cancer", Proc Natl Acad Sci 75(9), 4538-4542 (1978).

(Continued)

*Primary Examiner* — Layla D Berry
(74) *Attorney, Agent, or Firm* — Viksnins Harris Padys Malen LLP

(57) ABSTRACT

The invention provides compositions and methods to treat a hyperproliferative disorder with ascorbate or a pharmaceutically acceptable salt thereof, at least one chelating agent that enhances ascorbate redox cycling (EDTA) to form H$_2$O$_2$, and one or more anti-cancer therapies.

16 Claims, 39 Drawing Sheets

(56) References Cited

OTHER PUBLICATIONS

Case, et al., "Elevated mitochondrial superoxide disrupts normal T cell development, impairing adaptive immune responses to an influenza challenge", Free Radic Biol Med 50, 448-458 (2011).
Chen, et al., "Ascorbate in pharmacologic concentrations selectively generates ascorbate radical and hydrogen peroxide in extracellular fluid in vivo", Proc Natl Acad Sci 104, 8749-8754 (2007).
Chen, et al., "Pharmacologic ascorbic acid concentrations selectively kill cancer cells: Action as a pro-drug to deliver hydrogen peroxide to tissues", Proc Natl Acad Sci 102(38), 13604-13609 (2005).
Clement, et al., "The in vitro cytotoxicity of ascorbate depends on the culture medium used to perform the assay and involves hydrogen peroxide", Antioxid Redox Signal 3, 157-163 (2001).
Cramer-Morales, et al., "SOD2 targeted gene editing by CRISPR/Cas9 yields Human cells devoid of MnSOD", Free Radic Biol Med 89, 379-386 (2015).
Creagan, et al., "Failure of high-dose vitamin C (ascorbic acid) therapy to benefit patients with advanced cancer. A controlled trial", N Engl J Med 301, 687-690 (1979).
Dickinson, et al. "A palette of fluorescent probes with varying emission colors for imaging hydrogen peroxide signaling in living cells", J Am Chem Soc 132, 5906-5915 (2010).
Doskey, et al., "Moles of a Substance per Cell Is a Highly Informative Dosing Metric in Cell Culture", PLoS One 10, e0132572 (2015).
Du, et al., "Mechanisms of ascorbate-induced cytotoxicity in pancreatic cancer", Clin Cancer Res 16(2), 509-520 (2010).
Du, et al., "Role of labile iron in the toxicity of pharmacological ascorbate", Free Radic Biol Med 84, 289-295 (2015).
Eisenhauer, et al., "New response evaluation criteria in solid tumours: revised RECIST guideline (version 1.1)", Eur J Cancer Oxf Engl 45, 228-247 (2009).
Epsztejn, et al., "Fluorescence analysis of the labile iron pool of mammalian cells", Anal Biochem 248, 31-40 (1997).
Fath, et al., "Enhancement of carboplatin-mediated lung cancer cell killing by simultaneous disruption of glutathione and thioredoxin metabolism", Clin Cancer Res 17 (19), 6206-6217 (2011).
Halliwell, et al., "Role of free radicals and catalytic metal ions in human disease: an overview", Methods Enzymol 186, 1-85 (1990).
Ibrahim, et al., "Mitochondrial superoxide mediates labile iron level: evidence from Mn-SOD-transgenic mice and heterozygous knockout mice and isolated rat liver mitochondria", Free Radic Biol Med 65C, 143-149 (2013).
Kukulj, et al., "Altered iron metabolism, inflammation, transferrin receptors, and ferritin expression in non-small-cell lung cancer", Med Oncol 27(2), 268-277 (2010).
Levine, et al., "Vitamin C: A Concentration-Function Approach Yields Pharmacology and Therapeutic Discoveries1,2", Adv Nutr 2(2), 78-88 (2011).
Liu, et al., "A technique for serial collection of cerebrospinal fluid from the cisterna magna in mouse", J Vis Exp (21), 960 (2008).
Lowry, "Protein measurement with the Folin phenol reagent", J Biol Chem 193(1), 265-275 (1951).
Luo, et al., "Association between vitamin C intake and lung cancer: a dose-response meta-analysis", Sci Rep 4, 6161 (2014).
Ma, et al., "High-Dose Parenteral Ascorbate Enhanced Chemosensitivity of Ovarian Cancer and Reduced Toxicity of Chemotherapy", Science Translational Medicine 6 (222) 222ra18 (2014).
MacDonald, et al., "Response criteria for phase II studies of supratentorial malignant glioma", J Clin Oncol 8, 1277-1280 (1990).
McCarty, et al., "Increasing Superoxide Production and the Labile Iron Pool in Tumor Cells may Sensitize Them to Extracellular Ascorbate", Front Oncol 4, 249 (2014).
Ministry of Health Malaysia, "Vitamin C, EDTA & Ultraviolet in Cancer Treatment", Health Technology Assessment Section Medical Development Division Ministry of Health Malaysia 026/08, 13 pages (Feb. 2009).
Moertel, et al., "High-Dose Vitamin C versus Placebo in the Treatment of Patients with Advanced Cancer Who Have Had no Prior Chemotherapy—A Randomized Double-Blind Comparison", N Engl J Med 312, 137-141 (1985).
Mojic, et al., "Extracellular iron diminishes anticancer effects of vitamin C: an in vitro study", Sci Rep 4, 5955 (2014).
Monti, et al., "Phase I evaluation of intravenous ascorbic acid in combination with gemcitabine and erlotinib in patients with metastatic pancreatic cancer", PloS One 7, e29794 (2012).
Moser, et al., "Pharmacological ascorbate and ionizing radiation (IR) increase labile iron in pancreatic cancer", Redox Biol 2, 22-27 (2014).
Nath, et al., "alpha-Ketoacids scavenge H2O2 in vitro and in vivo and reduce menadione-induced DNA injury and cytotoxicity", Am J Physiol 268(1 Pt 1), C227-C236 (1995).
Oberley, et al., "Cell differentiation, aging and cancer: the possible roles of superoxide and superoxide dismutases", Med Hypotheses 6(3), 249-268 (1980).
Olney, et al., "Inhibitors of hydroperoxide metabolism enhance ascorbate-induced cytotoxicity", Free Radic Res 47 (3), 154-163 (2013).
Ornstein, "Disc Electrophoresis. I. Background and Theory", Ann N Y Acad Sci 121, 321-349 (1964).
Padayatty, et al., "Vitamin C pharmacokinetics: implications for oral and intravenous use", Ann Intern Med 140, 533-537 (2004).
Pantopoulos, et al., "Differences in the regulation of iron regulatory protein-1 (IRP-1) by extra- and intracellular oxidative stress", J Biol Chem 272, 9802-9808 (1997).
Parrow, et al., "Parenteral ascorbate as a cancer therapeutic: a reassessment based on pharmacokinetics", Antioxid Redox Signal 19(17), 2141-2156 (2013).
Riordan, et al., "Intravenous ascorbate as a tumor cytotoxic chemotherapeutic agent", Med Hypotheses 44, 207-213 (1995).
Sandler, et al., "Paclitaxel-carboplatin alone or with bevacizumab for non-small-cell lung cancer", N Engl J Med 355, 2542-2550 (2006).
Schiller, et al., "Comparison of four chemotherapy regimens for advanced non-small-cell lung cancer", N Engl J Med 346, 92-98 (2002).
Schoenfeld, et al., "Intracellular Redox Active Metal Ions Mediate the Differential Susceptibility of Lung and Brain Cancer Cells to Pharmacological Ascorbate", Society for Free Radical Biology and Medicine, 313, S131, Boston, MA (2014).
Schoenfeld, et al., "O2 and H2O2-Mediated Disruptions in Iron Metabolism Mediate the Selective Sensitization by Pharmacological Ascorbate to Chemotherapy and Radiation", Radiation Research Society, Poster, Waikoloa Village, HI (2016).
Schoenfeld, et al., "O2•- and H2O2-Mediated Disruption of Fe Metabolism Causes the Differential Susceptibility of NSCLC and GBM Cancer Cells to Pharmacological Ascorbate", Cancer Cell 31(4), 487-500 (2017).
Schoenfeld, et al., "Pharmacological Ascorbate in Combination with Standard-of-Care Radio-Chemotherapy Enhances Tumor Response in an Orthotopic Sarcoma Model", Society for Free Radical Biology and Medicine, 466, S193, San Francisco, CA (2016).
Schoenfeld, et al., "The Selective Toxicity of Pharmacological Ascorbate is Mediated by Alterations in Iron Metabolism", Free Radic Biol. Med, 150, S72-S73 (2015).
Simon, et al., "Accelerated titration designs for phase I clinical trials in oncology", J Natl Cancer Inst 89, 1138-1147 (1997).
Spitz, et al., "Glucose deprivation-induced oxidative stress in human tumor cells. A fundamental defect in metabolism?", Ann. N. Y. Acad. Sci., 899, 349-362 (2000).
Spitz, et al., "Hydrogen peroxide or heat shock induces resistance to hydrogen peroxide in Chinese hamster fibroblasts", J Cell Physiol 131, 364-373 (1987).
Spitz, et al., "Measurement of MnSOD and CuZnSOD activity in mammalian tissue homogenates", Current Protocols in Toxicology, Chapter 7, Unit 7.5 (2001).

(56) References Cited

OTHER PUBLICATIONS

Storer, "Design and Analysis of Phase I Clinical Trials", Biometrics 45(3), 925-937 (1989).

Stupp, et al., "Radiotherapy plus concomitant and adjuvant temozolomide for glioblastoma", N Engl J Med 352, 987-996 (2005).

Szatrowski, et al., "Production of large amounts of hydrogen peroxide by human tumor cells", Cancer Res 51, 794-798 (1991).

Torti, et al., "Iron and cancer: more ore to be mined", Nat Rev Cancer 13, 342-355 (2013).

Verrax, et al., "Pharmacologic concentrations of ascorbate are achieved by parenteral administration and exhibit antitumoral effects", Free Radic Biol Med 47, 32-40 (2009).

Vislisel, et al., "A simple and sensitive assay for ascorbate using a plate reader", Anal Biochem 365, 31-39 (2007).

Welsh, et al., "Pharmacological ascorbate with gemcitabine for the control of metastatic and node-positive pancreatic cancer (PACMAN): results from a phase I clinical trial", Cancer Chemother Pharmacol 71, 765-775 (2013).

Witmer, et al., "Direct spectrophotometric measurement of supraphysiological levels of ascorbate in plasma", Redox Biol 8, 298-304 (2016).

Yun, et al., "Vitamin C selectively kills KRAS and BRAF mutant colorectal cancer cells by targeting GAPDH", Science 350(6266), 1391-1396 (2015).

Zwacka, et al., "Redox gene therapy protects human IB-3 lung epithelial cells against ionizing radiation-induced apoptosis", Hum Gene Ther 9(9), 1381-1386 (1998).

\* cited by examiner

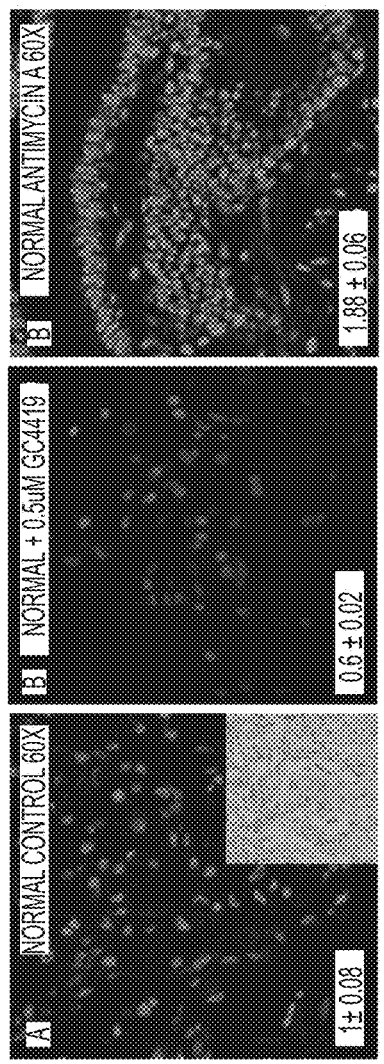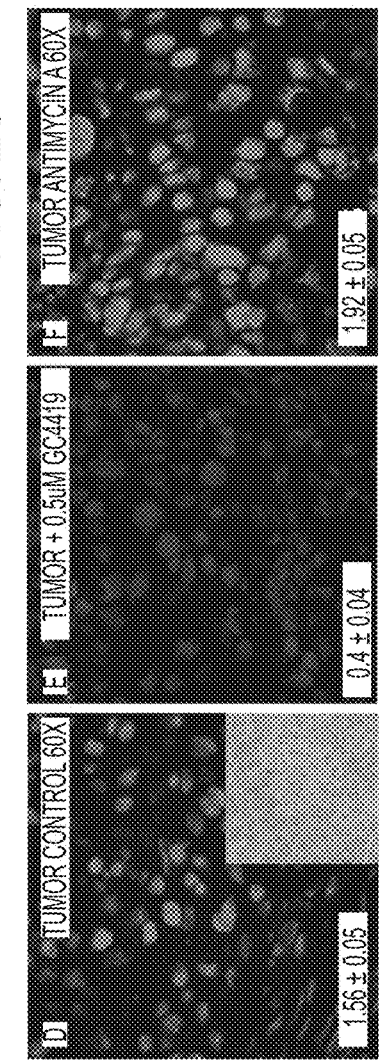

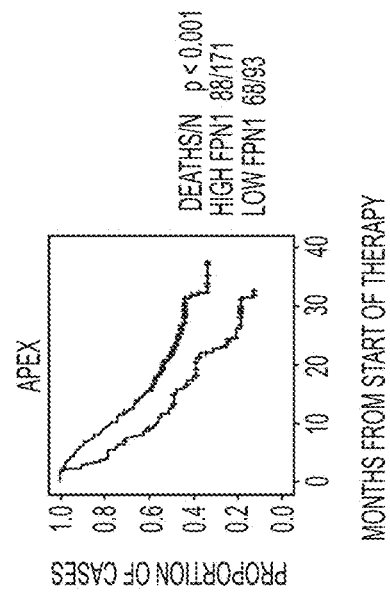
FIG. 9F
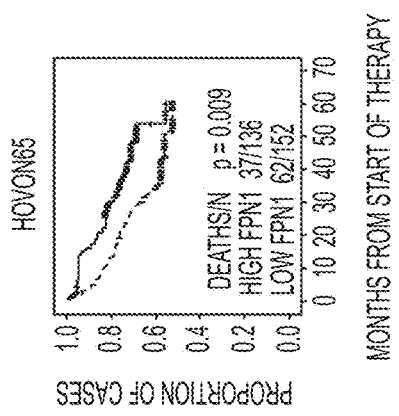
FIG. 9H
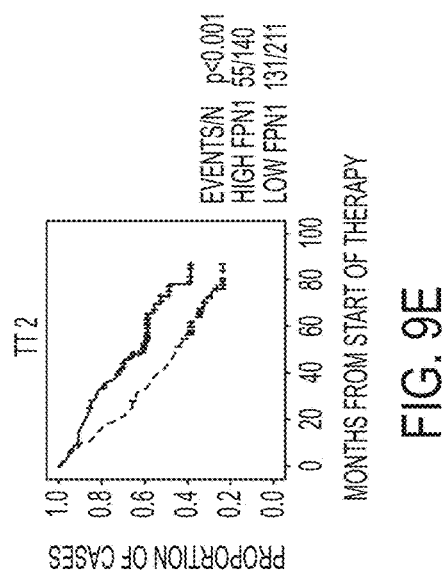
FIG. 9E
FIG. 9G

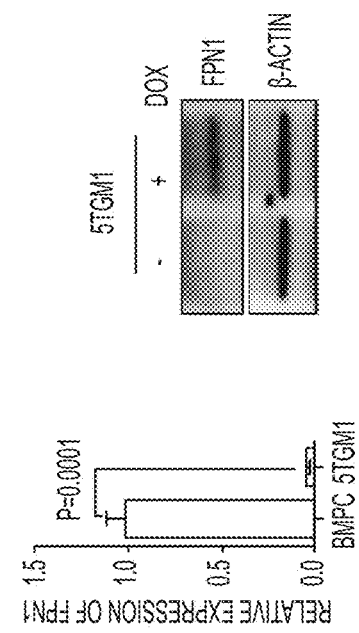
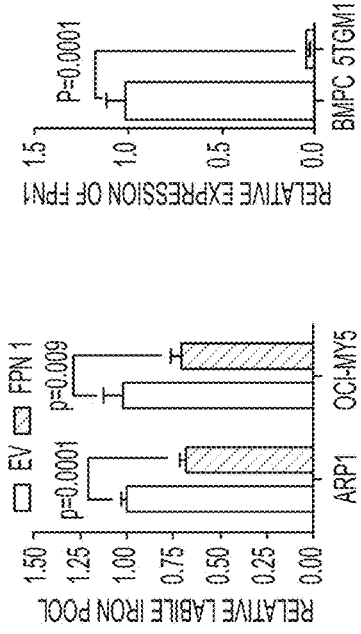
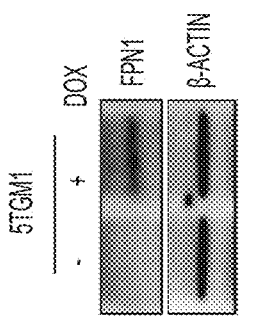
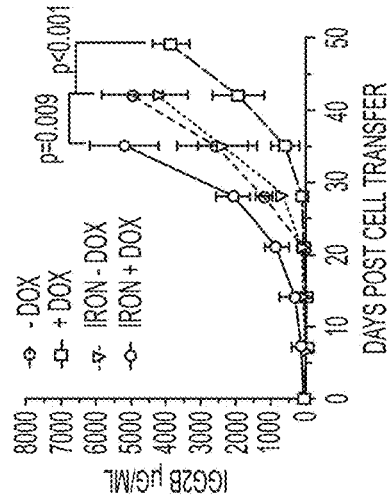
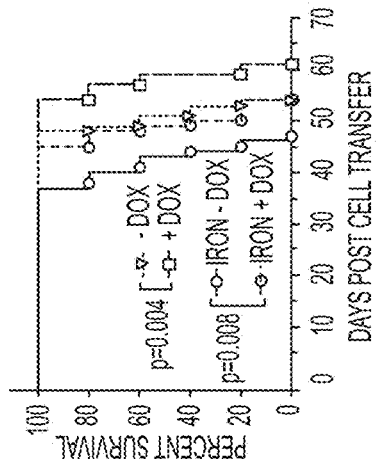

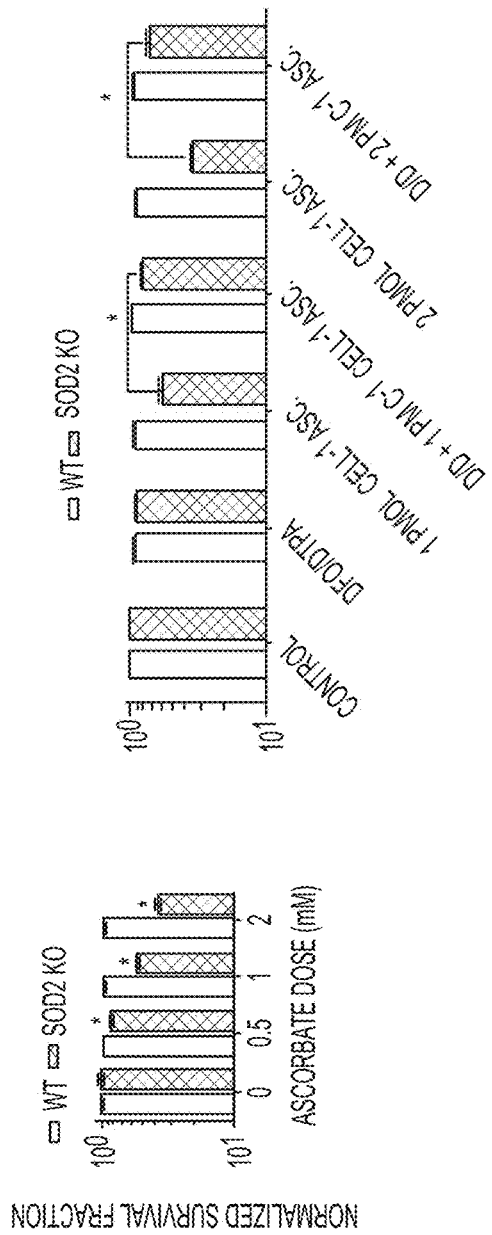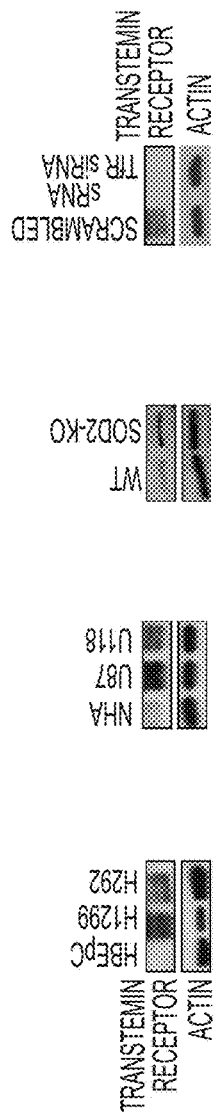

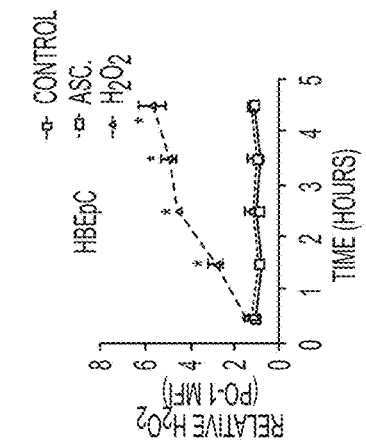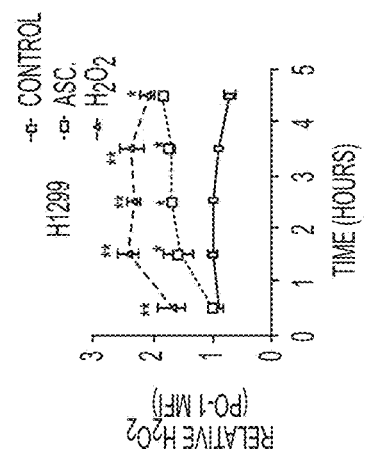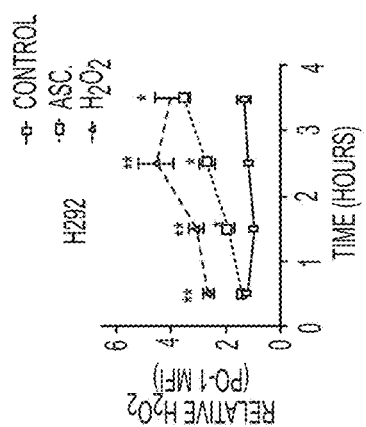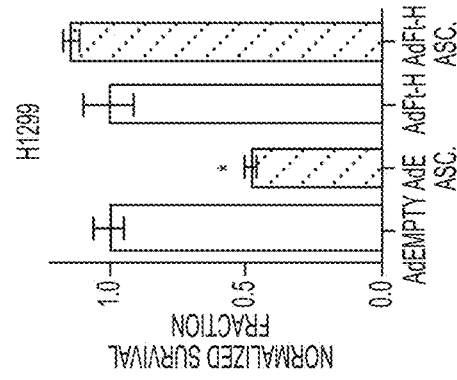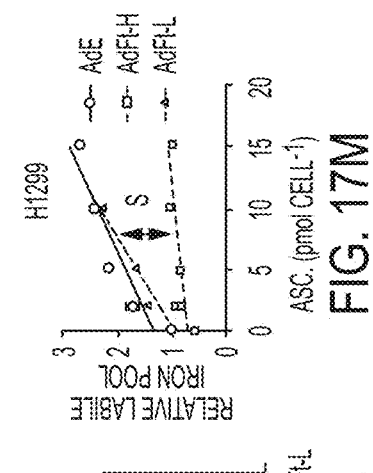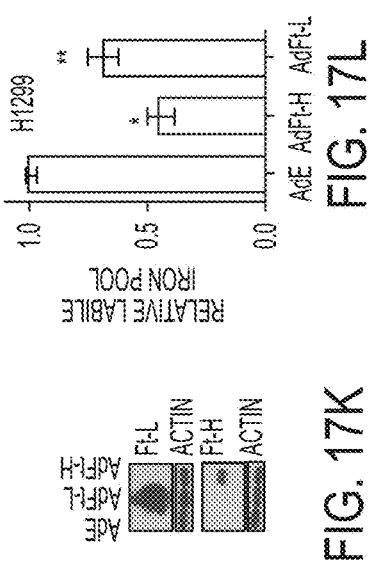

TABLE S1. GBM SUBJECT DEMOGRAPHICS AND DISEASE STATUS AT TIME OF PRESENTATION

| SUBJECT% | AGE | GENDER | KPS# | TUMOR LOCATION | TUMOR SIZE (cm) | TUMOR RESECTION OR BIOSPY? |
|---|---|---|---|---|---|---|
| SUBJECT 1 | 66 | FEMALE | 100 | R FRONTAL LOBE; PARAMEDIAN | 4.2 × 2.5 × 2.9 | RESECTION |
| SUBJECT 2 | 25 | FEMALE | 100 | R TEMPORAL LOBE | 4.6 × 4.4 × 3.6 | RESECTION |
| SUBJECT 3 | 54 | MALE | 90 | L FRONTAL LOBE | 4.3 × 2.6 × 5.1 | RESECTION |
| SUBJECT 4 | 52 | FEMALE | 90 | CORPUS CALLOSUM (SPLENIUM) | 4.1 × 3.7 × 3.0 | BIOSPY |
| SUBJECT 5 | 45 | MALE | 80 | R TEMPORAL LOBE | 3.5 × 5.3 × 3.1 | RESECTION |
| SUBJECT 6 | 53 | MALE | 90 | L OCCIPITAL LOBE | 5.2 × 4.6 × 4.8 | RESECTION |
| SUBJECT 7 | 44 | FEMALE | 90 | R FRONTAL LOBE | 9.3 × 5.4 × 2.6 | RESECTION |
| SUBJECT 8 | 59 | MALE | 90 | L PREDOMINANTLY INTRAVENTRICULAR | 5.1 × 3.8 × 4.7 | RESECTION |
| SUBJECT 9 | 62 | MALE | 80 | R FRONTAL LOBE | 5.1 × 4.2 × 6.1 | RESECTION |
| SUBJECT 10 | 37 | MALE | 90 | R PARIETAL LOBE | 3.4 × 1.7 × 2.4 | RESECTION |
| SUBJECT 11 | 68 | FEMALE | 90 | L FRONTAL LOBE | 5.9 × 4.0 × 4.2 | RESECTION |
| SUBJECT 12* | 47 | MALE | 70 | R THALAMUS R TEMPORAL LOBE | 1.8 × 1.5 × 1.6 1.1 × 0.7 × 0.9 | BIOSPY |
| SUBJECT 13* | 71 | FEMALE | 70 | R TEMPOROPARIETAL LOBE | 4.2 × 4.1 × 2.1 | BIOSPY |

KPS = KARNOFSKY PERFORMANCE STATUS
% SUBJECT NUMBERS ARE FOR CONVENIENCE AND NOT REPRESENTATIVE OF CASE ID NUMBERS.
* SUBJECTS 12 AND 13 ARE INCLUDED IN THE TOXICITY ANALYSIS (TABLES S2), BUT WERE NOT INCLUDED IN THE PROGRESSION FREE SURVIVAL AND OVERALL SURVIVAL ANALYSIS (FIG. 6) BECAUSE THEY RECEIVED LIMITED PROTOCOL-DICTATED THERAPY DUE TO BACKGROUND DISEASE.

FIG. 26

TABLE S2. GRADE 3/4 HEMATOLOGICAL TOXICITIES IN GBM SUBJECTS COMPARED TO HISTORICAL CONTROLS

| RADIATION THERAPY PHASE | | |
|---|---|---|
| ADVERSE EVENT | TMZ + RT + Asc (n = 13) | TMZ + RT STUPP et al. (n = 284) |
| LEUKOPENIA | 0 (0%) | 7 (2%) |
| NEUTROPENIA | 0 (0%) | 12 (4%) |
| THROMBOCYTOPENIA | 0 (0%) | 9 (3%) |
| ANEMIA | 0 (0%) | 1 (<1%) |
| ADJUVANT PHASE | | |
| ADVERSE EVENT | TMZ + Asc (n = 12) | TMZ STUPP et al. (n = 223) |
| LEUKOPENIA | 1 (8%) | 11 (5%) |
| NEUTROPENIA | 1 (8%) | 9 (4%) |
| THROMBOCYTOPENIA | 0 (0%) | 24 (11%) |
| ANEMIA | 0 (0%) | 2 (1%) |

FIG. 27

TABLE S3. SUBJECT REPORTED NON-HEMATOLOGICAL TOXICITIES IN GBM SUBJECTS COMPARED TO HISTORICAL CONTROLS

| RADIATION THERAPY PHASE | | | | |
|---|---|---|---|---|
| | TMZ + RT + ASC. (n = 13) | | TMZ + RT (Stupp et al.) (n = 284) | |
| ADVERSE EVENT | GRADE 2 | GRADE 3/4 | GRADE 2 | GRADE 3/4 |
| FATIGUE | 3 (23%) | 1 (8%) | 74 (26%) | 19 (7%) |
| RASH | 0 (0%) | 0 (0%) | 26 (9%) | 4 (1%) |
| INFECTION | 1 (8%) | 0 (0%) | 3 (1%) | 9 (3%) |
| VISION | 0 (0%) | 0 (0%) | 39 (14%) | 3 (1%) |
| NAUSEA | 5 (38%) | 1 (8%) | 38 (13%) | 2 (<1%) |
| VOMITING | 0 (0%) | 2 (15%) | | |
| ADJUVANT PHASE | | | | |
| | TMZ + RT + ASC. (n = 12) | | TMZ (Stupp et al.) (n = 223) | |
| ADVERSE EVENT | GRADE 2 | GRADE 3/4 | GRADE 2 | GRADE 3/4 |
| FATIGUE | 2 (15%) | 0 (0%) | 73 (25%) | 18 (6%) |
| RASH | 0 (0%) | 0 (0%) | 13 (5%) | 5 (2%) |
| INFECTION | 0 (0%) | 0 (0%) | 6 (2%) | 12 (5%) |
| VISION | 0 (0%) | 0 (0%) | 28 (10%) | 2 (<1%) |
| NAUSEA | 4 (31%) | 0 (0%) | 52 (18%) | 4 (1%) |
| VOMITING | 1 (8%) | 0 (0%) | | |

* ALTHOUGH NOT TRACKED BY Stupp et al., THE MOST COMMON ADVERSE EVENT IN THIS PHASE I TRIAL WAS DRY MOUTH, OCCURRING IN 8 OF 13 PATIENTS (GRADE 1; RT PHASE) AND 9 OF 12 SUBJECTS (8 - GRADE 1, 1 - GRADE 2; ADJUVANT PHASE). ADDITIONALLY, CHILLS WERE REPORTED BY 7 OF 13 SUBJECTS (GRADE 1; RT PHASE) AND 6 OF 12 SUBJECTS (GRADE 1; ADJUVANT PHASE).

FIG. 28

TABLE S4. NSCLC SUBJECT DEMOGRAPHICS AND DISEASE STATUS AT TIME OF PRESENTATION

| SUBJECT% | AGE | GENDER | DISEASE SITES | HISTOLOGY# | ECOG STATUS* | SMOKING STATUS | EGFR/ALK MUTATION STATUS@ |
|---|---|---|---|---|---|---|---|
| 1 | 54 | MALE | RML, CLAVICLE, THORACIC/LUMBAR SPINE, BILATERAL PELVIC BONES | SCC | 1 | NEVER | NEGATIVE |
| 2 | 62 | FEMALE | LLL, THORACIC/LUMBAR SPINE, BILATERAL PELVIC BONES, LIVER | AC | 1 | > 20 PACK YEARS | NEGATIVE |
| 3 | 64 | MALE | LUL, LEFT ADRENAL GLAND, CHEST WALL | AC | 1 | > 20 PACK YEARS | NEGATIVE |
| 4 | 53 | MALE | RLL, LIVER, BRAIN | SCC | 1 | > 20 PACK YEARS | N/A |
| 5 | 64 | MALE | RUL, THORACIC SPINE | AC | 1 | > 20 PACK YEARS | NEGATIVE |
| 6 | 67 | FEMALE | LLL, LUMBAR SPINE | AC | 1 | NEVER | NEGATIVE |
| 7 | 58 | MALE | LUL, MEDIASTINUM, RUL | SCC | 1 | > 20 PACK YEARS | N/A |

%SUBJECT NUMBERS ARE FOR CONVENIENCE AND NOT REPRESENTATIVE OF CASE ID NUMBERS.
*SCC = SQUAMOUS CELL CARCINOMA; AC = ADENOCARCINOMA
*ECOG = EASTERN COOPERATIVE ONCOLOGY GROUP SCORE (0 - 5; 0 = ASYMPTOMATIC, 5 = DEATH)
@EGFR/ALK MUTATION ANALYSIS RECOMMENDED FOR ALL AC SUBJECTS. ANALYSIS WAS PERFORMED FOR SUBJECT 1 DUE TO PATIENT DENYING ANY SMOKING HISTORY. N/A = NOT APPLICABLE.

FIG. 29

COMPOSITIONS AND METHODS FOR CANCER THERAPY

CROSS-REFERENCE TO RELATED APPLICATIONS

This application claims priority to U.S. Provisional Application No. 62/240,372 that was filed on Oct. 12, 2015. The entire content of the applications referenced above and hereby incorporated by reference herein.

FEDERAL GRANT SUPPORT

The invention was made with government support under T32 CA078586 and JF2014-1 awarded by NIH/NCI. The government has certain rights in the invention.

BACKGROUND

Most treatment plans for patients with cancer include surgery, radiation therapy, and/or chemotherapy. Early clinical trials were performed for the use of vitamin C (ascorbic acid) to treat cancer, but epidemiological studies evaluating the association between the intake of vitamin C and cancer risk produced inconsistent results. (Luo, et al., Association between vitamin C intake and lung cancer: a dose-response meta-analysis, Sci Rep. 2014 Aug. 22; 4:6161) Other studies determined that no significant differences were noted between the ascorbate-treated and placebo-treated groups for symptoms, performance status, or survival (Moertel C G, Fleming T R, Creagan E T, Rubin J, O'Connell M J, Ames M M. High-dose vitamin C versus placebo in the treatment of patients with advanced cancer who have had no prior chemotherapy. A randomized double-blind comparison. N Engl J Med. 1985; 312(3):137-41; Creagan E T, Moertel C G, O'Fallon J R, Schutt A J, O'Connell M J, Rubin J, Frytak S. Failure of high-dose vitamin C (ascorbic acid) therapy to benefit patients with advanced cancer. A controlled trial. N Engl J Med. 1979; 301(13):687-90). There is a need for more efficacious cancer treatments with minimal side effects.

SUMMARY

In certain embodiments, the present invention provides a combination of (a) ascorbate or a pharmaceutically acceptable salt thereof; (b) at least one metal (Iron) chelator that enhances redox cycling, wherein the at least one chelator is at a dose of 35-50 mg/kg, and wherein the at least one chelator is at least at a purity level of Current Good Manufacturing Practice (CGMP) regulations; and (c) one or more anti-cancer therapies for the therapeutic treatment of a hyperproliferative disorder.

In certain embodiments, the ascorbate is at a concentration of about at least greater than or equal to 20 mM plasma concentration (350 mg/dL). In certain embodiments, the chelator is ethylene diamine tetraacetic acid (EDTA). In certain embodiments, the chelator is calcium disodium EDTA. In certain embodiments, the chelator is magnesium EDTA.

In certain embodiments, the anti-cancer therapy is a chemotherapeutic agent and/or radiation therapy.

In certain embodiments, the chemotherapeutic agent is paclitaxel and carboplatin.

In certain embodiments, the combination further comprises an inhibition agent that inhibits glucose and/or hydroperoxide metabolism. In certain embodiments, the inhibition agent is: Buthionine sulfoximine, Auranofin, 2-deoxyglucose, other inhibitors of glutathione and/or thioredoxin metabolism, inhibitors of catalase, sulfasalazine, other inhibitors of cysteine transport, inhibitors of glucose transport, diets that limit glucose and other simple sugars such as ketogenic diets.

In certain embodiments, the hyperproliferative disorder is cancer. In certain embodiments, the cancer is lung cancer, pancreatic cancer, brain cancer, lung cancer, head and neck cancer, prostate cancer, sarcomas, skin cancer, or blood born tumors including multiple myeloma. In certain embodiments, the cancer is non-small cell lung cancer.

In certain embodiments, the present invention provides a method for treating a hyperproliferative disorder in a mammal, comprising administering to the mammal a combination of ascorbate, a chelating agent and an anti-cancer therapy.

In certain embodiments, the ascorbate, a chelating agent is administered for more than a month. In certain embodiments, the ascorbate and a chelating agent is administered for more than a year.

In certain embodiments, the ascorbate is administered at a dosage of at least 75 g/day and the chelating agent is administered at a dosage of at least 35 mg/day.

In certain embodiments, the ascorbate and calcium disodium EDTA is administered intravenously.

In certain embodiments, the ascorbate is administered at a dosage of at least 50 g/infusion and the chelating agent is administered at a dosage of at least 35 mg/kg/day.

In certain embodiments, a) ascorbate and chelating agent are administered simultaneously with the one or more anti-cancer therapies; or b) ascorbate and chelating agent and the one or more anti-cancer therapies are administered sequentially; or c) administration of the one or more anti-cancer therapies begins about 1 to about 10 days before administration of the ascorbate and chelating agent; or d) administration of ascorbate and chelating agent begins about 1 to about 10 days before administration of the one or more anti-cancer therapies; or e) administration of ascorbate and chelating agent and administration of the one or more anti-cancer therapies begins on the same day.

In certain embodiments, ascorbate or the pharmaceutically acceptable salt thereof is administered after or concurrently with the chelator and/or with the one or more anti-cancer therapies.

In certain embodiments, the ascorbate or the pharmaceutically acceptable salt thereof and the chelator and the one or more anti-cancer therapies are administered sequentially.

In certain embodiments, the ascorbate, the chelator and the one or more anti-cancer therapies begin on the same day.

In certain embodiments, the ascorbate and the chelator are administered about less than four hours prior to the administration of the one or more anti-cancer therapies.

In certain embodiments, the anti-cancer therapy is chemotherapy, immunotherapy, biologic therapy, or radiation therapy.

In certain embodiments, the radiation therapy is external beam or targeted radionuclide based therapy. In certain embodiments, the radiation therapy is given for curative intent. In certain embodiments, the radiation therapy is administered at a dose of about 1.8 to 2 Gy for 25 or more fractions.

In certain embodiments, the hyperproliferative disorder is cancer. In certain embodiments, the cancer is lung cancer (non-small cell lung cancer (NSCLC) and small cell lung cancer), pancreatic cancer, brain cancer, lung cancer, head and neck cancer, prostate cancer, skin cancer, sarcoma, or blood born tumors including multiple myeloma.

In certain embodiments, the hyperproliferative disorder is non-small cell lung cancer, and pharmacological doses of ascorbate, calcium disodium EDTA, paclitaxel, and carboplatin are administered.

In certain embodiments, the ascorbate is administered at a dose of about 75 g-100 g infusion 2-5 times per week, calcium disodium EDTA is administered at a dose of about 35-50 mg/kg per day, paclitaxel is administered at a dose of about 200 mg/m$^2$ (meter squared of body surface area) every 3 weeks, and carboplatin is administered at a dose of about AUC (area under the curve) 6 every 3 weeks. In certain embodiments in the case of lung cancer, the chemotherapeutic agent is paclitaxel (200 mg/m$^2$ every 3 weeks) and carboplatin (AUC 6 every 3 weeks).

In certain embodiments, the hyperproliferative disorder is sarcoma, and pharmacological doses of ascorbate, calcium disodium EDTA, and adriamycin or gemcitabine are administered. In the setting of sarcoma, adriamycin (75 mg/m$^2$ every 3 weeks) or gemcitabine (1000 mg/m$^2$ day 1, day 8, day 15 followed by 3 weeks off). In the setting of multiple myeloma (MM), carfilzomib 56 mg/m$^2$ every week or melphalan (200 mg/m$^2$, reduced to 140 mg/m$^2$ for patients ≥70 years old or with a creatinine ≥2 mg/dl). In certain embodiments, the radiation therapy is external beam radiation therapy, stereotactic body radiation therapy, proton therapy, and/or brachytherapy.

In certain embodiments, 50 g/infusion or greater ascorbate and 35 mg/kg or greater EDTA is administered in combination with paclitaxel (200 mg/m$^2$ every 3 weeks) and carboplatin (AUC 6 every 3 weeks), in the cancer setting of non-small cell lung cancer. In the setting of sarcoma, adriamycin (75 mg/m$^2$ every 3 weeks) or gemcitabine (1000 mg/m$^2$ day 1, day 8, day 15 followed by 3 weeks off). In the setting of multiple myeloma (MM), carfilzomib 56 mg/m$^2$ every week or melphalan (200 mg/m$^2$, reduced to 140 mg/m$^2$ for patients ≥70 years old or with a creatinine ≥2 mg/dl).

In certain embodiments, the ascorbate is administered at a dose of about 75 g-100 g infusion 2-5 times per week, the calcium disodium EDTA is administered at a dose of about 35-50 mg/kg per day, and adriamycin is administered at a dose of about 75 mg/m$^2$ every 3 weeks or gemcitabine is administered at a dose of about 1000 mg/m$^2$ on day 1, day 8, and day 15, and then repeated after 3 weeks.

In certain embodiments, the present invention provides a use of ascorbate, a chelating agent and one or more anti-cancer therapies for the therapeutic treatment of a hyperproliferative disorder.

In certain embodiments, the present invention provides a use of the combination of ascorbate, a chelating agent and an anti-cancer agent in the preparation of a medicament for the treatment of a hyperproliferative disorder in a mammal.

In certain embodiments, the present invention provides a kit comprising ascorbate, a chelating agent and an anti-cancer agent, a container, and a package insert or label indicating the administration of the ascorbate and a chelating agent with one or more anti-cancer agents for treating a hyperproliferative disorder.

In certain embodiments, the present invention provides a product comprising ascorbate, a chelating agent and an anti-cancer agent as a combined preparation for separate, simultaneous or sequential use in the treatment of a hyperproliferative disorder.

BRIEF DESCRIPTION OF THE DRAWINGS

FIGS. 2A-2H. NSCLC tumors have increased steady-state levels of superoxide relative to normal lung epithelium. Human normal (FIGS. 2A-2C) and lung cancer tissues (FIGS. 2D-2F) were harvested and exposed to 10 μM DHE or H&E stain. Confocal microscopy images were taken and mean fluorescence intensities (MFI) of 300 cells from at least three images per section were measured using ImageJ and the means of these images were submitted for statistical analysis (2G-2H) (*=$p<0.05$ comparing normal vs. tumor tissue).

(FIG. 5A) NCI-H292 cells were treated with either 2 mM ascorbate for 1 hr with or without 0.75 mM PEG-catalase followed by clonogenic survival analysis. The addition of PEG-catalase inhibited ascorbate toxicity. (FIG. 5B) NCI-H292 cells were treated with Deferoxamine and Detapac for 2 hours followed by exposure to 2 mM ascorbate for 1 hour. Chelation of metals prior to pharmacologic ascorbate exposure inhibited ascorbate toxicity (* $p<0.05$ compared to control NCI-H292).

(FIG. 7A) Mice bearing NSCLC xenografts were treated with a combination of saline, ascorbate, carboplatin+radiation (carbo IR) or ascorbate+carboplatin+radiation (asc carbo IR). The results show a significant enhancement of survival for mice treated with ascorbate+chemo-radiation vs. chemo-radiation alone ($p=0.023$). (FIG. 7B) Plasma from mice treated with intraperitoneal ascorbate injections have significantly increased plasma ascorbate concentrations ($p<0.03$). Tumor concentrations trended towards significance compared to control mice ($p=0.0659$).

FIGS. 9A-9H. Identification of FPN1 as a poor prognostic marker in multiple myeloma. (FIG. 9A), supervised cluster analysis of iron signature genes in NPCs and multiple myeloma cells. (FIG. 9B), scatter plots depict the Affymetrix signal of FPN1 in NPCs, MGUS, newly diagnosed multiple myeloma (MM; TT2 cohort), and multiple myeloma cell lines (MMCL). One-way ANOVA was performed and identified the P<0.0001 among these four groups. The P value presented in the figure was obtained by comparison between NPC and indicated group, respectively. (FIG. 9C), the expression of FPN1 among 8 multiple myeloma subgroups is highly variable (P<0.0001 by one-way ANOVA). Indicated P value was obtained among 8 subgroups by one-way ANOVA. (FIG. 9D), expression of FPN1 between low- and high-risk subgroups in multiple myeloma. The difference was compared by the Student t test between these two groups. (FIGS. 9E-9H), survival analyses were performed based on FPN1 expression in different cohorts. The EFS (FIG. 9E) and OS (FIG. 9F) were performed in the TT2 cohort, and OS was also analyzed in the HOVON65 (FIG. 9G) and APEX (FIG. 9H) clinical trials.

FIGS. 10A-10E. FPN1 regulates multiple myeloma cell intracellular iron in vitro and in vivo. (FIG. 10A), high FPN1 decreases intracellular LIP. The intracellular LIP was measured in indicated cells using fluorescent metallosensor calcein. (FIG. 10B), FPN1 expression is significantly lower in mouse multiple myeloma cells than in normal mouse plasma cells. Expression of FPN1 mRNA in normal bone marrow plasma cells from wild-type KaLwRij mice and 5TGM1 cells was measured by qRT-PCR and compared by the Student t test. (FIG. 10C), confirmation of FPN1 expression in an inducible mouse multiple myeloma cell line. Inducible expression of FPN1 in 5TGM1 cells was detected by Western blot. (FIGS. 10D and 10E), high FPN1 antagonizes iron-induced cell growth in vivo. 5TGM1-FPN1 KaLwRij mice were administrated with or without doxycycline and dextran-iron as indicated 1 week after cell injection. Kaplan-Meier showed the survival curves, and P value was analyzed by the log-rank test. (FIG. 10D), tumor burden was measured by the ELISA assay, and the significance (P<0.0001) was determined by one-way ANOVA.

(FIGS. 13A-13B) Clonogenic survival post-exposure of (FIG. 13A) NSCLC cell lines H1299 and H292 and HBEpCs or (FIG. 13B) GBM cell lines U87 and U118 and NHAs to increasing doses of pharmacological ascorbate for 1 h. (FIGS. 13C-13E) Clonogenic survival of NSCLC and HBEpCs post serial exposure to 5 µM carboplatin for 1 h, ascorbate for 1 h, and 2 Gy IR. (FIGS. 13F-13H) Clonogenic survival of GBM and NHAs post serial exposure to 5 µM carboplatin for 1 h, ascorbate for 1 h, and 2 Gy IR. For all in vitro studies, n≥3. Data are represented as mean±SEM. *, , or * represent significant differences between groups, at least p<0.05.

(FIG. 14A) Overall survival of H292 murine xenografts treated with chemoradiation (5 mg kg$^{-1}$ carboplatin weekly, 12 Gy IR/2 fx) with or without ascorbate (4 g kg$^{-1}$ ascorbate IP or equivalent osmotic dose of NaCl daily). (FIG. 14B) Overall survival of U87 murine xenografts treated with radiochemotherapy (25 mg kg$^{-1}$ temozolomide weekly, 12 Gy IR/2 fx) with or without ascorbate (4 g kg$^{-1}$ IP ascorbate or equivalent osmotic dose of NaCl daily). Mice were sacrificed when tumors reached 15 mm in the longest direction. (FIGS. 14C-14D) Average weight of mice with (FIG. 14C) H292 or (FIG. 14D) U87 xenografts. (FIG. 14E) Plasma and (FIG. 14F) tumor ascorbate concentrations from H292 mouse xenograft tissue collected 1 h after IP ascorbate treatment (4 g kg$^{-1}$ or equivalent osmotic dose of NaCl). (FIG. 14G) Representative sample of an EPR spectra monitoring for the ascorbyl radical at g=2.0 from CSF collected from healthy nude athymic female mice 1 h after IP treatment with ascorbate (4 g kg$^{-1}$) or equivalent dose of NaCl. For all in vivo studies, mice n≥7. For all ex vivo studies, n≥3. Data are represented as mean±SEM. *represents significant difference, at least p<0.05.

(FIGS. 15A, 15B) Clonogenic survival of (FIG. 15A) H292 or (FIG. 15B) U87 cells co-exposed to 50 U mL$^{-1}$ bovine catalase±ascorbate for 1 h. (FIGS. 15C, 15D) Clonogenic survival of H1299 cells overexpressing (FIG. 15C) catalase or (FIG. 15D) GPx1 (50 MOI) following exposure to ascorbate for 1 h. For GPx1 experiments, 20 nM sodium selenite was added to the basal media after transduction and during clonogenic growth. (FIGS. 1 E, 15F) Clonogenic survival of (FIG. 15E) H292 and (FIG. 15F) U118 cells treated with 200 µM DFO and 1 mM DTPA 3 h prior and during exposure to ascorbate for 1 h. (FIGS. 15G-15I) H292 cells were exposed to (FIG. 15G) 200 µM DFO/1 mM DTPA, (FIG. 15H) 1 mM EDTA, or (FIG. 15I) 250 µM FAS for 3 h prior to ascorbate exposure ('intracellular') or media was pretreated for 3 h in the absence of cells and co-exposed to cells only during 1 h ascorbate exposure ('extracellular') and then plated for clonogenic survival. For FAS extracellular treatment group, 250 µM FAS was added just prior to ascorbate exposure to prevent premature oxidation. For all in vitro studies, n≥3. Data are represented as mean±SEM. *represents significant difference, at least p<0.05.

(FIGS. 16A-16C) 10 µm sections of NSCLC or adjacent normal tissue were stained with 10 µM DHE on the same slide for 30 mM prior to analysis by confocal microscopy. For treatment groups, tissue sections were pretreated for 30 min with 0.5 µM GC4419 SOD mimetic prior to DHE exposure. For a positive control, tissue sections were incubated with 10 antimycin A during DHE staining. The mean fluorescence intensity of ≥200 nuclei from 6 randomly selected areas was quantified using ImageJ software.

K) against a standard curve and normalized to total tissue protein. Each data point represents the average of triplicate technical replicates. (FIGS. 16H, 16I) Clonogenic survival of HEL 92.1.7 and daughter SOD2-KO cells in a 3-D agar system was measured post exposure to (FIG. 16H) increasing doses of ascorbate at baseline or (FIG. 16I) after pre-incubation for 3 h to 200 µM DFO/1 mM DTPA. (FIGS. 16J-16M) Western blot analysis of TfR protein levels (25 µg total protein) in (FIG. 16J) HBEpC and NSCLC cells, (FIG. 16K) NHA and GBM cells, (FIG. 16L) HEL92.1.7 parent and SOD2-KO daughter cells, and (FIG. 16M) H1299 cells treated with 25 pmol siRNA/dish with actin protein loading controls.

FIGS. 17A-17N. Ascorbate selectively increases cancer cell LIP via $H_2O_2$-mediated disruptions of Fe—S clusters. See also Figure S4. (FIGS. 17A, 17B) LIP levels after exposure to increasing doses of ascorbate in (FIG. 17A) HBEpCs and NSCLC cells or (FIG. 17B) NHAs and GBM cells as assayed by Calcein-AM using flow cytometry. (FIGS. 17H-17J) Relative intracellular steady-state $H_2O_2$ levels as measured with the fluorescent probe PO-1 in (FIG. 17H) H292, (FIG. 17I) H1299, or (FIG. 17J) HBEpCs treated with 15 pmol cell$^{-1}$ ascorbate once or 100 µM $H_2O_2$ every 30 mins (FIG. 17K) Representative western blot of H1299 cells transduced with 20 MOI AdEmpty, AdFerritin-Heavy Chain, or AdFerritin-Light Chain with Actin protein loading control 36 h after transduction. (FIG. 17L) Baseline LIP and (FIG. 17M) LIP after 1 h ascorbate exposure in H1299 cells overexpressing AdE, AdFt-H, AdFt-L (20 MOI) as assayed by Calcein-AM by flow cytometry (FIG. 17N) Clonogenic survival of H1299 cells overexpressing AdE or AdFt-H (20 MOI) exposed to 5 pmol cell$^{-1}$ for 1 h. For all in vitro studies, n≥3. Western blots are a representative images of 3 replicates. Data are represented as mean±SEM. *represents significant difference, at least p<0.05.

(FIG. 18A) Progression Free Survival (PFS) and Overall Survival (OS) of subjects treated with pharmacological ascorbate, radiation and temozolomide. The phase I clinical trial was designed to determine the safety and tolerability of combining pharmacological ascorbate with radiation and temozolomide therapy in GBM patients based on the Stupp et al (2005) regimen administering temozolomide daily with concurrent radiation therapy followed by 28 additional weeks of temozolomide therapy. Historical median PFS is 7 months and OS is 14 months. The vertical arrows indicate pre-mature cessation of the clinical trial due to personal reasons; vertical light blue lines indicate cessation of the trial due to progression of disease while receiving ascorbate therapy; and vertical black lines indicate death. Subjects who had recurrence confirmed surgically are marked with an asterisk. The green bars indicate the duration of active ascorbate therapy, blue bars PFS, and red bars OS. (FIG. 18B) Estimated overall survival (OS) as determined by the method of Kaplan-Meier is 28.4 months (orange line marked with red dot). 95% confidence interval region is indicated (greyfield) with a median OS of 15.5 months to infinity. The historical OS of subjects treated with radiation+ temozolomide (Stupp et al., 2005) is indicated by the blue line. (FIG. 18C) Subjects plasma ascorbate levels were measured from blood samples collected directly after ascorbate infusion during dose escalation and throughout ascorbate therapy to ensure subjects reached therapeutic levels (20 mM). (FIG. 18D) Pre- and post-therapy CT images from NSCLC Subject 1 illustrating the decrease in tumor volume (red dashed line). (FIG. 18E) Spider plot illustrating therapy responses from the first six advanced stage NSCLC subjects. As per RECIST1.1, partial response is ≥30% reduction in target tumor burden. Although subject 6 demonstrated stable disease in target lesions, a new C2 spinal lesion automatically qualifies the patient as progressing (red line). From the first six patients, there was a disease control rate of 83% and an objective response rate of 67%, as compared to historical controls with 15-19% objective response rates. On average, patient plasma ascorbate level after 75 g infusions was 16.4±0.5 mM.

(FIGS. 21A, 21B) Clonogenic survival of (FIG. 21A) H1299 or (FIG. 21B) U118 cells co-exposed to 50 U mL$^{-1}$ bovine catalase±ascorbate for 1 h. (FIGS. 21C, 21D) Clonogenic survival of H1299 and U87 cells treated with 200 µM DFO and 1 mM DTPA 3 h prior and during exposure to ascorbate for 1 h. For all in vitro studies, n≥3. Data are represented as mean±SEM. *represents significant difference, at least p<0.05.

(FIG. 23A) Western blot of SOD2 protein levels in WT HEL 92.1.7 and SOD-2 KO daughter cells with a tubulin loading control. (FIG. 23B) SOD2 activity in WT HEL 92.1.7 and SOD-2 KO daughter cell lysates normalized to total protein. Due to the potential presence of residual MnSOD activity, a (FIG. 23C) SOD activity gel was used to confirm the specific absence of MnSOD activity. For activity assays, n=3. Data are represented as mean±SEM. *represents significant difference, at least p<0.05.

(FIG. 25A) Clinical trial schema for patients enrolled in NCT 01049880, a phase I clinical trial assessing the safety and tolerability of pharmacological ascorbate in combination with IR and TMZ in GBM patients (FIG. 25B) Clinical trial schema for subjects enrolled in NCT 02420314, a phase II trial assessing the efficacy of pharmacological ascorbate with platinum-based chemotherapy in advanced stage NSCLC.

FIG. 26. GBM Subject Demographic and Disease Status at Time of Participation.

FIG. 27. Grade 3/4 Hematological Toxicities in GBM Subjects.

FIG. 28. Subject Reported Non-Hematological Toxicities in GBM Subjects Compared to Historical Controls.

FIG. 29. NSCLC Subject Demographics and Disease Status at Time of Presentation.

DETAILED DESCRIPTION

Figure 1:
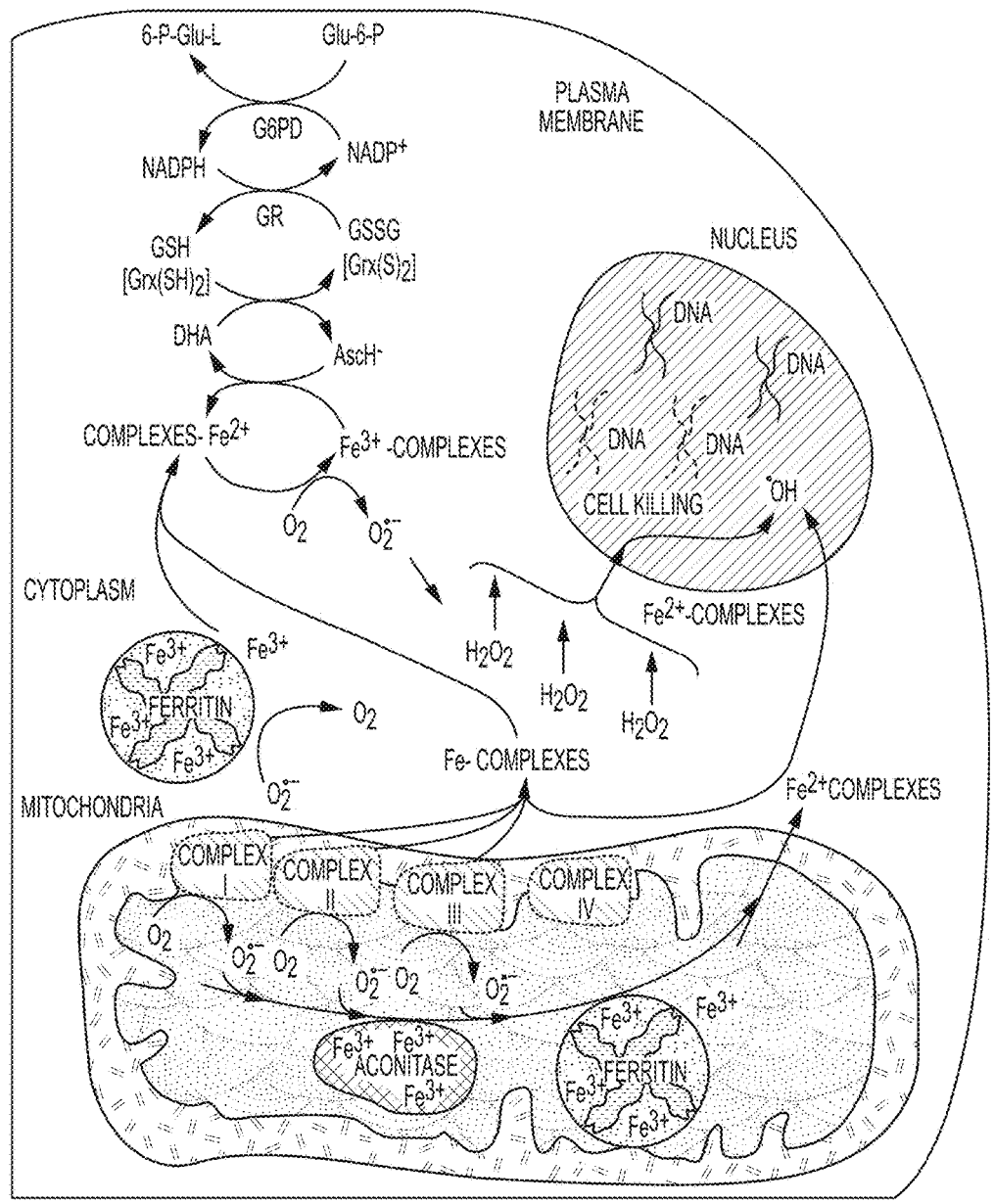
FIG. 1. Theoretical model for the increased generation of $H_2O_2$ by pharmacological ascorbate (AscH$^-$) in cancer cells. Cancer cells demonstrate increased steady-state levels of mitochondrial superoxide ($O_2 .^-$) that react with $Fe^{+3}$ bound to proteins (i.e., FeS-proteins and ferritin) to mobilize small molecular weight chelates of $Fe^{+2}$ that are capable of redox cycling to catalyze the auto-oxidation of ascorbate (ASCH- and recycling of dehydroascorbate (DHA)) to generate $H_2O_2$. This mechanism may explain why cancer cells generate excess amounts of $H_2O_2$ in the presence of pharmacological ascorbate that may enhance chemo-radio-sensitization, relative to normal cells.

Lung cancer is the leading cause of cancer deaths, with 1.3 million deaths/year occurring worldwide. The majority of lung cancers are histologically classified as non-small cell lung cancer (NSCLC). Standard treatment for NSCLC includes a combination of surgery, chemotherapy, and/or radiation therapy. Despite advances in NSCLC treatment, including improved radiation therapy techniques and development of new chemotherapy and biological agents, five-year overall survival rates continue to be poor at approximately 14%. Thus, additional approaches that enhance NSCLC chemo-radiation sensitivity and that are easily implemented with limited toxicity would provide a significant therapeutic advantage. One potential approach with minimal toxicity that exploits fundamental differences in oxidative metabolism between cancer cells and normal cells is pharmacological ascorbate.

Injectable pharmacological ascorbate, or vitamin C, has recently re-emerged as a promising anti-cancer therapy. Studies in a variety of cancer cell types, both in cell culture and animal models, have demonstrated selective (relative to normal cells) cancer cell killing as well as selective sensitization of cancer cells to standard of care therapies when combined with injectable pharmacological ascorbate. Pharmacological ascorbate's selective toxicity to cancer cells appears to be dependent upon the presence of redox active metal ions (such as iron), which are capable of receiving and donating electrons during the oxidation of ascorbate to form hydrogen peroxide. Iron chelators capable of inhibiting this 'redox' activity' can inhibit ascorbate mediated cancer cell toxicity. Alternatively, iron chelators that enhance iron redox cycling, such as ethylenetriaminepentacetic acid (EDTA), have recently been discovered to enhance lung cancer cell killing.

Patients with a variety of cancer types are currently receiving intravenous pharmacological ascorbate in combination with standard cancer therapies in clinical trials to determine pharmacological ascorbate's clinical safety and efficacy. Current ascorbate preparations contain minimal levels (low micromolar concentrations) of EDTA in order to chelate small levels of iron present in the ascorbate solutions to enhance ascorbate stability only. Importantly, the addition of the iron chelators was not intended or known to persons who are expert in the state of the art, to enhance the cancer therapeutic effect.

On the other hand, surprisingly our group recently has discovered that much higher concentrations of EDTA (1 mM and greater) in cell cultures experiments, significantly enhance the cytotoxicity of pharmacological ascorbate in human non-small cell lung cancer cells. We are currently determining if these results are generalizable to several different brain and lung cancer cells lines as well as in human xenograft and orthotopic animals models. If EDTA is found to enhance the therapeutic efficacy of pharmacological ascorbate, this could represent a non-toxic and simple way to enhance therapeutic outcomes in a wide variety of human cancer patients that could lead to the manufacturing of unique preparations of pharmacological ascorbate useful in cancer therapy.

Pharmacological ascorbate has recently been shown in tissue culture models and animal modes to increase the sensitivity of tumor cells to chemotherapy and radiation therapy. In addition, phase I clinical trials assessing the tolerability of pharmacological ascorbate in a variety of cancer types have been well tolerated.

Pharmacological ascorbate toxicity is dependent upon redox active iron. Iron chelation with deferoxamine and Diethylenetriaminepentaacetic Acid (DETAPAC) prevents redox cycling and rescues ascorbate mediated toxicity. Alternatively, iron chelation with millimolar concentrations of ethylenediaminetetraacetic acid (EDTA) enhances iron redox cycling and therefore ascorbate mediated toxicity. Current clinical formulations of pharmacological ascorbate have micromolar concentrations of EDTA to remove loosely bound iron. We propose the application of millimolar concentrations of EDTA to enhance pharmacological ascorbate clinical efficacy by increasing iron redox cycling. This is a novel combination of EDTA with pharmacological ascorbate for the purpose of enhancing treatment efficacy that was previously unrecognized by the experts in this field.

Pharmacological doses of ascorbate (resulting in plasma concentrations ≥10 mM) can be achieved by intravenous (IV) administration and have been shown to be safe and well tolerated in both animals and humans. (Welsh I L, Wagner B A, van't Erve T J, Zehr P S, Berg D J, Halfdanarson T R, Yee N S, Bodeker K L, Du J, Roberts L J 2nd, Drisko J, Levine M, Buettner G R, Cullen J J. Pharmacological ascorbate with gemcitabine for the control of metastatic and node-positive pancreatic cancer (PACMAN): results from a phase I clinical trial. Cancer Chemother Pharmacol. 2013 March; 71(3):765-775; Ma Y, Chapman J, Levine M, Polireddy K, Drisko J, Chen Q. High-Dose Parenteral Ascorbate Enhanced Chemosensitivity of Ovarian Cancer and Reduced Toxicity of Chemotherapy. Sci Transl Med. 2014 Feb. 5; 6(222):222ra18-222ra18). Recent in vitro experiments demonstrate that pharmacological ascorbate is selectively toxic to cancer cells, whereas normal cells are unaffected (preliminary results). (Mechanisms of ascorbate-induced cytotoxicity in pancreatic cancer. Du J, Martin S M, Levine M, Wagner B A, Buettner G R, Wang S H, Taghiyev A F, Du C, Knudson C M, Cullen J J. Clin Cancer Res. 2010 Jan. 15; 16(2):509-20 PMID: 20068072). High ascorbate concentrations in cancer cells appear to selectively induce the formation of $H_2O_2$ via the catalytic oxidation of ascorbate in the presence of redox active metals such as iron (Fe). (Chen Q, Espey M G, Krishna M C, Mitchell J B, Corpe C P, Buettner G R, Shacter E, Levine M. Pharmacologic ascorbic acid concentrations selectively kill cancer cells: action as a pro-drug to deliver hydrogen peroxide to tissues. Proc Natl Acad Sci USA. 2005 Sep. 20; 1 02(38):13604-13609.) Because cancer cells are believed to have higher concentrations of labile redox active metal ions due to increased steady-state levels of superoxide, pharmacological ascorbate will selectively increase $H_2O_2$ in lung cancer cells, relative to normal lung cells, thereby increasing the sensitivity of NSCLC to chemo-radiation therapy by increasing oxidative stress (preliminary results).

Ascorbate (Vitamin C)

Vitamin C is a highly effective and non-toxic anti-oxidant that can be used to protect the body against oxidative stress including free radicals. As used herein, a reference to ascorbic acid includes the anionic component, ascorbate whether as an acid or one of the pharmaceutically acceptable salts thereof, such as sodium ascorbate and calcium ascorbate, all of which are included in a reference to CGMP "ascorbic acid" or "ascorbate.

The method of the present invention comprises the treatment of cancer by administering sufficient amounts of ascorbic acid to raise the concentration of ascorbic acid in the patient's plasma above a level that is cytotoxic to the cancer tumor cells. In certain embodiments, ascorbate is administered so as to reach a blood level of at least about 20 mM. Doses of 75 g/infusion or greater are typically able to achieve this concentration.

Chelating Agents

In certain embodiments, the chelating agent is a cell chelate that enhances redox cycling of metal ions. Examples of such as chelator is calcium disodium EDTA (35-50 mg/kg per day) and magnesium EDTA.

In certain embodiments, the chelating agent is administered so as to reach a blood level of at least about 1 mM.

EDTA (EthyleneDiamineTetraacetic Acid) is a molecule that has the capacity to chelate (bond) almost every positive ion in the periodic table. Chelation therapy is a mainstream treatment used to treat poisoning from toxic levels of certain metals. Injections of EDTA or other chemicals bind, or chelate, iron, lead, mercury, cadmium, zinc, and some other metals, which are then eliminated from the body.

Anti-Cancer Therapy

As used herein, the term "anti-cancer therapy" includes therapeutic agents that kill cancer cells; slow tumor growth and cancer cell proliferation; and ameliorate or prevent one or more of the symptoms of cancer.

For example, the term "anti-cancer therapy" includes an anti-cancer therapy that enhances DNA damage in cancer cells. Examples in the case of non-small cell lung cancer include with paclitaxel (200 $mg/m^2$ every 3 weeks) and carboplatin (AUC 6 every 3 weeks), In the case of sarcoma, adriamycin (75 $mg/m^2$ every 3 weeks) or gemcitabine (1000 $mg/m^2$ day 1, day 8, day 15 followed by 3 weeks off).

In certain embodiments, the anti-cancer therapy is radiation therapy. In certain embodiments, the radiation therapy is standard and/or hypofractionated external beam radiation, as well as High LET radiations from radioactive isotopes or accelerated sources. Dose of radiation depends upon the type of radiation administered and goal of treatment. For curative intent, the minimum dose in fractionated radiation therapy (2 Gy/fraction) is >30 Gy.

Additive Agents

In certain embodiments, the combination further comprises an inhibition agent that inhibits glucose and/or hydroperoxide metabolism. In certain embodiments, the inhibition agent is: Buthionine sulfoximine, Auranofin, 2-deoxyglucose, other inhibitors of glutathione and/or thioredoxin metabolism, inhibitors of catalase, sulfasalazine, other inhibitors of cysteine transport, inhibitors of glucose transport, diets that limit glucose and other simple sugars such as ketogenic diets.

Hyperproliferative Diseases

In certain embodiments of the methods described above, the cancer is breast cancer, prostate cancer, lung cancer, pancreas cancer, head and neck cancer, ovarian cancer, brain cancer, colon cancer, hepatic cancer, skin cancer, leukemia, melanoma, endometrial cancer, neuroendocrine tumors, carcinoids, neuroblastoma, glioma, tumors arising from the neural crest, lymphoma, myeloma, or other malignancies characterized by aberrant mitochondrial hydroperoxide metabolism. In certain embodiments, the cancer is the above cancers that are not curable or not responsive to other therapies. In certain embodiments, the cancer is non-small cell lung cancer (NSCLC). Non-small cell lung cancer forms in the tissues of the lung. Each lung has sections called lobes. The left lung has two lobes. The right lung is slightly larger and has three lobes. Two tubes called bronchi lead from the trachea (windpipe) to the right and left lungs. The bronchi are sometimes also involved in lung cancer. Tiny air sacs called alveoli and small tubes called bronchioles make up the inside of the lungs. There are two main types of lung cancer: non-small cell lung cancer and small cell lung cancer. Each type of non-small cell lung cancer has different kinds of cancer cells. The cancer cells of each type grow and spread in different ways, and are named for the kinds of cells found in the cancer: Squamous cell carcinoma, Large cell carcinoma, and Adenocarcinoma.

For most patients with non-small cell lung cancer, current treatments do not cure the cancer. In NSCLC, results of standard treatment are poor except for the most localized cancers. Surgery is the most potentially curative therapeutic option for this disease. Postoperative chemotherapy may provide an additional benefit to patients with resected NSCLC. Radiation therapy combined with chemotherapy can produce a cure in a small number of patients and can provide palliation in most patients. In patients with advanced-stage disease, chemotherapy or epidermal growth factor receptor (EGFR) kinase inhibitors offer modest improvements in median survival, though overall survival is poor.

Compositions and Methods of Administration

The method of the present invention comprises the treatment of cancer by administering sufficient amounts of ascorbic acid to raise the concentration of ascorbic acid in the patient's plasma above a level that is cytotoxic to the cancer tumor cells, in combination with a chelating agent and an anti-cancer therapy.

The present invention provides a method for increasing the anticancer effects of a conventional cancer therapy (i.e., radio- and/or chemo-therapy) on cancerous cells in a mammal, comprising contacting the cancerous cell with an effective amount of ascorbate/EDTA or a pharmaceutically acceptable salt thereof, and administering an additional conventional cancer therapy modality. In certain embodiments, the additional cancer therapy is chemotherapy and/or radiation. In certain embodiments, the ascorbate/EDTA or a pharmaceutically acceptable salt thereof and anti-cancer agent are administered sequentially to a mammal rather than in a single composition. In certain embodiments, the mammal is a human.

In certain embodiments of the methods described above, the composition does not significantly inhibit viability of comparable non-cancerous cells.

In certain embodiments of the methods described above, the tumor is reduced in volume by at least 10%. In certain embodiments, the tumor is reduced by any amount between 1-100%. In certain embodiments, the tumor uptake of molecular imaging agents, such as fluorine-18 deoxyglucose, fluorine-18 thymidine or other suitable molecular imaging agent, is reduced by any amount between 1-100%. In certain embodiments the imaging agent is fluorine-18 deoxyglucose, fluorine-18 thymidine or other suitable molecular imaging agent. In certain embodiments, the mammal's symptoms (such as flushing, nausea, fever, or other maladies associated with cancerous disease) are alleviated.

Administration of a compound as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Ascorbate, chelating agents and anti-cancer agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., intravenously, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. The amount of active compound in such therapeutically useful compositions is such that an effective dosage level will be obtained.

Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The dosage of the ascorbate, chelating agent(s) and the anti-cancer agent will vary depending on age, weight, and condition of the subject. Treatment may be initiated with small dosages containing less than optimal doses, and increased until a desired, or even an optimal effect under the circumstances, is reached. In general, the dosage is about 75-100 g per infusion Higher or lower doses, however, are also contemplated and are, therefore, within the confines of this invention. A medical practitioner may prescribe a small dose and observe the effect on the subject's symptoms. Thereafter, he/she may increase the dose if suitable. In general, the ascorbate, chelating agent(s) and the anti-cancer agent are administered at a concentration that will afford effective results without causing any unduly harmful or deleterious side effects, and may be administered either as a single unit dose, or if desired in convenient subunits administered at suitable times.

A pharmaceutical composition of the invention is formulated to be compatible with its intended route of administration. For example, the therapeutic agent may be introduced directly into the cancer of interest via direct injection. Additionally, examples of routes of administration include parenteral, e.g., intravenous, slow infusion, intradermal, subcutaneous, oral (e.g., ingestion or inhalation), transdermal (topical), transmucosal, and rectal administration depending on the location of the tumor. Such compositions typically comprise the PBA or pharmaceutically acceptable salt thereof and the anti-cancer agent and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration, and a dietary food-based form. The use of such media and agents for pharmaceutically active substances is well known in the art and food as a vehicle for administration is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

It may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to produce the desired effect(s). The amount of a compound necessary can be formulated in a single dose, or can be formulated in multiple dosage units. Treatment may require a one-time dose, or may require repeated doses.

"Systemic delivery," as used herein, refers to delivery of an agent or composition that leads to a broad biodistribution of an active agent within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

The terms "treat" and "treatment" refer to both therapeutic treatment and prophylactic or preventative measures, wherein the object is to prevent or decrease an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The invention will now be illustrated by the following non-limiting Examples.

EXAMPLE 1

Lung cancer is the leading cause of cancer death in both men and women in the United States; in 2013, approximately 160,000 Americans died from lung cancer. Despite advances in NSCLC treatment including new surgical approaches, improved radiation therapy techniques, and development of novel chemotherapy and biological agents, five year overall survival continues to be poor at approximately 14%. Therefore, novel approaches with minimal toxicity that enhance NSCLC chemo-radiation sensitivity could have a significant clinical impact.

Multiple myeloma is diagnosed in approximately 28,000 people in the US each year and is the cause of death in approximately 13,000 cases. It is the second most common hematologic malignancy after non-Hodgkin's lymphoma. Major progress has been made in the treatment of myeloma with the combination of autologous transplantation and the newer drugs such as IMDs and proteasome inhibitors, resulting in a median survival of 12 years with the most intensive approaches such as Total Therapy III. However, at least 50% of patients will relapse and need effective salvage therapy. The outcome of relapsed myeloma patients is still poor and new treatment modalities are urgently needed for those patients. Again, one potential approach with minimal additional and may be reduced toxicity that exploits fundamental differences in oxidative metabolism between cancer cells and normal cells is pharmacological dosing of ascorbate. There is good rational for the combination of ascorbate with a proteasome inhibitor at a higher dose (carfilzomib 56 mg/m$^2$ every week) and with high-dose melphalan as a pre-transplant preparative regimen to induce strand breaks in addition to the crosslinks caused by the high dose melphalan.

Pharmacological ascorbate was first proposed as an anti-cancer therapy in the 1970s when Cameron and Pauling showed that high doses of ascorbate given both IV and orally increased survival in terminal cancer patients with a variety of cancer types by an average of 300 days. However, two randomized trials at the Mayo Clinic in the 1980s comparing oral ascorbate alone to placebo showed no therapeutic benefit, and interest in ascorbate waned as an anti-cancer agent. (Moertel C G, Fleming T R, Creagan E T, Rubin J, O'Connell M J, Ames M M. High-dose vitamin C versus placebo in the treatment of patients with advanced cancer who have had no prior chemotherapy. (A randomized double-blind comparison. N Engl J Med. 1985; 312(3):137-41. Creagan E T, Moertel C G, O'Fallon J R, Schutt A J, O'Connell M J, Rubin J, Frytak S. Failure of high-dose vitamin C (ascorbic acid) therapy to benefit patients with advanced cancer. A controlled trial. N Engl J Med. 1979; 301(13):687-90.) It is now known that only IV delivery achieves serum ascorbate concentrations that reach effective therapeutic levels (≈20 mM), and this may explain the differences between the Cameron/Pauling and Mayo trials. (Levine M, Padayatty S J, Espey M G. Vitamin C: a concentration-function approach yields pharmacology and therapeutic discoveries. Adv Nutr. 2011; 2(2):78-88. Parrow N L, Leshin J A, Levine M. Parenteral ascorbate as a cancer therapeutic: a reassessment based on pharmacokinetics. Antioxid Redox Signal. 2013; 19(17):2141-56.) Since the 1990s, several groups have demonstrated pharmacological doses of ascorbate are selectively toxic to many cancer types while being non-toxic to normal cells (preliminary data). (Du J, Martin S M, Levine M, Wagner B A, Buettner G R, Wang S, Taghiyev A F, Du C, Knudson C M, Cullen J J. Mechanisms of ascorbate-induced cytotoxicity in pancreatic cancer. Clin Cancer Res 2010 Jan. 15; 16(2):509-520; Cameron E, Pauling L. Supplemental ascorbate in the supportive treatment of cancer: Prolongation of survival times in terminal human cancer. Proc Natl Acad Sci USA. 1976 October; 73(10):3685-3689; Cameron E, Pauling L. Supplemental ascorbate in the supportive treatment of cancer: Reevaluation of prolongation of survival times in terminal human cancer*. Proc Natl Acad Sci USA. 1978 September; 75(9):4538-4542). Furthermore, clinical trials at the University of Iowa in stage IV pancreas cancer patients combining pharmacological ascorbate with gemcitabine demonstrated the tolerability and potential efficacy of this adjuvant therapy. (Welsh J L, Wagner B A, van't Erve T J, Zehr P S, Berg D J, Halfdanarson T R, Yee N S, Bodeker K L, Du J, Roberts L J 2nd, Drisko J, Levine M, Buettner G R, Cullen J J. Pharmacological ascorbate with gemcitabine for the control of metastatic and node-positive pancreatic cancer (PACMAN): results from a phase I clinical trial. Cancer Chemother Pharmacol. 2013 March; 71(3):765-775; Ma Y, Chapman J, Levine M, Polireddy K, Drisko J, Chen Q. High-Dose Parenteral Ascorbate Enhanced Chemosensitivity of Ovarian Cancer and Reduced Toxicity of Chemotherapy. Sci Transl Med. 2014 Feb. 5; 6(222):222ra18-222ra18)

Pharmacological ascorbate is selectively cytotoxic to cancer cells via the generation of $H_2O_2$, which increases cancer cell oxidative stress; however, the mechanism of how pharmacological ascorbate is selectively toxic to cancer cells has yet to be conclusively elucidated. One proposed mechanism of ascorbate's toxicity is shown in FIG. 1. High ascorbate concentrations are believed to induce the formation of $H_2O_2$ via catalytic auto-oxidation in the presence of redox active metal ions such as $Fe^{3+}$.[5] Relative to normal cells, cancer cells have defective oxidative metabolism leading to increased steady-state levels of reactive oxygen species ($O_2.^-$ and $H_2O_2$). (Aykin-Burns N, Ahmad I M, Zhu Y, Oberley L, and Spitz D R. Increased levels of superoxide and hydrogen peroxide mediate the differential susceptibility of cancer cells vs. normal cells to glucose deprivation. Biochem J. 2009; 418:29-37).

Superoxide ($O_2.^-$) is able to react with $Fe^{+3}$ bound to proteins (i.e., Fe—S-proteins and ferritin) to mobilize small molecular weight chelates of $Fe^{+2}$. $Fe^{+2}$ is then able to undergo redox cycling in the presence of ascorbate and $O_2$ generating intracellular $H_2O_2$ (FIG. 1). $H_2O_2$ can then be directly toxic to the cell by oxidizing amino acids on critical protein targets or reacting with $Fe^{2+}$ through Fenton chemistry to produce the highly reactive hydroxyl radical (.OH), which can damage DNA. Because cancer cells are believed to have increased steady-state levels of $O_2.^-$ and $H_2O_2$, we propose NSCLC cells will have increased labile redox active Fe, relative to normal bronchial epithelium, thereby increasing $H_2O_2$ formation by pharmacological ascorbate, leading to increased oxidative stress and sensitivity to chemo-radiation therapy. This mechanism may explain the selectivity of pharmacologic ascorbate in sensitizing cancer versus normal cells.

Lung Tumors Have Increased $O_2 \cdot^-$ Relative to Normal Lung Epithelium.

Figure 2H:
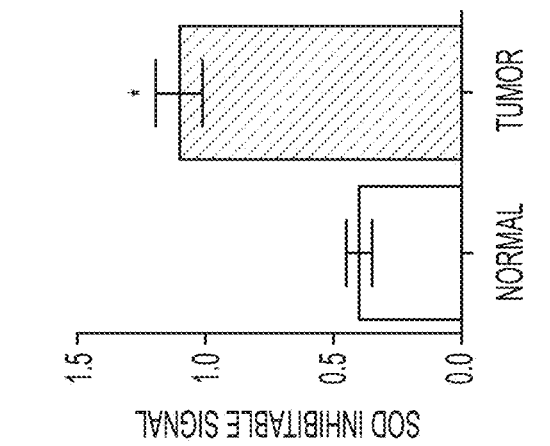
Figure 2G:
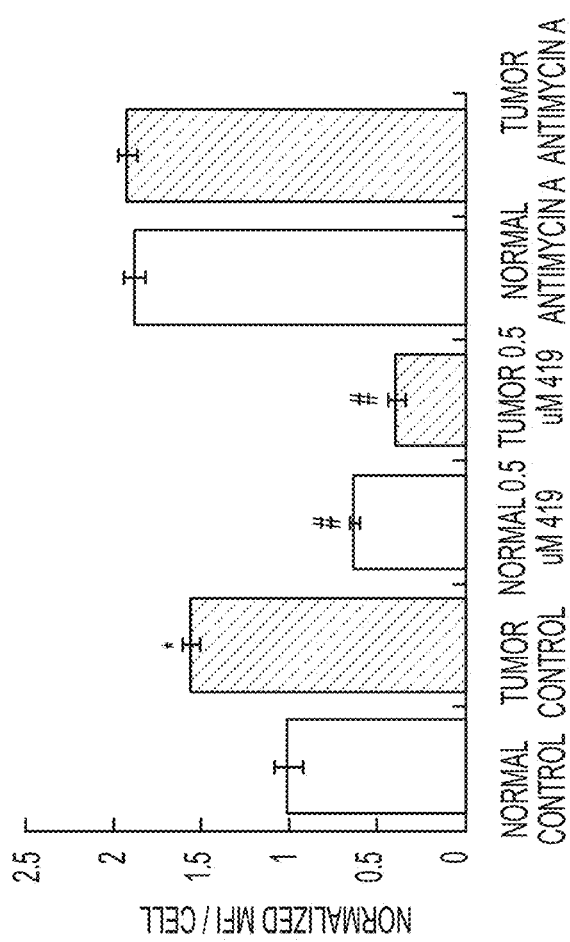

Previous research suggested cancer cells in vitro have alterations in mitochondrial structure and oxygen metabolism leading to increased steady-state levels of reactive oxygen species ($O_2 \cdot^-$ and $H_2O_2$) relative to normal cells. (Aykin-Burns N, Ahmad I M, Zhu Y, Oberley L, and Spitz D R. Increased levels of superoxide and hydrogen peroxide mediate the differential susceptibility of cancer cells vs. normal cells to glucose deprivation. Biochem J. 2009; 418:29-37). To assess if human NSCLC cells in vivo demonstrate increased steady-state levels of relative to normal lung epithelium, freshly frozen tissue samples from early stage NSCLC lobectomies were obtained that contained both tumor and normal lung epithelium. Using dihydroethidum (DHE) oxidation to its red fluorescent products as a surrogate marker of $O_2 \cdot^-$ levels, the relative DHE oxidation in NSCLC tissue versus normal lung epithelium was measured (FIG. 2A vs. 2D) and quantified in three independent patient samples (FIG. 2G). Antimycin A was used as a positive control and the specificity of the signal derived from $O_2 \cdot^-$ was confirmed by the suppression of DHE oxidation with a specific superoxide dismutase mimic (Galera Therapeutics). These data demonstrate that human NSCLC tumors have a 1.7-2.0-fold increases in steady-state levels of $O_2 \cdot^-$, relative to normal lung epithelium (FIG. 2). This is the first rigorous demonstration of increased $O_2 \cdot^-$ levels in freshly harvested human NSCLC tissues compared to normal tissue and supports the hypothesis that tumor cells have increased steady-state levels of $O_2 \cdot^-$ relative to normal cells.

Pharmacological Concentrations of Ascorbate Increase NSCLC Chemo-Radiation Sensitivity In Vitro.

Figures 3A, 3B:
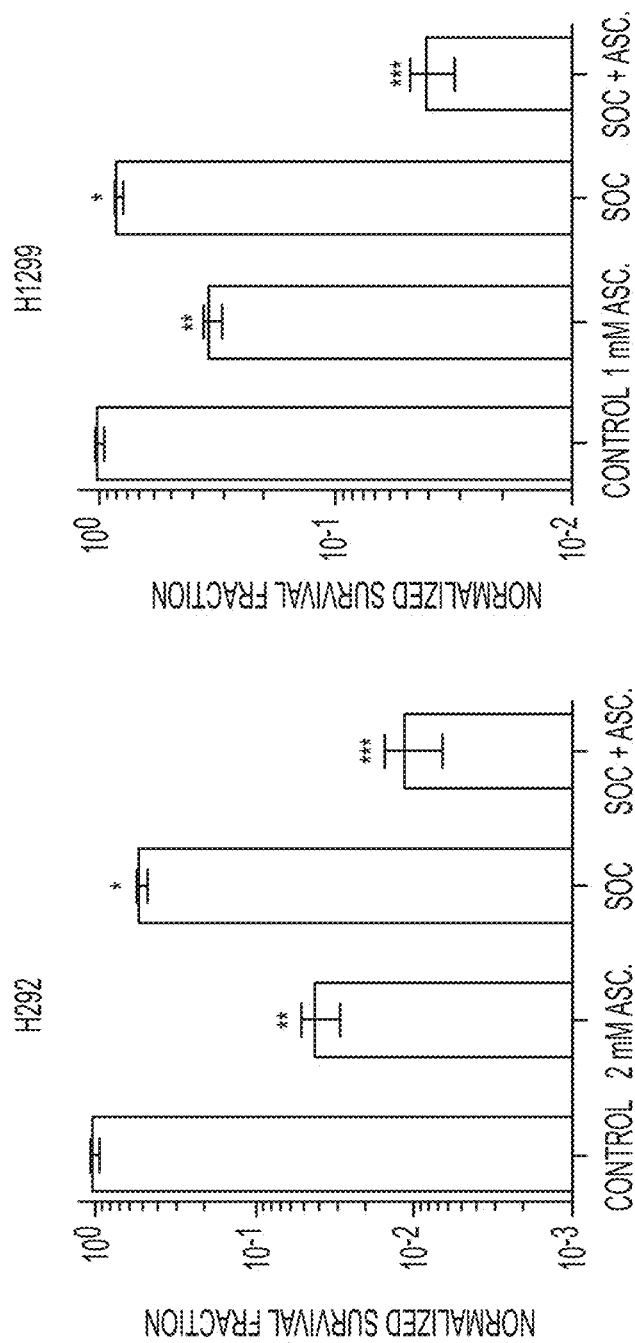
FIGS. 3A-3B. Ascorbate enhances chemo-radiation sensitivity in lung cancer cells, NCI-H292 and H1299 cells in vitro. NCI-H292 (FIG. 3A) and H1299 (FIG. 3B) cells were treated with combinations of 5 μM carboplatin (carbo), 2 Gy radiation (IR) and/or 2 mM ascorbate for 1 h (asc). Clonogenic survival was significantly reduced in cells treated with either asc or carbo+IR+asc compared to cells treated with carbo+IR alone respectively (* and ** $p<0.05$).

To determine if ascorbate increases chemo-radiation sensitivity in human NSCLC cells, NCI-H292 and H1299 cells were grown in vitro and treated with combinations of 1 hr 2 mM ascorbate, 5 µM carboplatin (Carbo), and/or 2 Gy of ionizing radiation (IR). Clonogenic survival analysis found that 2 mM ascorbate significantly increased sensitivity to Carbo+IR in both NCI-H292 cells and H1299 cells (FIGS. 3A, 3B), relative to Carbo+IR alone. Interestingly, a pharmacological dose of ascorbate alone caused more clonogenic cell killing in NSCLC cell lines than chemotherapy plus radiation.

Figure 4:
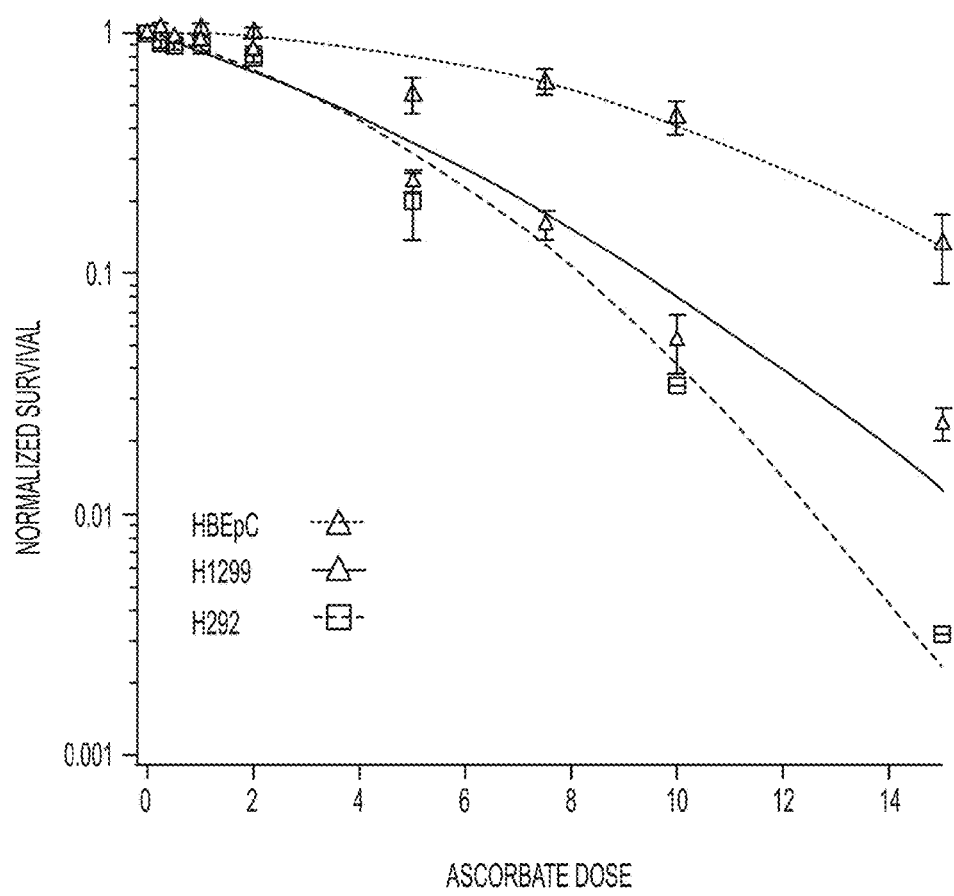
FIG. 4. Normal lung epithelial cells are resistant to ascorbate toxicity. HBEpC lung epithelium cells were exposed to various doses of ascorbate for 1 hour followed by clonogenic survival analysis. HBEpCs were significantly more resistant to pharmacological ascorbate as compared to NSCLC cell lines H292 and H1299.

Normal Lung Epithelial Cells Are Resistant to Pharmacological Doses of Ascorbate To assess the differential sensitivity of normal vs. cancer cells to pharmacological ascorbate, we obtained non-immortalized human lung epithelial cells, HBEpC, and exposed them to increasing doses of ascorbate followed by clonogenic survival analysis. In contrast to NSCLC cells (FIGS. 3A, 3B), increasing doses of pharmacological ascorbate had no effect on normal lung cell clonogenic survival (FIG. 4). These results strongly support the hypothesis that pharmacological doses of ascorbate are selectively toxic to NSCLCs relative to normal lung epithelial cells.

Figure 5:
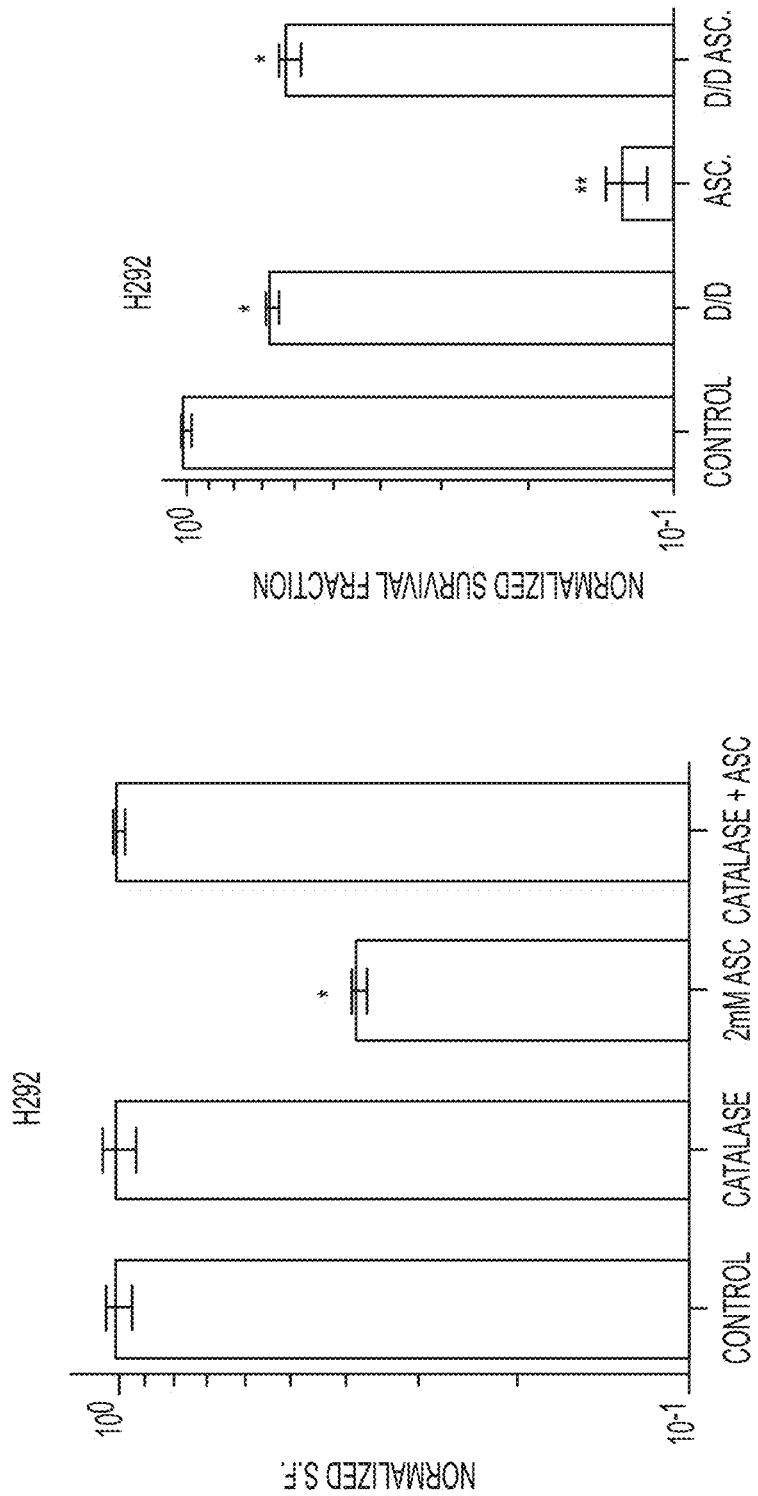
FIGS. 5A-5B: Catalase and metal chelation inhibits ascorbate toxicity.

Pharmacological Ascorbate Toxicity is Mediated by $H_2O_2$ and is Partially Dependent Upon Labile Fe To determine if $H_2O_2$ was responsible for the sensitivity of NSCLC cancer cells to pharmacological ascorbate induced killing, NCI-H292 were exposed to combinations of 2 mM ascorbate and/or polyethylene glycol conjugated (PEG)-catalase which converts $H_2O_2$ into $H_2O$ and $O_2$ with a rate constant of $10^7$ $mol^{-1} sec^{-1}$. Clonogenic survival data (FIG. 5A) show that PEG-catalase inhibited cancer cell killing by ascorbate, strongly supporting the hypothesis that $H_2O_2$ derived from auto-oxidation of ascorbate is responsible for cell killing (FIG. 1).

To assess if redox active metal ions, including $Fe(NO_3)_3$, and $FeSO_4$ found in tissue culture media, contributed to the toxicity of pharmacological ascorbate, NCI-H292 lung cancer cells were treated with ascorbate in the presence and absence of diethylenetriaminepenta-acetic acid (Det) and deferoxamine (Def), which are metal chelators that bind Fe and inhibit redox cycling. These compounds effectively inhibit the ability of metal ions to catalyze the auto-oxidation of ascorbate to produce $H_2O_2$. The results in FIG. 5B show that Det+Def inhibited the toxicity of ascorbate in NSCLC cells. This result supports the hypothesis shown in FIG. 1 that labile redox active metal ions participate in the auto-oxidation of ascorbate forming the $H_2O_2$ responsible for cancer cell killing.

Figure 6:
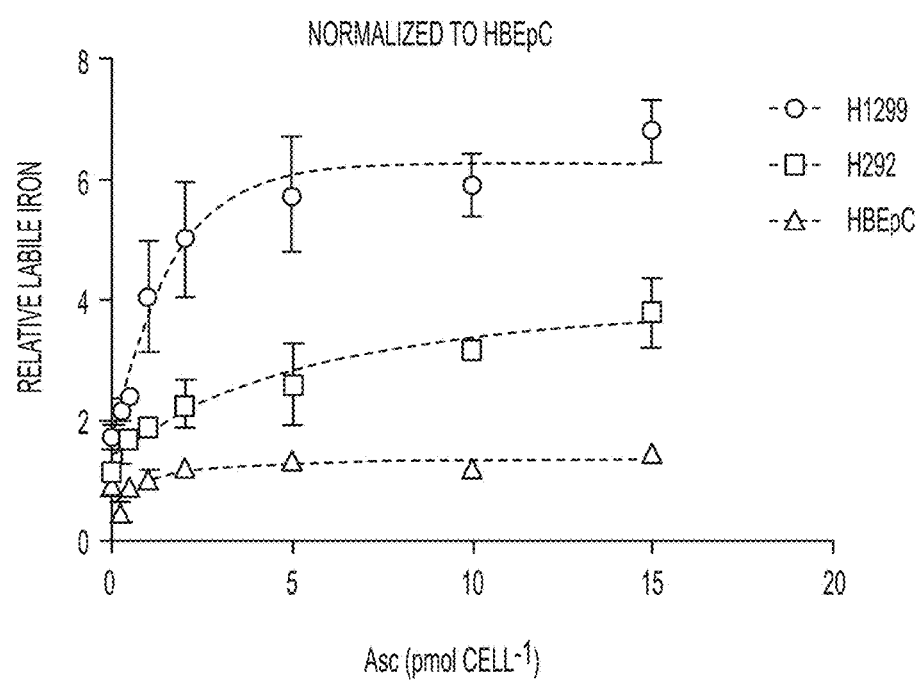
FIG. 6: Lung cancer cells have increased labile iron relative to normal bronchial epithelial cells. Labile Fe was measured in NCI-H292 and H1299 NSCLC cells and normal bronchial epithelial cells (HBEpC) by the fluorescent marker calcein-AM. Mean fluorescence intensity (MFI) was assessed and showed that the NSCLC cells have increased labile Fe relative to normal bronchial epithelium and that this difference is significantly increased in the presence of increasing doses of pharmacological ascorbate.

NSCLC Cells Have Increased Labile Iron Relative to Normal Bronchial Epithelial Cells Intracellular labile Fe in both NCI-H292 and HBEpC was assessed by measuring the changes in the fluorescent Fe chelator molecule, calcein. Fluorescence data demonstrates that the NSCLC cell line, NCI-H292, has significantly more labile Fe, relative to the normal bronchial epithelium cell line, HBEpC (FIG. 6). Similar to the sensitivity to pharmacological ascorbate, the NSCLC cell line, NCI-H292, has significantly increased labile Fe relative to normal bronchial epithelium, HBEpC (mean fluorescence intensity of 2 vs 1 respectively ($p<0.05$).

Figure 7B:
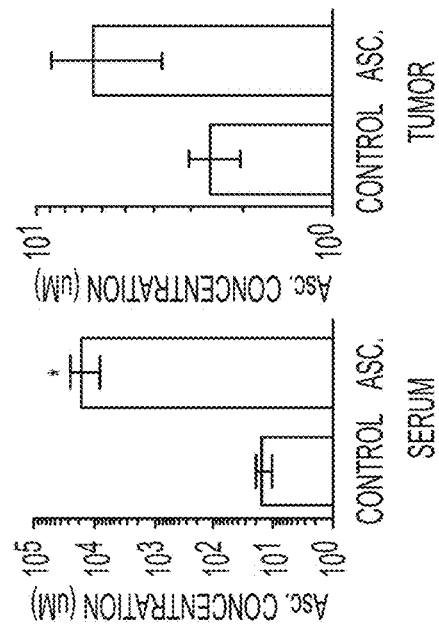
FIGS. 7A-7B. Ascorbate enhances 11292 chemo-radiation sensitivity in vivo.
Figure 7A:
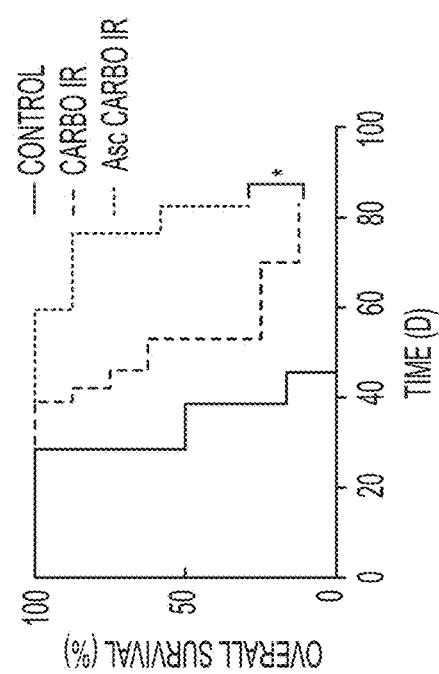

Pharmacological Ascorbate Enhances Chemo-Radiation Sensitivity in an NSCLC Xenograft Model Pharmacological ascorbate was combined with carboplatin and radiation in a NSCLC xenograft model. Nude mice were injected with NCI-H292 cells into their flanks and tumors grown to a diameter of 2-4 mm. Animals were then treated with vehicle control (saline injected IP), daily ascorbate (4 g ascorbate/kg mouse weight IP), chemo-radiation (12 Gy/6fx IR+weekly 15 mg/kg carboplatin), or ascorbate+chemo-radiation. All treatments were well-tolerated as measured by a lack of weight loss (data not shown). Mice bearing xenografts treated with ascorbate+chemo-radiation survived significantly longer than mice treated with chemo-radiation alone (FIG. 7A: right vs. middle line). Two hours following the completion of the last radiation treatment, plasma and tumors were harvested, and ascorbate concentrations were measured in a subset of mice. Mice produce endogenous ascorbate (FIG. 7B); however, ascorbate treated mice had significantly higher plasma and tumor ascorbate concentrations relative to non-ascorbate treated mice (FIG. 7B).

These data support the hypothesis that pharmacological ascorbate is capable of enhancing chemo-radiation sensitivity via an $H_2O_2$-mediated mechanism that is dependent upon the presence of redox active metal ions.

Pharmacological Ascorbate Enhances NSCLC Chemo-Radiation Sensitivity In Vitro by a Mechanism Mediated by Metal Ion Catalyzed $H_2O_2$-Induced Oxidative Stress.

The mechanism underlying ascorbate's selective toxicity to cancer vs. normal cells remains largely unknown. A detailed understanding of this phenomenon provides invaluable insights into the metabolic differences between cancer vs normal cells that can be exploited in the development of pharmacological ascorbate as an adjuvant to lung cancer therapy. Data suggest pharmacological ascorbate's toxicity is directly related to $H_2O_2$ production and at least partly dependent upon the presence of labile Fe (see FIGS. 1 and 5). Previous research demonstrated cells treated with ascorbate release $Fe^{+2}$ from the Fe-binding protein, ferritin, at a ratio of 2 $Fe^{+2}$ per ascorbate molecule with a $K_m=1.3$ mM. (J Cancer Res Clin Oncol. 1994; 120(7):415-21. Ascorbicacid-mediated iron release from cellular ferritin and its relation to the formation of DNA strand breaks in neuroblastoma cells. Baader SL1, Bruchelt G, Carmine T C, Lode H N, Rieth A G, Niethammer D. PMID: 8188735; Boyer R F, Grabill T W, Petrovich R M. Reductive release of ferritin iron: a kinetic assay. Anal Biochem. 1988 October; 174(1): 17-22; Moser J C, Rawal M, Wagner B A, Du J, Cullen J J, Buettner G R. Pharmacological ascorbate and ionizing radiation (IR) increase labile iron in pancreatic cancer. Redox Biol. 2014; 2:22-27). Furthermore, superoxide dismutase (SOD) significantly inhibited $Fe^{+2}$ release from ferritin (Superoxide ion as a primary reductant in ascorbate-mediated ferritin iron release. Boyer R F, McCleary C J. Free Radic Biol Med. 1987; 3(6):389-95). It is proposed that $O_2.^-$ is able to mobilize and release bound Fe into the labile Fe pool ($Fe^{+2}$), which can then undergo redox cycling with $O_2$ and ascorbate to form $H_2O_2$. Hydrogen peroxide can react with $Fe^{+2}$ through Fenton chemistry to form the hydroxyl radical (.OH), which causes oxidative damage to critical biomolecules inducing cancer cell death. Therefore, pharmacological ascorbate may be selectively toxic to cancer cells because cancer cells have increased $O_2.^-$ relative to normal cells.

The $H_2O_2$ and $O_2.^-$ production is quantified in the normal bronchial epithelium cell line, HBEpC, and NSCLC cell lines NCI-H292, H1299 and A549 using spin-trapping, SOD inhibitable DHE oxidation, catalase inhibitable amplex red oxidation assay, and catalase inhibitable DCFH2 oxidation. Based on preliminary data (FIG. 2) and data from other cancer types, NSCLC cells are expected to demonstrate increased steady-state levels of $H_2O_2$ and $O_2.^-$ relative to normal lung epithelial cells. The sensitivity of normal vs. NSCLC cells to oxidative stress induced cell killing by clonogenic survival assay is determined. The oxidation state of thiol redox couples is determined by assessing GSH/GSSG and oxidized to reduced thioredoxin status before and after exposure to radiation, chemotherapy and/or ascorbate. Based on the sensitivity of each cell line to ascorbate, the intracellular Fe concentration is calculated by using Fe chelation approaches with ferric iron as a positive control. Briefly, cells will be washed and incubated in PBS to which the Fe chelators, deferoxamine or 1,10-phenathroline will be added. The Fe-chelator complex may be detected by their absorption at 430 nm and 510 nm respectively. An additional Fe chelation approach is used to measure labile iron that utilizes changes in the fluorescent molecule, calcein. Non-fluorescent cell permeable calcein-acetoxymethyl ester is loaded into cells where it is cleaved by esterases to produce fluorescent non-cell-permeable calcein, whose signal is quenched upon chelation with labile Fe. Addition of a cell-permeable Fe chelator will release the quenched signal, and the intracellular labile Fe concentration will be determined by the change in fluorescence using ferrous iron as the positive control. The sensitivity of the cell lines to pharmacological ascorbate by Fe chelation is modulated to confirm causality.

Determination of Pharmacological Ascorbate Using In Vivo Xenograft Models for Modulating Chemo-Radiation Sensitivity Via Enhancement of Oxidative Stress.

Human NSCLC cell lines, NCI-H292, H1299, and A549, are injected into the flanks of nude mice as described above. Flank xenografts are made because it allows for caliper tumor measurements and also allows for shielding of the body during radiation treatment. Once the tumors reach 2-4 mm in diameter, nine mice are assigned to the following treatment groups: 1) saline (control), 2) ascorbate (4 g/kg) 3) carboplatin (carbo) at 75 mg/kg,[25] 4) radiation (IR) at 12 Gray in 6 fractions over a period of two weeks, 5) carbo+ascorbate, 6) IR+ascorbate, 7) IR+carbo+ascorbate. Tumor size is measured and volumes calculated daily. Following radiation (two weeks), treatment ceases and a random subset (three mice) of tumors and serum are harvested and assessed for measures of oxidative stress parameters including intracellular GSH/GSSG, $NADP^+$/NADPH, and protein carbonyl content via the Protein Carbonyl Assay Kit (Cayman-Chem©) as well as 4HNE-modified protein as a marker for oxidative damage to lipids and proteins. The GSH/GSSG redox couple is the most prevalent thiol redox buffer in cells, and a shift to increasing GSSG content in cancer cells is an excellent marker of oxidative stress-induced cancer killing. The protein carbonyl assay is based on the principle that redox-active metal ions such as $Fe^{3+}$ in the presence of $H_2O_2$ and $O_2.^-$ are able to oxidize amino acids to carbonyls. Carbonyls then interact with dinitrophenylhydrazine (DNPH), forming Schiff bases that can be detected with a spectrophotometer at an absorbance of 360-385 nm. MINE-modified protein is an excellent marker for oxidative damage to both lipids and proteins. The 6 remaining mice are monitored for tumor growth rates, toxicity, and survival. Causal relationships between increased oxidative stress, labile iron, and improved outcomes are confirmed in experiments where mice will be given the thiol antioxidant, N-acetylcysteine or metal chelators such as DETAPAC two hours prior to therapy.

EXAMPLE 2

The use of large doses of vitamin C (ascorbic acid or ascorbate) to treat cancer has been exceptionally controversial since first suggested over four decades ago. A previously unrecognized mechanism through which extremely high levels of EDTA combined with pharmacological ascorbate (vitamin C at very high-doses) can be an effective way to enhance the clonogenic cell killing of human lung cancer cells has been discovered by the present inventors. High levels of EDTA enhance the toxicity of ascorbate via the accelerated generation of $H_2O_2$. Using $^{14}C$ labeled EDTA, it has been discovered, that it is retained with cancer cells following exposure. EDTA need not be present in the cell culture medium to have this effect. Pretreatment followed by washing out the EDTA is sufficient to get enhanced toxicity. Given the resurgence and excitement in using pharmacological ascorbate in combination with standard of care radio-chemotherapy for stage 4 lung cancer patients, the use of EDTA to further enhance therapeutic responses leads to new novel therapeutic insights and drug formulations.

In certain embodiments, the present invention relates to the use of pharmacological ascorbate (vitamin C) in combination with 35-50 mg/m² calcium disodium EDTA concentrations of EDTA to remove loosely bound iron to enhance cancer treatment efficacy. Pharmacological ascorbate in combination with high doses of EDTA appears to increase the anti-cancer effects of ascorbate treatment thereby making the tumor cells more sensitive to standard chemotherapy and/or radiation therapy. This combination may be applied clinically in order to increase efficacy of anti-cancer cell therapy by both medical and radiation oncologists.

Pharmacological ascorbate is currently being assessed in a variety of aggressive cancers (such as non-small cell lung cancer) and thus the applications as an anti-cancer agent are broadly applicable clinically. The effects appear to be specific to cancer cells due to differences in cancer cell vs. normal cell metabolism.

High dose EDTA combined with pharmacological ascorbate and standard-of-care chemotherapy decreases clonogenic cell survival in two non-small cell lung cancer cell lines compared to standard of care radio-chemotherapy alone.

Figure 8:
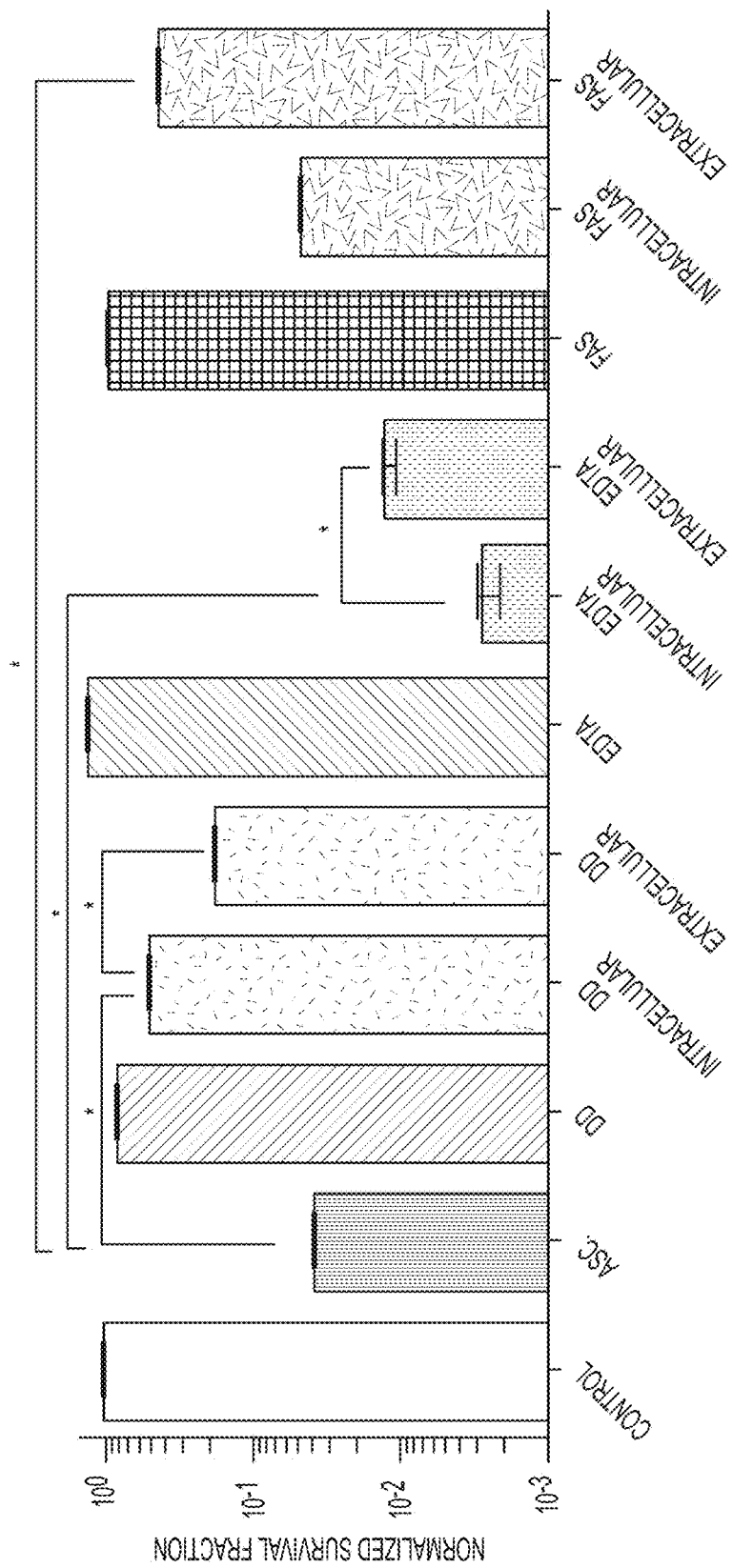
FIG. 8. Lung cancer cells treated with ascorbate and iron chelators effect ascorbate toxicity. Chelates that inhibit redox cycling of iron (D/D: desferrioxamine, DETAPAC) protect cancer cells from ascorbate toxicity and chelates that enhance iron redox cycling (EDTA) enhance responses to cancer therapy (*p<0.05).

In both tissue culture and mouse models of cancer, pharmacological ascorbate combined with standard of care treatment (chemotherapy and radiation therapy) increased tumor cell killing significantly compared to current standard of care treatment regimens alone (FIG. 8). This new usage of high dose EDTA as a metal chelator to enhance redox cycling of metal ions for cancer therapeutics allows for enhanced effects of ascorbate when combined with radio-chemotherapies in lung cancer.

The combination of two relatively non-toxic treatments that have both been shown to be well-tolerated in humans to enhance the efficacy of radiochemotherapy for stage IV lung cancer is very unexpected and different from any other medical use of EDTA.

Patients being treated with pharmacological ascorbate receive large doses intravenously several times a week for several weeks, or months. The amount of ascorbate needed to achieve the ideal therapeutic dose varies considerably from patient to patient, but in combination with high dose EDTA enhances the anti-tumor efficacy and reduce the variability in effective dosing.

EXAMPLE 3

Multiple myeloma is diagnosed in approximately 28,000 people in the US each year and is the cause of death in approximately 13,000 cases. It is the second most common hematologic malignancy after non-Hodgkin's lymphoma. Major progress has been made in the treatment of myeloma with the combination of autologous transplantation and the newer drugs such as IMDs and proteasome inhibitors, resulting in a median survival of 12 years with the most intensive approaches such as Total Therapy III. However, at least 50% of patients will relapse and need effective salvage therapy. The outcome of relapsed myeloma patients is still poor and new treatment modalities are urgently needed for those patients. Again, one potential approach with minimal additional and may be reduced toxicity that exploits fundamental differences in oxidative metabolism between cancer cells and normal cells is pharmacological dosing of ascorbate. There is good rational for the combination of ascorbate with a proteasome inhibitor at a higher dose (carfilzomib 56 mg/m$^2$ every week) and with high-dose melphalan as a pre-transplant preparative regimen to induce strand breaks in addition to the crosslinks caused by the high dose melphalan. In the setting of multiple myeloma (MM), carfilzomib 56 mg/m$^2$ every week or melphalan (200 mg/m$^2$, reduced to 140 mg/m$^2$ for patients ≥70 years old or with a creatinine ≥2 mg/dl).

Low Expression of FPN1 is Linked to Poor Survival in Multiple Myeloma

Figure 9A:
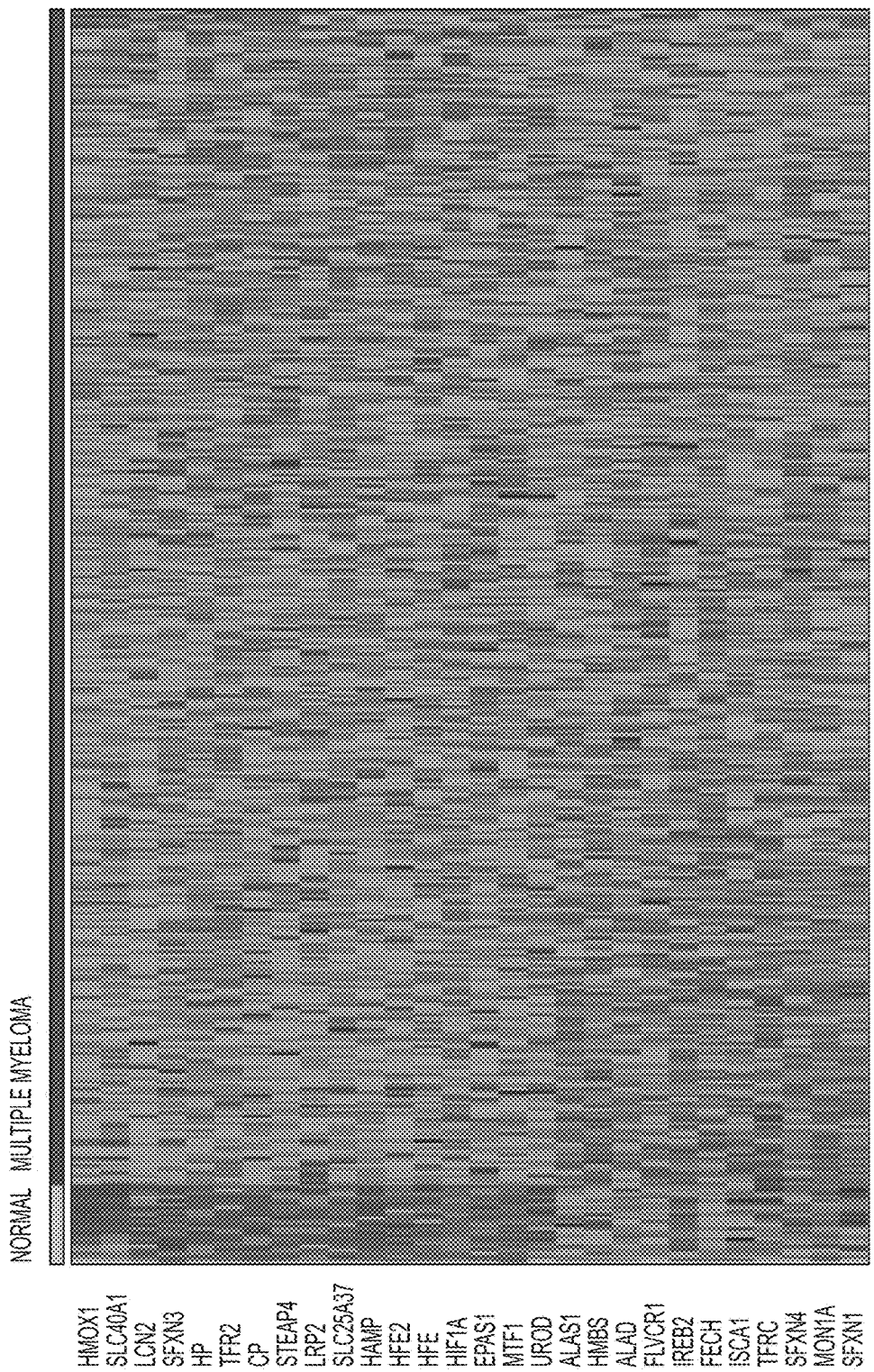
Figure 9B:
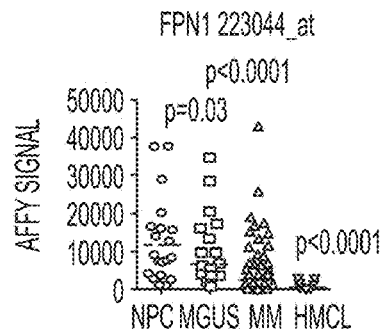
Figure 9C:
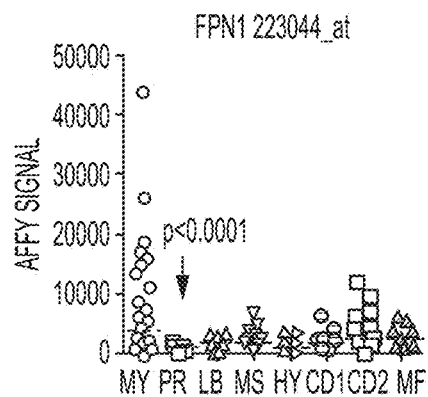
Figure 9D:
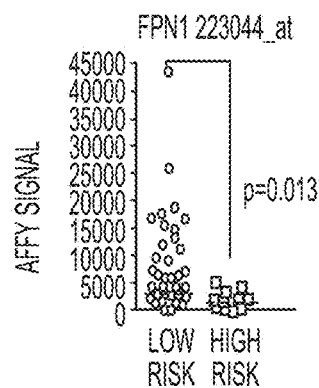
Figure 11:
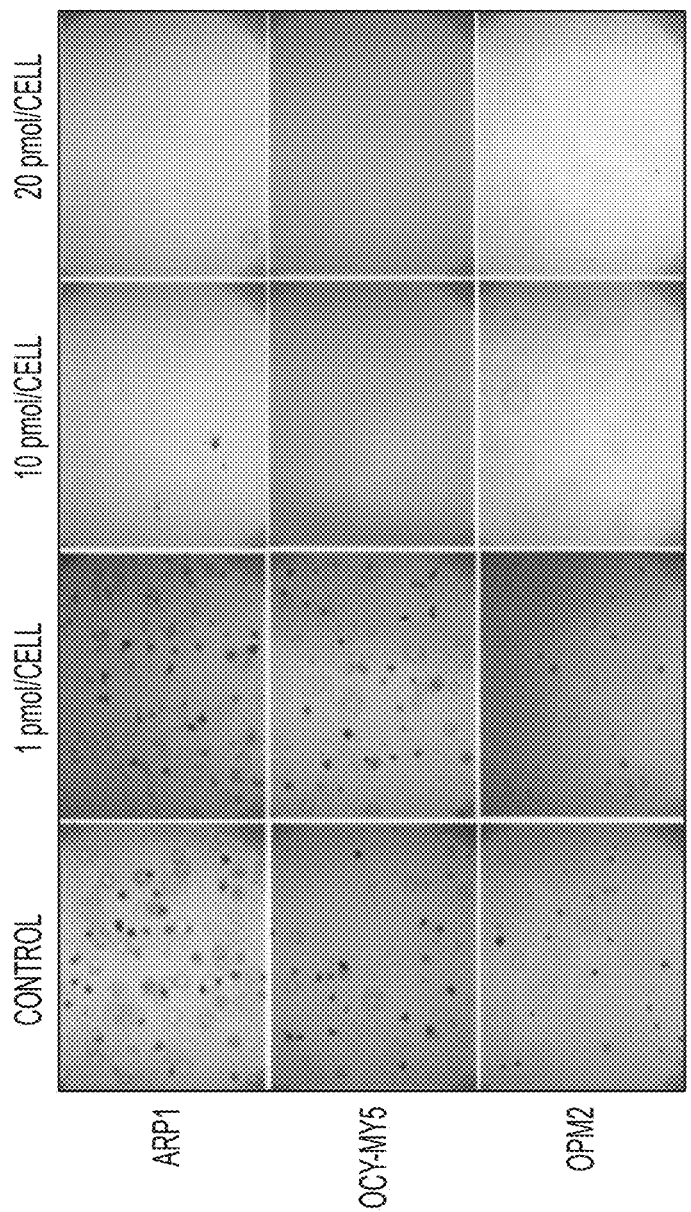
FIG. 11. Pharmacological ascorbate inhibits clonogenesis of myeloma cells. Three myeloma cell lines ARP1, OCI-MY5, and OPM2 were treated for 1 hour at indicated concentration of ascorbate and then subjected to clonogenic assay. Colony formation of cancer cells in soft agar after a 1-h treatment with differentiation of ascorbate. Colony formation was presented by comparing with matched untreated control cells.

To evaluate iron regulation in multiple myeloma cells, we reanalyzed our previous gene expression profiling data containing 22 NPC samples and 351 newly diagnosed multiple myelomas from the Total Therapy 2 (TT2) cohort using the Affymetrix U133Plus 2 platform. Of the 61 signature genes related to iron metabolism (131 probe sets), we identified 29 genes significantly dysregulated by comparison of NPC versus multiple myeloma samples (P<0.005; ratio ≥1.5-fold). A supervised hierarchical cluster in FIG. 9A showed clearly that a subset of multiple myeloma patients have 18 genes downregulated and 11 genes upregulated in multiple myeloma. These include iron-importing genes, IREB2 and TFRC, and iron-exporting gene, FPN1. We then correlated the expression of these 29 genes with patient outcome in the TT2 cohort, FPN1, the only vertebrate iron exporter, was found to be the top gene whose downregulation in multiple myeloma was associated with an inferior outcome (OS: P=0.0032). Because FPN1 had a dysregulated expression and was associated with poor survival, we explored its functional role in multiple myeloma. We also evaluated the expression of FPN1 in sequential multiple myeloma samples from the same patient, in the different genetic subgroups and in the different risk-related subtypes. FPN1 expression was significantly lower in PCs derived from multiple myeloma patients compared with PCs derived from patients with monoclonal gammopathy of undetermined significance (MGUS) and healthy donors (P<0.0001, FIG. 9B). We also found that expression of FPN1 had the lowest expression in the proliferation subgroup (PR), which is the subgroup with the poorest prognosis (P<0.0001; FIG. 9C), and was significantly lower in the high-risk group compared with the low-risk group based on our 70-gene model (P=0.013; FIG. 9D). We performed survival analyses in three different datasets. Consistent with the low FPN1 expression in the aggressive multiple myeloma subgroups, decreased FPN1 in the 351 TT2 cohort showed that about 60% of such cases showed short EFS (FIG. 9E; P<0.001) and also inferior OS (P<0.001; FIG. 9F). The correlation of low FPN1 with inferior patient outcome was further validated in two other independent cohorts, including 270 newly diagnosed multiple myeloma enrolled in the HOVON-65 clinical trial (FIG. 9G) and 264 relapsed myeloma patients enrolled in the APEX phase III clinical trial (FIG. 9H; ref 32).

FPN1 Regulates Intracellular Iron In Vitro and In Vivo in Multiple Myeloma Cells.

To test whether FPN1 regulates iron exportation in multiple myeloma cells, the labile iron pool (LIP) was measured with fluorescent metallosensor calcein. ARP1 and OCI-MY5 cells overexpressing FPN1 had lower LIP compared with their EV counterparts (FIG. 10A). We further employed 5TGM1-KaLwRij model to test the role of FPN1 on multiple myeloma progression in vivo. Real-time PCR confirmed that 5TGM1 myeloma cells had much lower expression of FPN1 than normal bone marrow plasma cells in KaLwRij mice (FIG. 10B). The coding region of FPN1 cDNA in a doxycycline-inducible lentiviral construct was stably transduced into the 5TGM1 cells with lentivirus, in which the expression of FPN1 could be induced upon addition of doxycycline (FIG. 10C). One week after transduced 5TGM1 cell injection, mice were administrated doxycycline and dextran-iron to increase systemic iron content in the mouse body as previously reported. In the absence of dextran-iron, overexpression of FPN1 (activated by administration of doxycycline) significantly delayed tumor progression evidenced by decreased tumor burden measured by mouse serum IgG2b level (FIG. 10D; P=0.008) and prolonged survival (FIG. 10E; P<0.001) compared with non-induced (no doxycycline) group. Addition of iron accelerated tumor progression of the 5TGM1 mice, resulting in a shorter survival and higher tumor burden than those without iron in drinking water (FIG. 10E; P=0.009); the effect of iron administration on multiple myeloma progression could be blocked by activation of FPN1 expression (FIGS. 10D and E).

Pharmacological Ascorbate Inhibits Colony Formation in Myeloma Cells.

For colony formation on soft agar plates, three myeloma cell lines ARP1, OCI-MY5 and OPM2 were treated with 1 pmol/cell, 10 pmol/cell, and 20 pmol/cell ascorbate for 1 h, washed, and plated. A two-layer agar system was used, and colonies were visualized after 10-14 days. As shown in FIG. 10, all three myeloma cell lines exposed to ascorbate displayed completely growth inhibition at 10 pmol/cell or higher.

Pharmacological Ascorbate Decreases Myeloma Tumor Growth Rate In Vivo.

Figure 12:
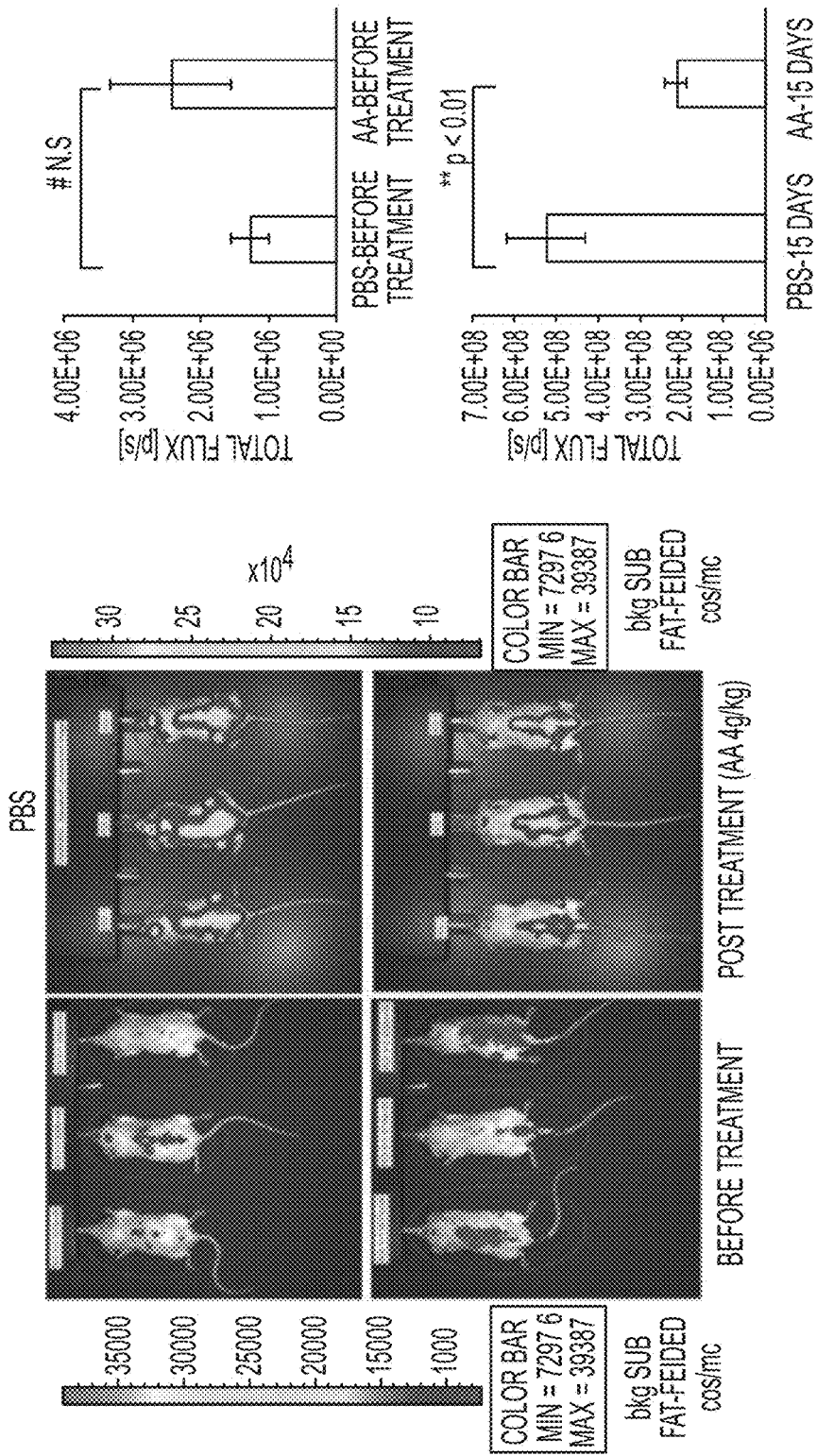
FIG. 12. Pharmacological ascorbate inhibits myeloma cell growth in vivo. Mice bearing ARP1 labeled with luciferase myeloma cells were treated with ascorbate (4 g/kg, daily IP). The results show a significant decrease of tumor growth for mice treated with ascorbate (p<0.01).

We evaluated if pharmacological ascorbate inhibits myeloma tumor growth in vivo using two different xenograft models (FIG. 12). The first model used is a luciferase labeled human myeloma cell line ARP1. About 1.3 M ARP1 myeloma cells were injected into the NOD-SCID mice intravenously, IVIS showed clearly myeloma cells engrafted into mice with similar tumor burden between the control and treatment groups (N.S.) after injection 1 week (left panel FIG. 12). We started to treat these mice (n=3/group) with ascorbate 4 g/kg approximately 15 days. Our results show that a daily administration of ascorbate significantly decreased tumor growth rate. At the end of the treatment, mean tumor fluorescent intensity is 5.24×108 flux (p/s) in the control group versus 2.15×108 flux (p/s) for the ascorbate-treated group, which means a significant decrease of 59% ($p<0.01$) (right panel FIG. 12).

This experiment was repeated in a tumor-bearing mouse model through IP injection of ARP1 myeloma cells, which allows a solid tumor growth when implanted in mice purpose. A total of 106 ARP1 MM cells (in 50 µl PBS) per mouse were injected into NOD-SCID mice through IP. Mice (n=3) were treated with ascorbate 4 g/kg approximately 15 days. Ascorbate induced decrease in final tumor volumes (50±30 mm3 versus 180±80 mm3, for ascorbate-treated and control mice, respectively) (data not shown). This result further support that pharmacologic concentrations of ascorbate inhibit myeloma tumor growth.

EXAMPLE 4

O2.$^-$ and $H_2O_2$-Mediated Disruption of Fe Metabolism Causes the Differential Susceptibility of Lung and Brain Cancer Cells to Pharmacological Ascorbate Pharmacological ascorbate has been proposed as a potential anti-cancer agent when combined with radiation and chemotherapy. The anti-cancer effects of ascorbate are hypothesized to involve the auto-oxidation of ascorbate leading to increased steady-state levels of $H_2O_2$; however, the mechanism(s) for cancer cell-selective toxicity remain unknown. The current study shows that alterations in cancer cell mitochondrial oxidative metabolism resulting in increased levels of $O_2.^-$ and $H_2O_2$ are capable of disrupting intracellular iron metabolism thereby selectively sensitizing lung (NSCLC) and brain cancer (GBM) cells to ascorbate through pro-oxidant chemistry involving redox active labile iron and $H_2O_2$. In addition, both preclinical studies and clinical trials demonstrate the feasibility, selective toxicity, tolerability, and potential efficacy of pharmacological ascorbate in GBM and NSCLC therapy.

Despite advances in treatment strategies, 5-year overall survival in NSCLC and GBM has not significantly increased over the last 20 years. Here, we demonstrate that pharmacological ascorbate represents an easily implementable and non-toxic agent that may increase treatment efficacy when combined with standard-of-care radio-chemotherapy in NSCLC and GBM. Furthermore, the mechanism by which ascorbate is selectively toxic to cancer cells versus normal cells is shown to involve alterations in redox active iron metabolism mediated by mitochondrial $O_2.^-$ and $H_2O_2$. As fundamental defects in oxidative metabolism leading to increased steady-state levels of $O_2.^-$ and $H_2O_2$ emerge as targetable hallmarks of cancer cells, the current findings support a generalized mechanism for the application of pharmacological ascorbate in cancer therapy.

Introduction

Intravenous pharmacological doses of ascorbate have recently re-emerged as a potential anti-cancer therapy with clinical trials in ovarian and pancreatic cancer subjects demonstrating tolerability with similar or reduced toxicities, relative to chemotherapy alone (Ma et al., 2014; Monti et al., 2012; Welsh et al., 2013). Preclinical studies with ascorbate have consistently demonstrated cancer cell-selective cytotoxicity in a variety of disease sites (Du et al., 2010; Ma et al., 2014; Riordan et al., 1995). Although the mechanism(s) of selective toxicity remain unknown, mounting evidence suggests that ascorbate toxicity is dependent on ascorbate's action as a pro-drug for hydrogen peroxide ($H_2O_2$) generation (Chen et al., 2005, 2007; Olney et al., 2013).

Interestingly, both $H_2O_2$ toxicity and ascorbate oxidation forming $H_2O_2$ are dependent upon metal ion redox chemistry (Buettner and Jurkiewicz, 1996; Du et al., 2015; Halliwell and Gutteridge, 1990). Furthermore, there is increasing evidence that perturbations in cancer cell oxidative metabolism result in increased steady-state levels of reactive oxygen species (ROS), including superoxide ($O_2.^-$) and $H_2O_2$ (Bize et al., 1980; Szatrowski and Nathan, 1991; Spitz et al., 2000; Aykin-Burns et al., 2009), and that these species may be capable of disrupting cellular iron metabolism leading to increased LIP levels (Caltagirone et al., 2001; Ibrahim et al., 2013; Pantopoulos et al., 1997). Indeed, many cancer cells exhibit disruptions in iron metabolism with up-regulation of several iron-uptake pathways, such as transferrin receptor (TfR) protein, as well as down-regulation of iron export and storage pathways (Torti and Torti, 2013).

The current study demonstrates that pharmacological ascorbate selectively sensitizes non-small cell lung cancer (NSCLC) and glioblastoma multiforme (GBM) cells to radiation and chemotherapy, relative to normal lung and brain cells, due to differential metabolism of intracellular redox-active metal ions mediated by increased levels of $O_2.^-$ and $H_2O_2$. In addition, a phase I clinical trial in GBM as well as preliminary results from a phase II NSCLC clinical trial demonstrate easily achievable therapeutic levels of plasma ascorbate, no serious adverse events attributable to ascorbate when combined with standard-of-care therapies, and promising results for increasing treatment efficacy. Together, these results support the hypothesis that pharmacological ascorbate combined with standard-of-care therapies may represent a novel approach in the management of NSCLC and GBM that targets cancer cell-specific alterations in redox active iron metabolism.

Results

Figure 13A:
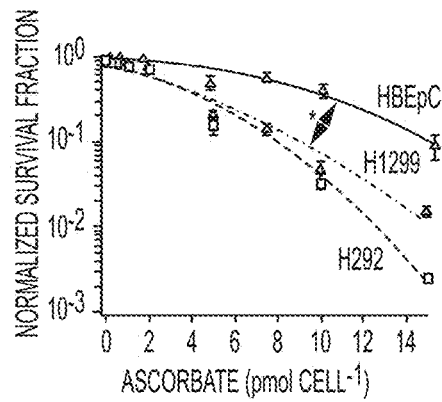
FIGS. 13A-13H. Ascorbate selectively sensitizes NSCLC and GBM cells to chemo-radiation in vitro as compared to normal cells.
Figure 13B:
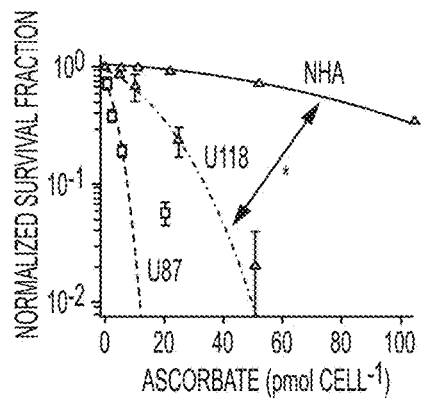
Figure 13C:
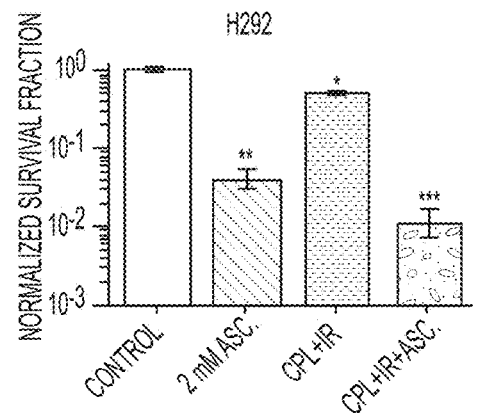
Figure 13D:
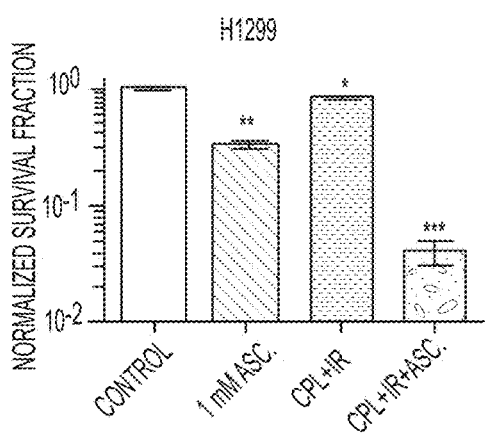
Figure 13E:
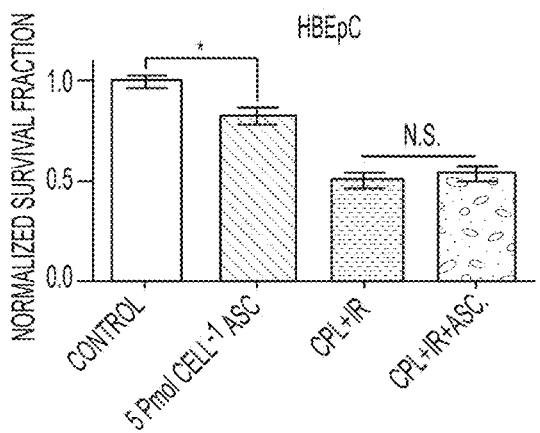
Figure 13F:
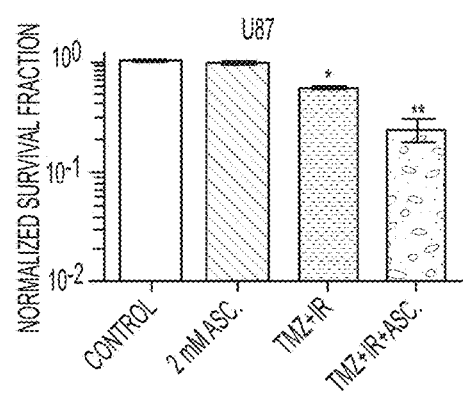
Figure 13G:
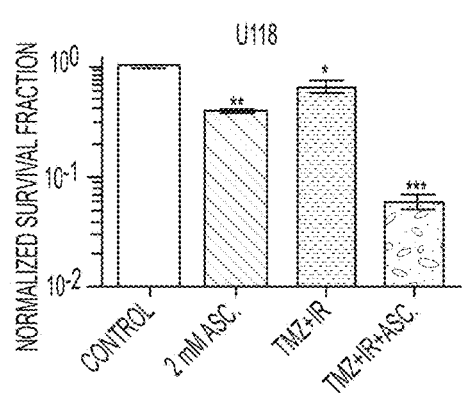
Figure 13H:
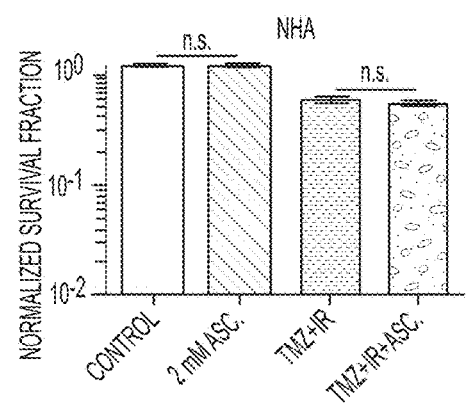

Pharmacological Ascorbate Selectively Sensitizes NSCLC and GBM Cells, as Compared to Normal Cells, to Radio-Chemotherapy The efficacy of ascorbate in preclinical NSCLC and GBM models was assessed using clonogenic survival assays and murine xenografts. Tumor versus normal cell ascorbate comparisons (pmol cell$^{-1}$) were performed in identical media preparations due to the proposed dependence of ascorbate toxicity on $H_2O_2$, cell density, and media constituents including pyruvate, metal ions, pH, and serum (Olney et al., 2013; Spitz et al., 1987; Buettner, 1988; Nath et al., 1995; Clément et al., 2001; Mojić et al., 2014; Doskey et al., 2015). Exposure of NSCLC cells (H292 and H1299), and GBM cells (U87 and U118) to increasing concentrations of ascorbate demonstrated dose-dependent clonogenic cell killing (FIGS. 13A, 13B). In comparison, ascorbate was significantly less toxic to normal human bronchial epithelial primary cells (HBEpCs) and normal human astrocytes (NHAs) (FIGS. 13A, 13B; p<0.0001). Furthermore, ascorbate selectively sensitized NSCLC and GBM cells, but not HBEpC and NHA, to IR (2 Gy) combined with chemotherapy [5 μM carboplatin (CPL) or 25 μM temozolomide (TMZ), respectively] (FIGS. 13C-H).

Figure 14A:
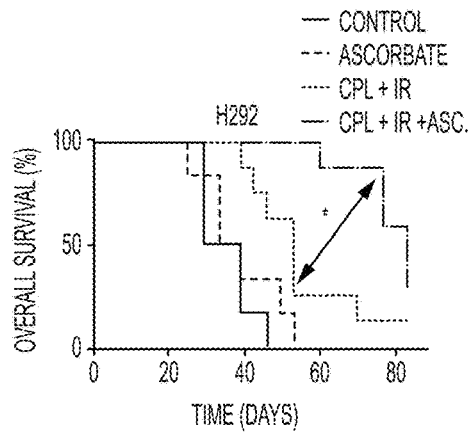
FIGS. 14A-14G. Ascorbate is safe and efficacious in combination with radio-chemotherapy for the treatment of NSCLC and GBM cells in vivo.
Figure 14B:
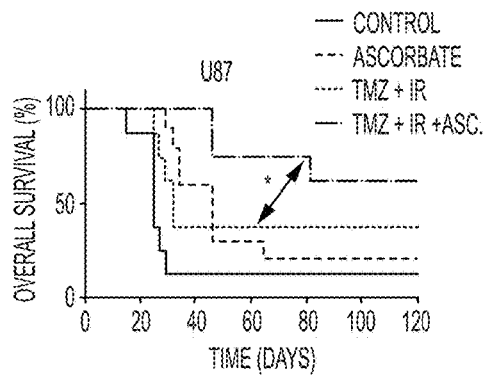
Figure 14C:
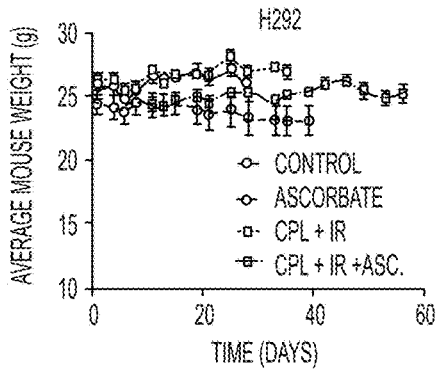
Figure 14D:
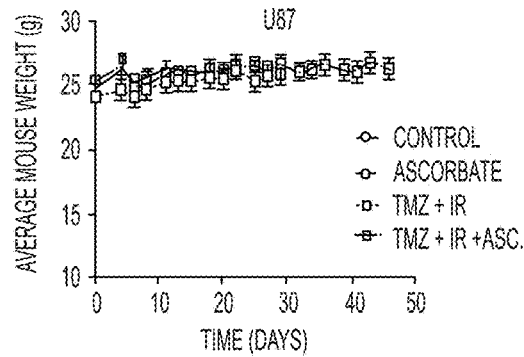
Figure 14E:
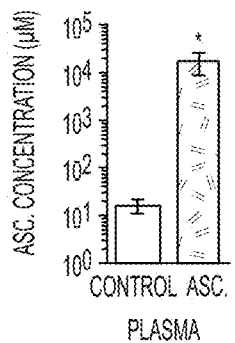
Figure 14F:
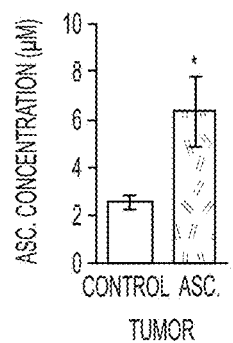
Figure 14G:
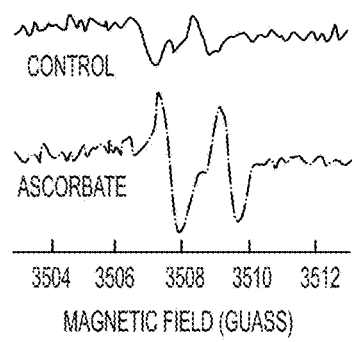

In vivo xenograft studies demonstrated ascorbate [4 g $kg^{-1}$ intraperitoneal injection (IP) daily] combined with radiochemotherapy (12 Gy IR/2 fractions; weekly 15 mg $kg^{-1}$ CPL for H292 or 2.5 mg $kg^{-1}$ TMZ for U87 xenografts IP) significantly increased overall survival (FIGS. 14A, 14B). Ascorbate treatment was well tolerated as monitored by mouse weight (FIGS. 14C, 14D), and IP delivery significantly increased ascorbate levels in the plasma, tumor, and cerebrospinal fluid (FIGS. 14E-G). These data establish the tolerability and efficacy of pharmacological ascorbate in preclinical models of NSCLC and GBM and support the existence of an intrinsic mechanism of selective ascorbate toxicity in cancer vs. normal cells.

Figure 15A:
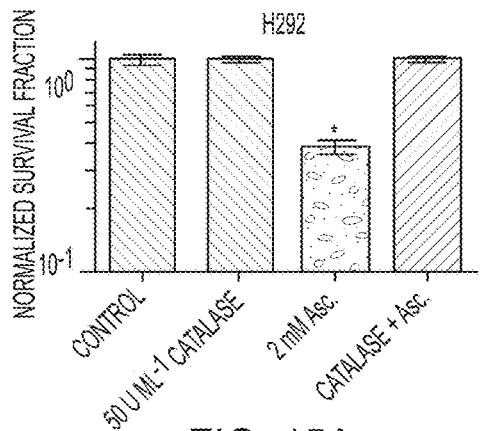
FIGS. 15A-15I. The combination of $H_2O_2$ and redox-active labile iron is necessary and sufficient for ascorbate toxicity. See also Figure S1.
Figure 15B:
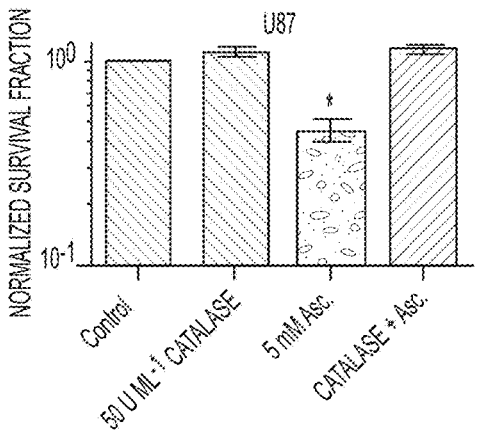
Figure 15C:
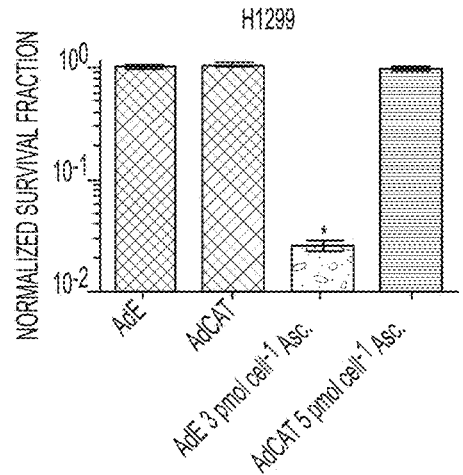
Figure 15D:
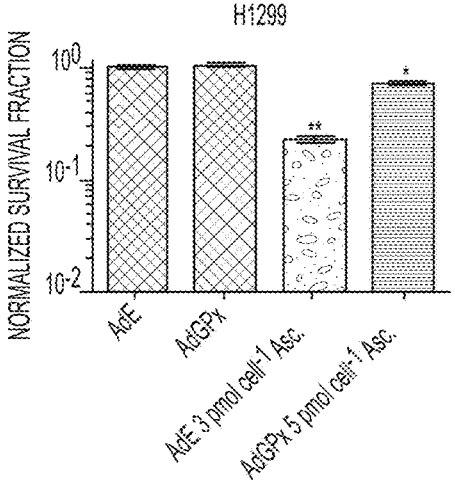
Figure 15E:
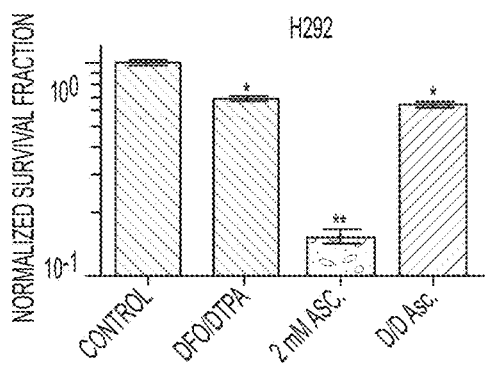
Figure 15F:
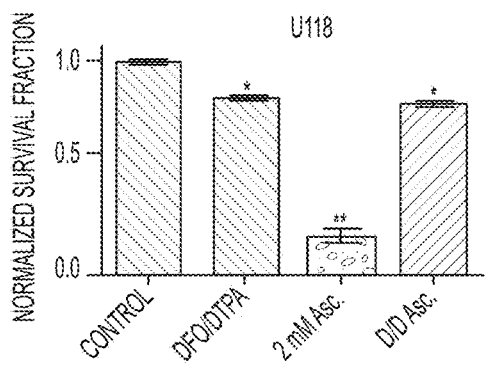
Figure 15G:
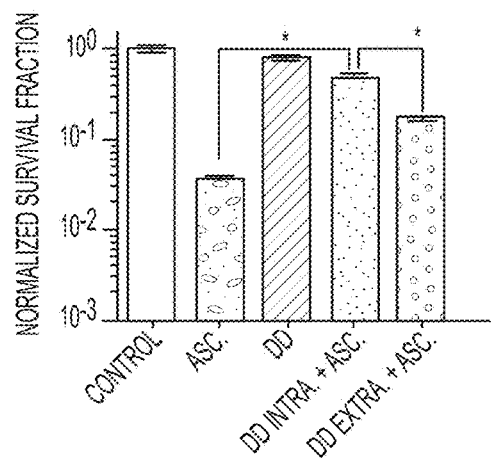
Figure 15H:
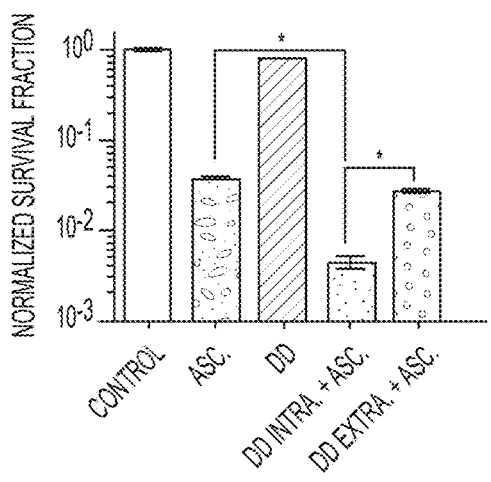
Figure 15I:
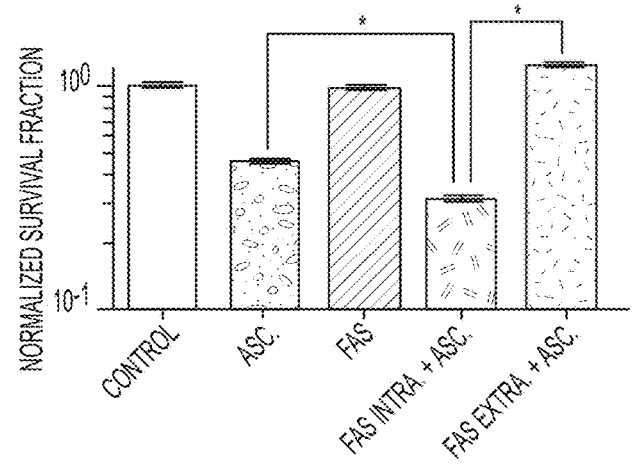
Figure 21A:
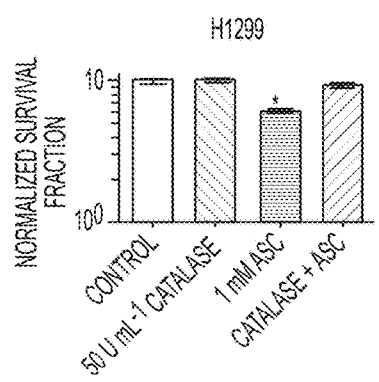
FIGS. 21A-21D. (Related to FIGS. 15A-15I) The combination of $H_2O_2$ and redox-active labile iron is necessary and sufficient for ascorbate toxicity in all NSCLC and GBM cell lines tested.
Figure 21B:
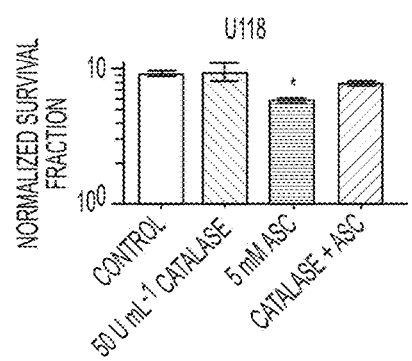
Figure 21C:
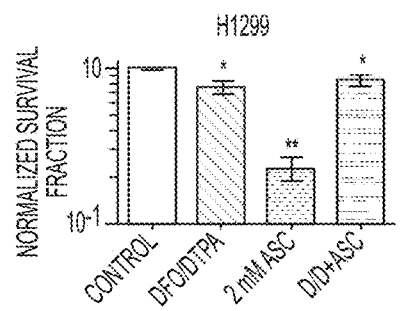
Figure 21D:
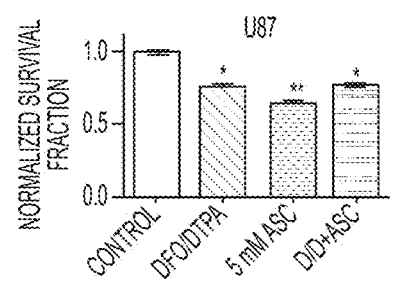

Ascorbate Toxicity is Dependent on the Intracellular Reactions of $H_2O_2$ and Redox-Active Labile Iron Confirming the generality of the previously reported dependence of ascorbate toxicity on the generation of $H_2O_2$ in GBM and NSCLC (Chen et al., 2005, 2007; Olney et al., 2013) ascorbate toxicity was inhibited by exogenous catalase addition, adenoviral-mediated overexpression of catalase, or adenoviral-mediated overexpression of glutathione peroxidase 1 (GPx1) (FIGS. 15A-D; FIGS. 21A, 21B). As both $H_2O_2$ toxicity and ascorbate oxidation forming $H_2O_2$ are dependent upon metal ion redox chemistry (Buettner and Jurkiewicz, 1996; Du et al., 2015; Halliwell and Gutteridge, 1990) it follows that ascorbate toxicity may be dependent on intra-cellular pro-oxidant metal ion chemistry, as has previously been suggested in breast and prostate cancer (Verrax and Calderon, 2009). Indeed, chelators that inhibit redox cycling of iron (desferrioxamine, DFO; diethylenetriaminepentaacetic acid, DTPA) (Buettner, 1986) significantly inhibited ascorbate toxicity in both NSCLC and GBM cell lines (FIGS. 15E, 15F; FIG. 21C, 21D). To further test the role of redox active metal ions, H292 cells were pre-incubated with DFO/DTPA or ethylenediaminetetraacetic acid (EDTA; known to enhance metal redox cycling) (Buettner, 1986) and washed prior to ascorbate treatment or chelators were added to the cells only during ascorbate exposure, providing conditions in which the chelators were either primarily intracellular or extracellular during ascorbate exposure. Intracellular DFO/DTPA inhibited ascorbate toxicity while intracellular EDTA enhanced ascorbate toxicity relative to control or extracellular chelators (FIGS. 15G, 15H). Additionally, increasing the intracellular labile iron pool (LIP) with exogenous $Fe^{2+}$ as ferrous ammonium sulfate (FAS) sensitized cancer cells to ascorbate demonstrating that the LIP determines ascorbate susceptibility (FIG. 15I). These results support the hypothesis that the combination of $H_2O_2$ and intracellular redox-active metal ions is necessary and sufficient for ascorbate toxicity and suggest that differences in cellular iron metabolism may mediate the mechanism of cancer cell selective ascorbate toxicity.

Figure 16A:
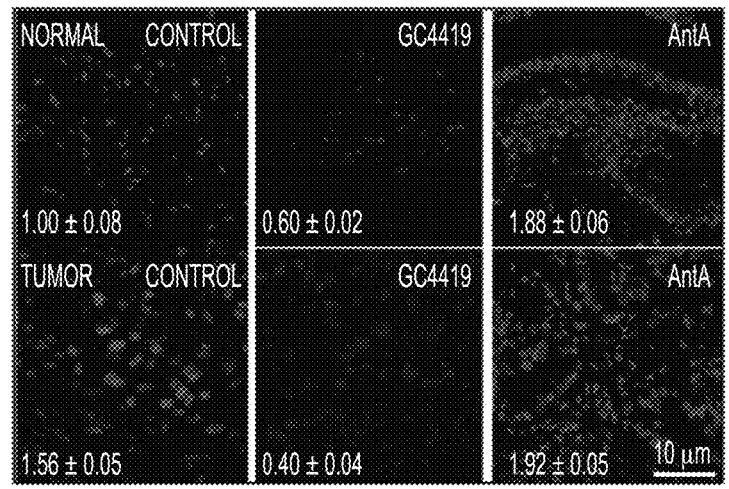
FIGS. 16A-16Q. Disturbances in cancer cell oxidative metabolism disrupt cellular iron homeostasis increasing the LIP and sensitizing cancer cells to ascorbate. See also Figures S2, S3.
Figure 16B:
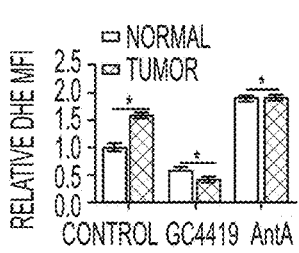
Figure 16C:
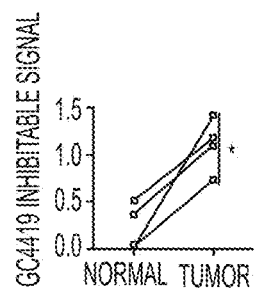
Figure 16D:
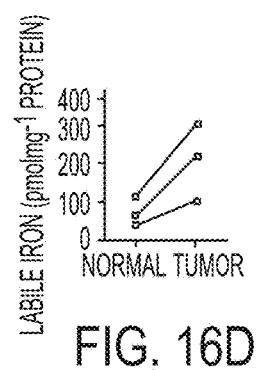
(FIGS. 16D, 16E) NSCLC and adjacent normal tissue was assayed for labile iron content by EPR quantification of the high spin state $Fe^{3+}$-DFO complex (g=4.3, 100
Figure 16E:
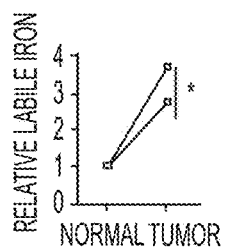
Figure 16F:
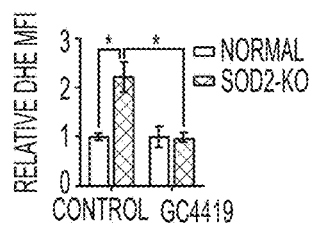
(FIG. 16F) Levels of DHE oxidation in WT HEL 92.1.7 and SOD-2 KO daughter cells at baseline and after pre-incubation with 2.5 µM SOD mimetic GC4419 for 72 h.
Figure 16G:
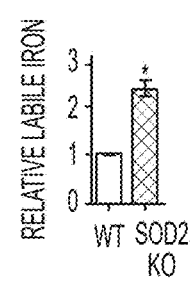
(FIG. 16G) The baseline cellular LIP of HEL 92.1.7 and daughter SOD2-KO cells were quantified using Calcein-AM by flow cytometry and normalized to the parental cell line.
Figure 22:
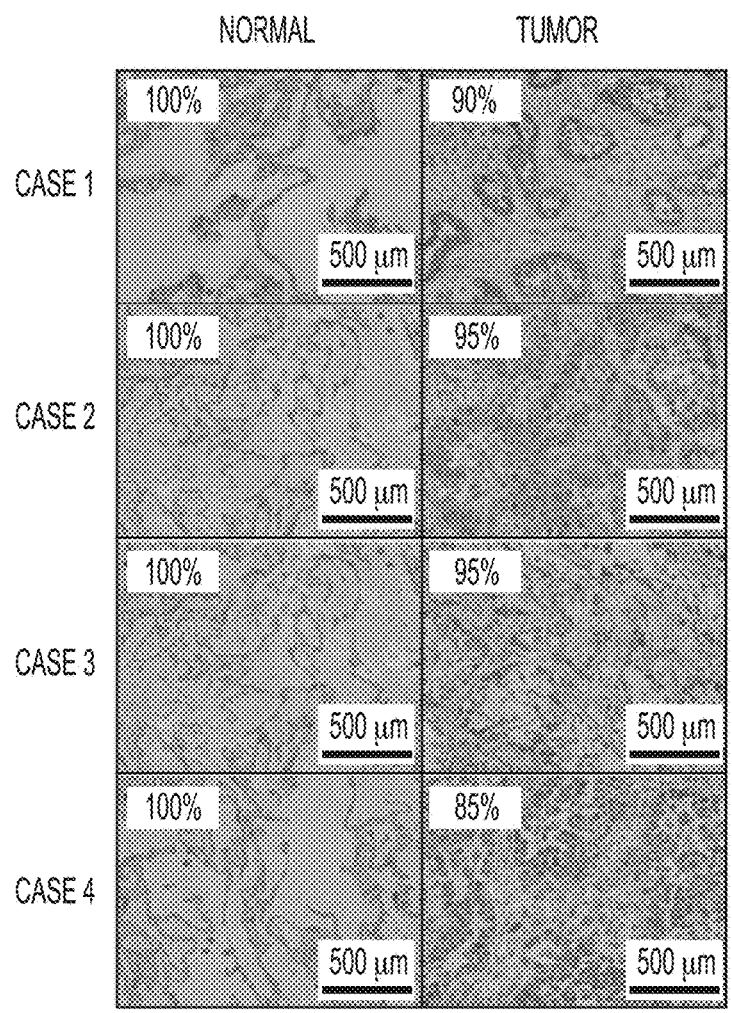
FIG. 22. (Related to FIGS. 16A-16Q) Histological confirmation of NSCLC and adjacent normal tissue sections. H&E staining of NSCLC tissue and adjacent normal tissue used for histological confirmation of NSCLC diagnosis and to determine tumor or normal constitution of samples (%) by a board certified pathologist.
Figure 23A:
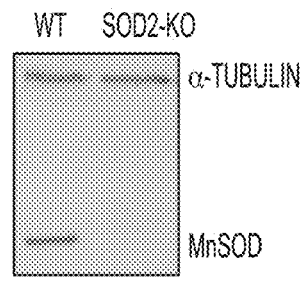
FIG. 23A-23C. (Related to FIGS. 16A-16Q) CRISPR/Cas9-mediated deletion of mitochondrial SOD2 in HEL 92.1.7 cells increases intracellular steady-state levels of ROS.
Figure 23B:
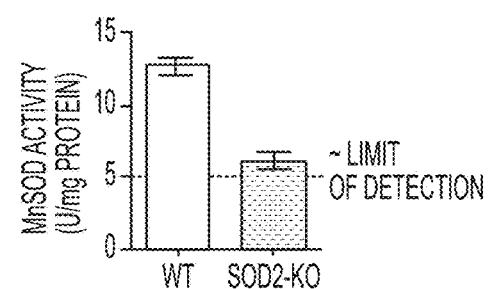
Figure 23C:
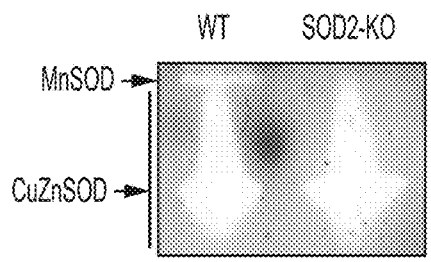

Disturbances in Cancer Cell Oxidative Metabolism Sensitizes to Ascorbate Through Disruptions in Iron Metabolism There is a growing body of literature demonstrating that disruptions in cancer cell oxidative metabolism results in increased steady-state levels of reactive oxygen species (ROS), including superoxide ($O_2.^-$) and $H_2O_2$, which have been hypothesized to disrupt cellular iron metabolism leading to increased LIP levels (Bize et al., 1980; Spitz et al., 2000; Aykin-Burns et al., 2009; Caltagirone et al., 2001; Ibrahim et al., 2013; Pantopoulos et al., 1997; Szatrowski and Nathan, 1991). Supporting this hypothesis, fresh frozen NSCLC tissue from patients demonstrate increased steady-state levels of $O_2.^-$, as determined by superoxide dismutase (SOD) mimetic (GC4419)-inhibitable dihydroethidium (DHE) oxidation (FIGS. 16A-C; FIG. 22), as well as increased labile iron (FIGS. 16D, 16E; FIG. 22) compared to adjacent normal tissue. This supports the hypothesis that increased steady-state levels of $O_2.^-$ may lead to increased LIP that could sensitize cancer cells to ascorbate in human tissues (McCarty and Contreras, 2014). To directly test this hypothesis, the CRISPR/Cas9 system was utilized to delete the mitochondrial superoxide dismutase gene, SOD2, in HEL 92.1.7 human erythroleukemia cells (SOD2-KO) resulting in increased steady-state levels of $O_2.^-$ (FIG. 16F; FIG. 23). SOD2-KO cells demonstrated significantly increased LIP and susceptibility to pharmacological ascorbate-induced clonogenic killing that was inhibited by pre-incubation with DFO/DTPA (FIGS. 16G-I). These results demonstrate that increased steady-state levels of $O_2.^-$ are capable of disrupting cellular iron metabolism, increasing the LIP, and sensitizing cancer cells to ascorbate-induced cell killing.

Furthermore, many cancer cell types exhibit disruptions in iron metabolism with up-regulation of several iron-uptake pathways as well as down-regulation of iron export and storage pathways (Torti and Torti, 2013). Consistent with results from a large immunohistochemical study demonstrating increased TfR levels in NSCLC tissue as compared to adjacent normal lung tissue (Kukulj et al., 2010), NSCLC and GBM cell lines demonstrated increased transferrin receptor (TfR) levels compared to HBEpCs or NHAs, respectively (FIGS. 16J, 16K). Paradoxically, in cancer cells increased TfR is seen in the context of increased labile iron content (FIGS. 16D, 16E). Further supporting the role of increased $O_2.^-$ in disruption of iron metabolism in cancer cells, SOD2-KO cells demonstrated increased TfR protein levels compared to WT parental cells (FIG. 16L). Importantly, siRNA knockdown of TfR significantly decreased the cellular LIP and protected H1299 cells from ascorbate toxicity, demonstrating that these changes in iron metabolism modulate ascorbate-induced cell killing (FIGS. 16M-O).

Figure 16Q:
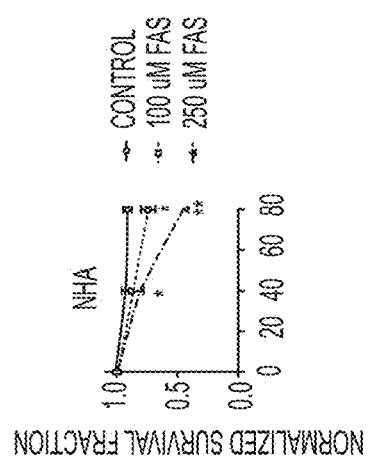
Figure 16P:
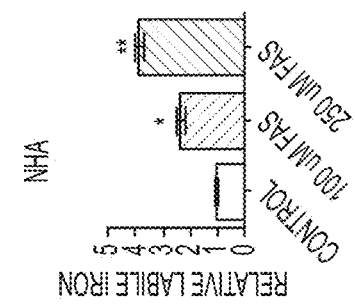
(FIG. 16P) NHAs exposed to 100 µM or 250 µM FAS for 3 h prior to LIP quantification by Calcein-AM flow cytometry or (FIG. 16Q) washed with PBS before exposure to ascorbate for 1 h in fresh full media and then plated for clonogenic survival. For all in vitro studies, n≥3. Data are represented as mean±SEM. *,** represents significant difference, at least p<0.05.
Figure 16O:
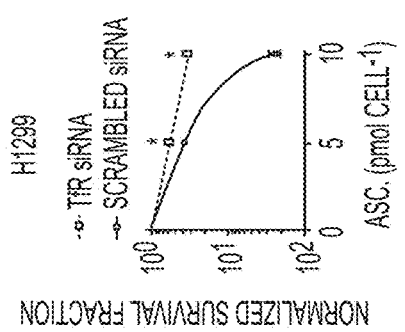
(FIG. 16O) Clonogenic survival of H1299 cells treated with 25 pmol scrambled or TfR siRNA per dish post 1 h exposure to ascorbate.
Figure 16N:
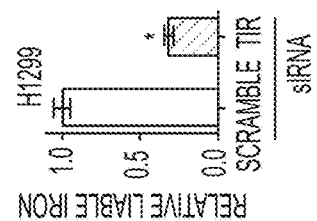
(FIG. 16N) Basal LIP in H1299 cells treated with 25 pmol scrambled or TfR siRNA per dish.

Consistent with the claim that a lower LIP in normal cells limits ascorbate toxicity, exposure of NHAs to FAS increases the LIP (FIG. 16P) and sensitizes NHAs to ascorbate toxicity (FIG. 16Q). Together, these data support the conclusion that cancer-cell specific disruptions in iron metabolism, as a result of perturbed oxidative metabolism, increases the intracellular LIP and significantly contributes to the differential sensitivity of human lung and brain cancer cells to ascorbate toxicity.

Figure 17A:
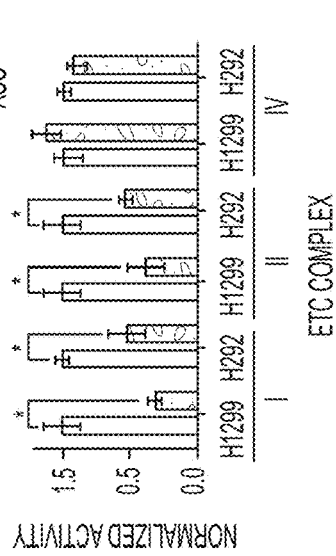
Figure 17B:
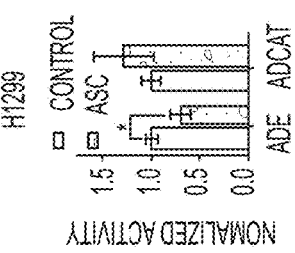
Figure 17C:
(FIGS. 17C-17E) Quantification of total cellular (FIG. 17C) aconitase or (FIGS. 17D, 17E) ETC Complex I and II activity after exposure to 15 pmol cell$^{-1}$ ascorbate for 1 h in NSCLC cell lysates of control cells or H1299 NSCLC cells overexpressing AdE or AdCatalase (50 MOI).
Figure 17D:
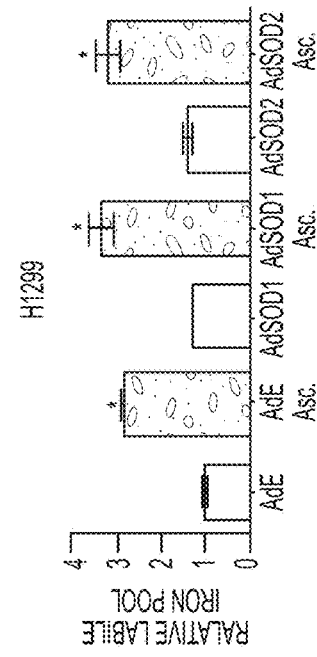
Figure 17E:
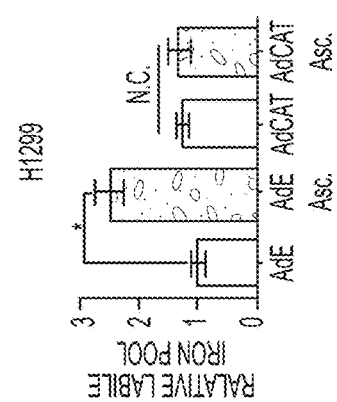
Figure 17F:
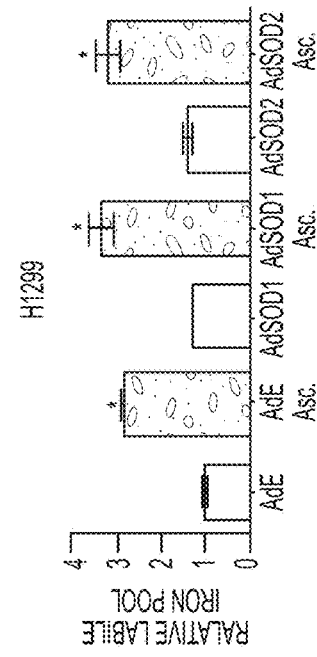
(FIGS. 17F, 17G) Quantification of the cellular LIP of H1299 cells overexpressing an empty vector or (FIG. 17F) catalase (50 MOI) or (FIG. 17G) SOD1 and SOD2 as assayed by Calcein-AM by flow cytometry.
Figure 17G:
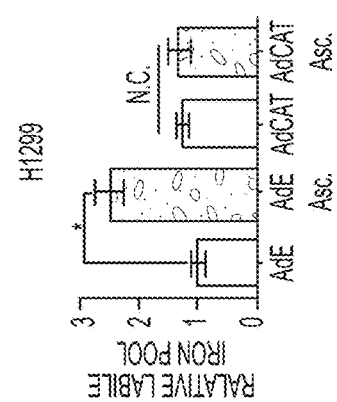

Ascorbate Selectively Increases Cancer Cell LIP Through $H_2O_2$-Mediated Disruptions of Fe—S Containing Proteins In addition to basal differences in labile iron, NSCLC and GBM cells demonstrated significant dose-dependent ascorbate-induced increases in cellular LIP that were not seen in HBEpCs or NHAs. (FIGS. 17A, 17B). This finding was consistent with previous ex vivo studies using ferritin as well as pancreatic cancer xenograft lysates (Boyer and McCleary, 1987; Moser et al., 2014) showing that ascorbate labilized iron from ferritin (Ft), via $O_2.^-$. In intact cells, inactivation of Fe—S cluster protein activity (i.e. aconitase and mitochondrial electron transport chain (ETC) complexes I/II) may be capable of contributing to ascorbate-mediated increases in LIP (FIGS. 17C, 17D). In contrast, ETC complex IV, which contains no Fe—S clusters, showed no inhibition of activity with ascorbate (FIG. 17D). The loss of Fe—S protein activity as well as the increased LIP seen in ascorbate-treated cancer cells was prevented by catalase overexpression (FIG. 17C, 17E, 17F) but not SOD1 or SOD2 (FIG. 17G), demonstrating $H_2O_2$ as the causative agent in ascorbate-induced increases in LIP. In addition, upon exposure to ascorbate (15 pmol cell$^{-1}$) steady-state levels of $H_2O_2$ (as measured by the $H_2O_2$ sensitive fluorescent probe PeroxyOrange-1) significantly increased from baseline in NSCLC cells while remaining unchanged in HBEpCs, a phenomenon not seen with genuine 100 µM $H_2O_2$ (FIGS. 17H-J, FIG. 24). Consistent with LIP redox cycling contributing to ascorbate toxicity in cancer cells, adenoviral mediated overexpression of Ft heavy chain (Ft-H), but not Ft light chain (Ft-L; lacks ferroxidase activity required for iron storage), significantly inhibited basal and ascorbate-induced increases in LIP as well as toxicity (FIGS. 17K-N).

Figure 18A:
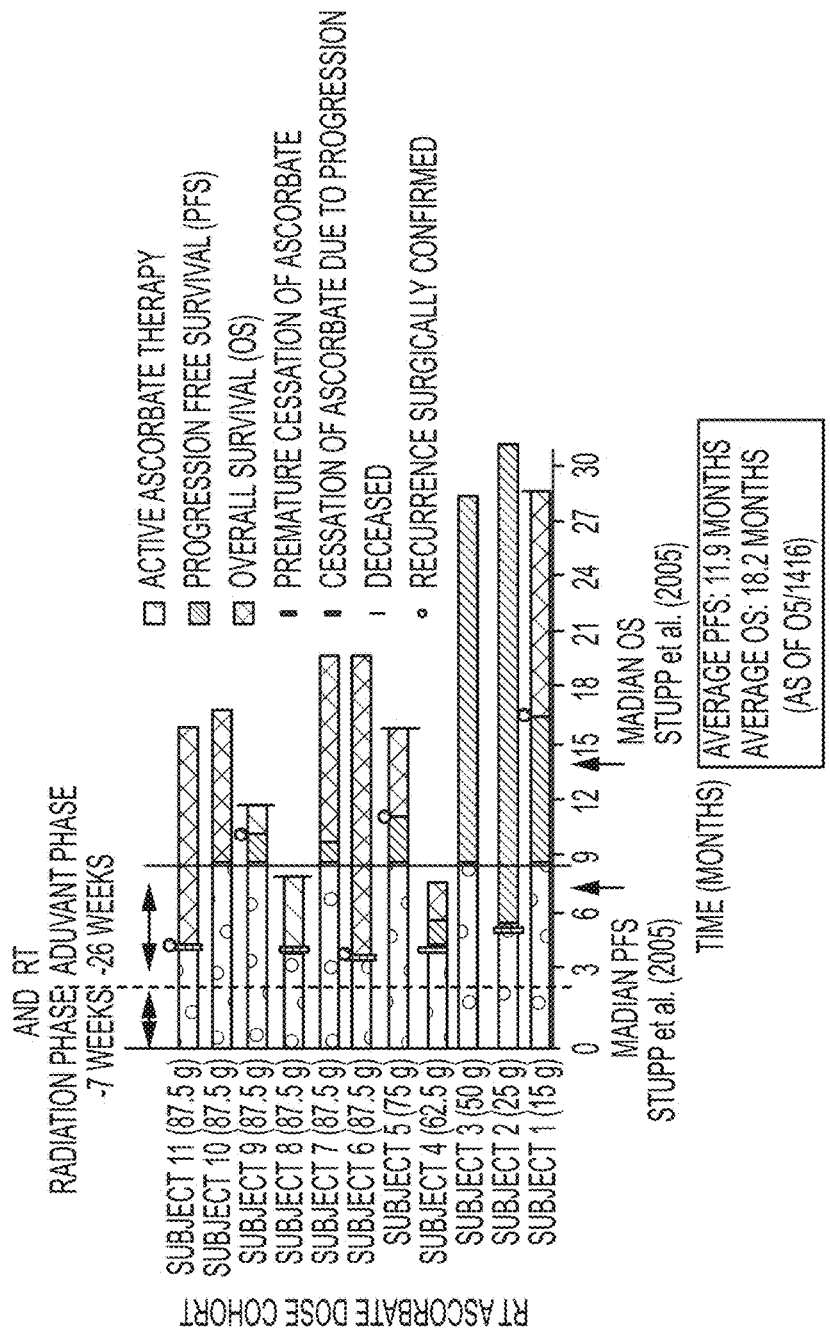
FIGS. 18A-18E. Pharmacological ascorbate is safe and well tolerated when combined with standard therapy in the treatment of GBM and NSCLC. See also Figure S5, Tables S1-4.
Figure 18B:
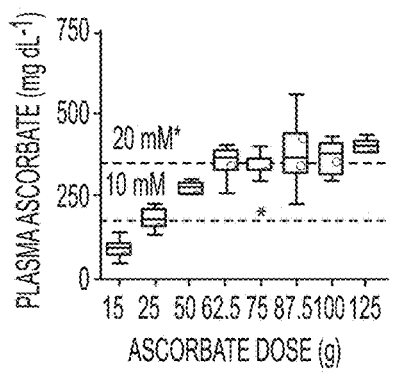
Figure 18C:
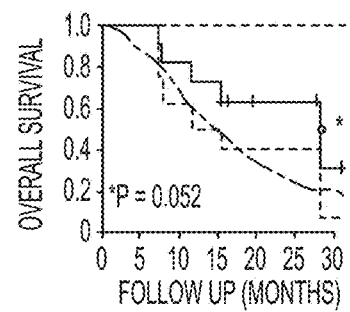
Figure 18D:
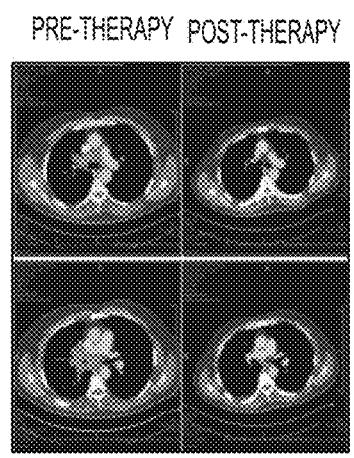
Figure 18E:
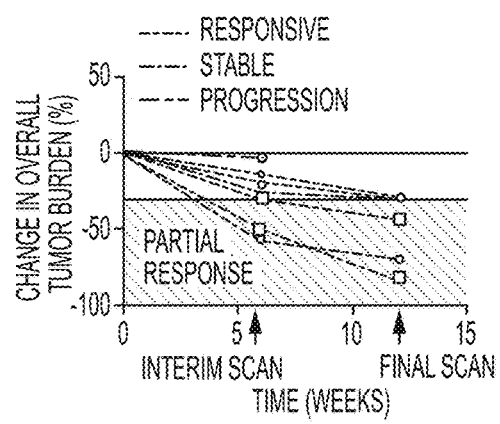
Figure 25A:
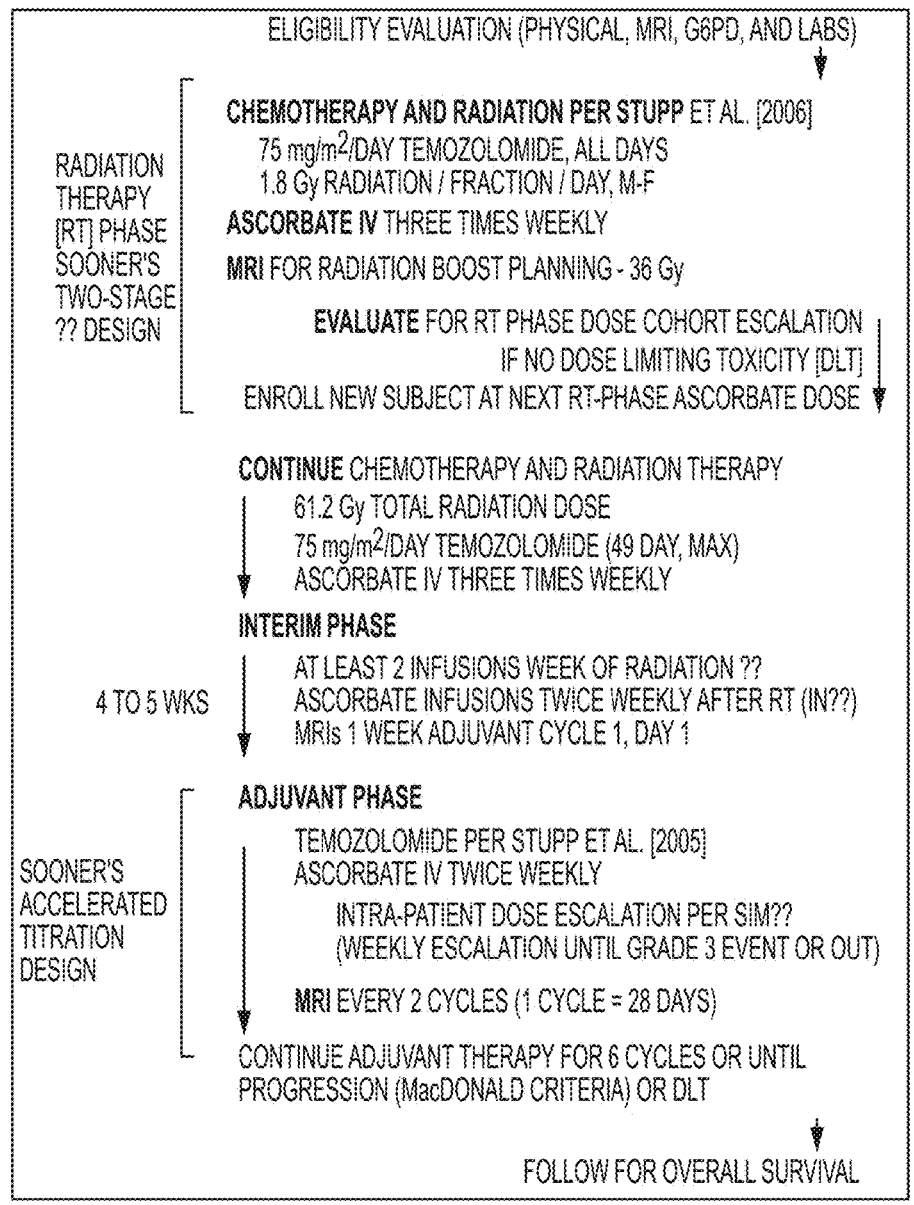
FIGS. 25A-25B. (Related to FIGS. 18A-18E, FIGS. 26-29) Clinical trial schemas.
Figure 25B:
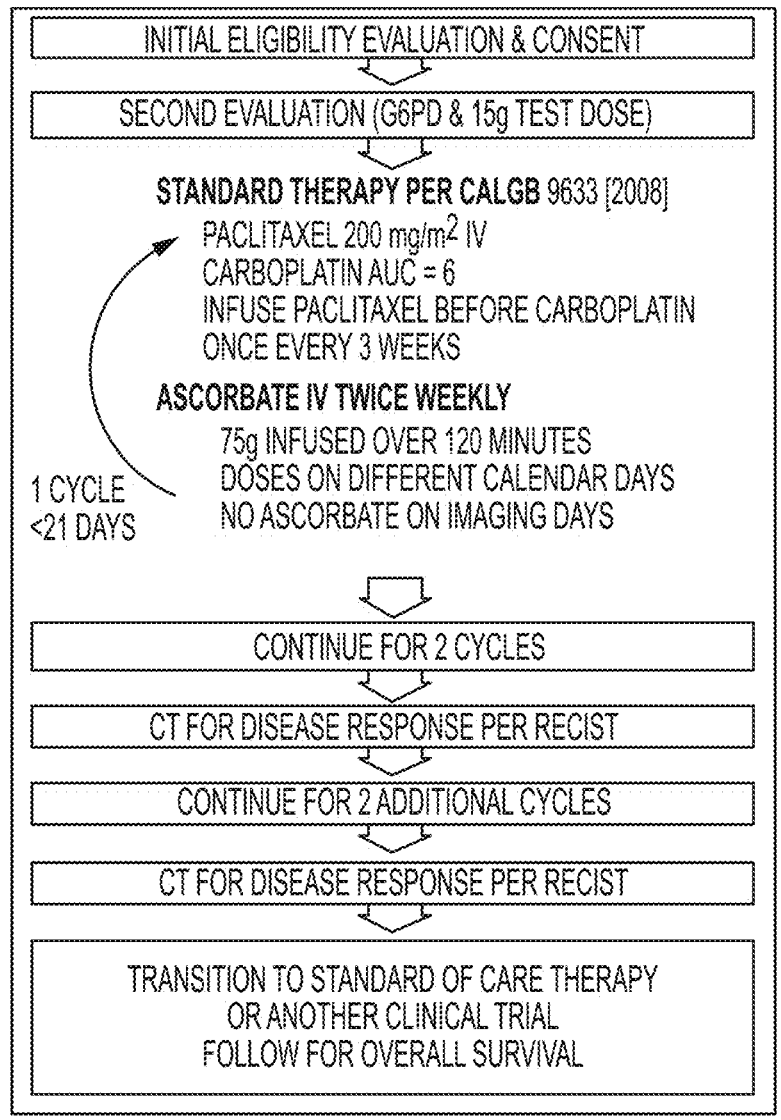

Pharmacological Ascorbate is Safe, Tolerable, and Potentially Efficacious in Combination with Radio-Chemotherapy in GBM and Advanced Stage NSCLC The preclinical studies in GBM led to a phase I clinical trial assessing the safety and tolerability of pharmacological ascorbate in combination with IR and TMZ in GBM subjects (NCT 01752491) (FIG. 25A; FIG. 26). Following maximal resection or biopsy (if unresectable), subjects received radiation (daily), temozolomide (daily), and intravenous (IV) ascorbate infusions (three times a week) for approximately 7 weeks (radiation phase). This was followed by the adjuvant phase where subjects received ascorbate twice a week with temozolomide for approximately 28 weeks (FIG. 18A) (Stupp et al., 2005). Ascorbate doses were escalated during the radiation phase for each subject (15-125 g/infusion) with a ≥20 mM target plasma concentration (Welsh et al., 2013). The desired therapeutic blood level was achieved in all subjects receiving the 87.5 g infusions (FIG. 18C). Pharmacological ascorbate was safe and well tolerated in all 13 subjects who participated in the trial with minimal grade 3 and 4 toxicities (FIGS. 27, 28). Although the small number of subjects prevent a statistically significant assessment of efficacy (11 subjects; 2 subjects were removed from longevity analysis due to limited protocol dictated therapy due to background disease), average progression free survival (PFS) currently stands at 11.9 months (median: 9.4 months) vs. the historical median PFS of 7 months (Stupp et al., 2005), and average overall survival (OS) is currently 18.2 months (current median: 16.5 months; estimated median overall survival: 28.4 months) vs. historical median of 14 months, with 7 subjects remaining alive (FIG. 18A). Furthermore, the initial results from a phase II clinical trial assessing the efficacy of pharmacological ascorbate with platinum-doublet chemotherapy in advanced stage NSCLC (NCT 02420314) also demonstrate promising results in achieving therapeutic ascorbate blood levels (16.4±0.5 mM) and achieved a disease control rate of 83% and an objective response rate of 67%, as compared to historical controls with 15-19% objective response rates (FIGS. 18D-E; FIG. 25B; FIG. 29) (Schiller et al., 2002; Sandler et al., 2006).

Discussion

Pharmacological doses of ascorbate were first used by Cameron and Pauling in 1976, where they demonstrated a four-fold increase in survival in subjects with a variety of terminal cancers [10 g day$^{-1}$ IV followed by 10 g PO day$^{-1}$] (Cameron and Pauling, 1976). Unfortunately, two randomized clinical trials testing the efficacy of high-dose oral ascorbate failed to demonstrate any effect on survival as compared to placebo and the field stalled (Creagan et al., 1979; Moertel et al., 1985). However, subsequent pharmacokinetic studies have demonstrated the inability of oral ascorbate dosing to reach therapeutic plasma levels (Padayatty et al., 2004). This revitalized interest and explains why strictly measuring and confirming plasma levels of ascorbate in all subjects is necessary to ensure they are reaching therapeutic concentrations (FIG. 18B) (Welsh et al., 2013). Under this more stringent understanding of ascorbate pharmacokinetics, this work, and others in pancreatic and ovarian cancer, have consistently demonstrated selective toxicity to cancer cells as compared to normal cells both in vitro and in vivo (FIGS. 12, 13A-13H) (Du et al., 2010; Monti et al., 2012; Welsh et al., 2013; Ma et al., 2014). Furthermore, the results of the clinical trials demonstrate that ascorbate is safe and tolerable in combination with radio-chemotherapies in GBM/NSCLC subjects and show promising results for potentially increasing efficacy of current treatment regimens (FIGS. 18A-18E).

Figure 19A:
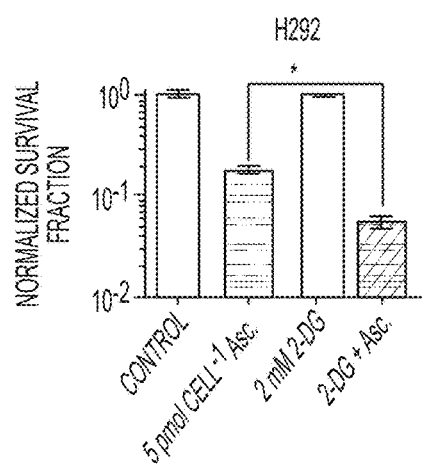
FIGS. 19A-19B. Inhibition of GLUT-mediated DHA uptake does not inhibit ascorbate toxicity. As Yun et al. hypothesized that ascorbate toxicity was dependent on DHA uptake via glucose transporters (GLUTs), we competitively inhibited GLUT transporters with 20 mM 2-deoxy-D-glucose for 15 min prior and during exposure to ascorbate for 1 h and then measured toxicity by clonogenic survival in (FIG. 19A) H292 and (FIG. 19B) H1299 NSCLC cell lines. Data are represented as mean±SEM *represents significant difference, at least p<0.05.
Figure 19B:
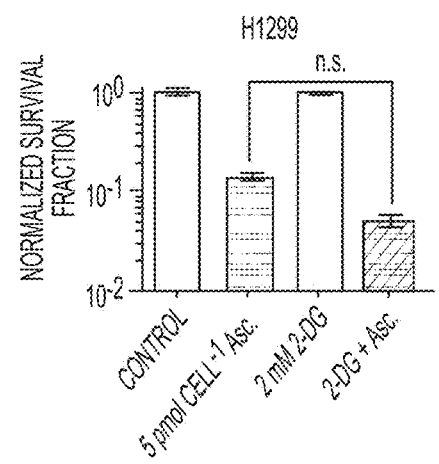

The mechanism underlying the cancer cell-selective toxicity of ascorbate has remained incompletely understood since Cameron and Rotman first hypothesized the utility of pharmacological ascorbate in cancer therapy (Cameron and Rotman, 1972). Recently, Yun et al. hypothesized that the selective toxicity of ascorbate was mediated by increased glucose transporter (GLUT)-mediated uptake of dehydroascorbate and subsequent NAD$^+$ depletion and energetic crisis (Yun et al., 2015). However, in the current study, competitive inhibition of GLUT transporters with 20 mM 2-deoxy-D-glucose (2-DG) did not suppress ascorbate toxicity and appeared to potentially enhance ascorbate toxicity, suggesting that uptake through GLUT-transporters does not contribute to the observed effects in these model systems (FIGS. 19A-19B). Furthermore, inhibition of ascorbate toxicity by exogenous catalase (FIGS. 15A, 15B) or extracellular iron (FIG. 15I), can only be explained by our proposed mechanism of toxicity based on pro-oxidant Fenton-chemistry dependent on ascorbate-produced $H_2O_2$ and intracellular redox-active labile iron.

Figure 20:
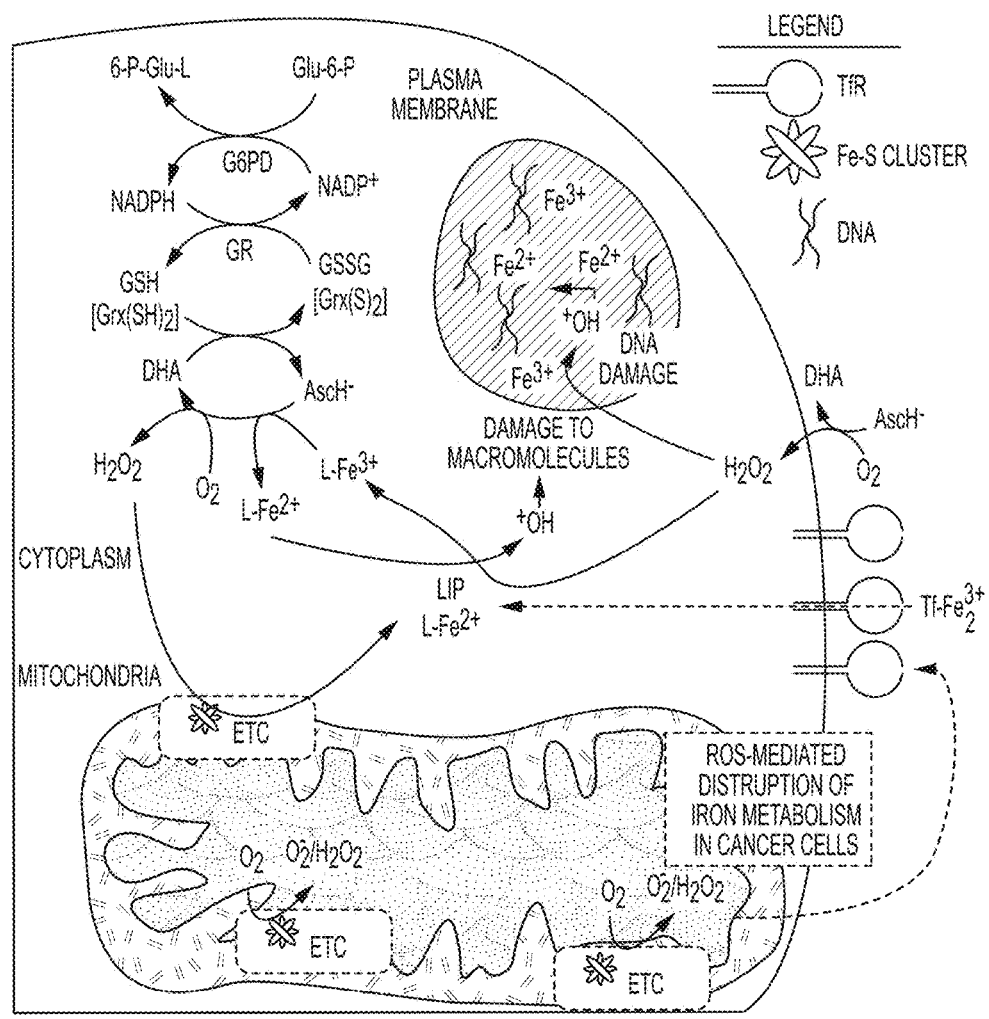
FIG. 20. Proposed mechanism of pharmacological ascorbate cancer-cell selective toxicity. Theoretical model of the mechanism(s) underlying the selective toxicity of pharmacological ascorbate in cancer cells as compared to normal cells. Dashed lines represent multi-step processes not illustrated in the model. Briefly, cancer cells demonstrate increased levels of redox-active labile iron due to increased steady-state levels of $O_2.^-$ and $H_2O_2$, which are capable of disrupting cellular iron homeostasis. Oxidation of ascorbate produces $H_2O_2$ that reacts with the increased LIP in cancer cells to mediate Fenton chemistry and cause oxidative damage to cellular macromolecules (i.e., DNA, protein, lipids). Due to the diffusion-limited kinetics of HO. species, redox-active iron chelated by these macromolecules most likely represent the most prevalent site of damage. Furthermore, $H_2O_2$ produced from ascorbate oxidation selectively increases the cancer cell LIP, partially by disrupting Fe—S clusters, further exacerbating the differences in LIP available for oxidation reactions and mediate ascorbate toxicity in cancer vs. normal cells.

The results of the current study demonstrate that perturbations in redox-active iron metabolism, involving increased steady-state levels of $O_2.^-$ and $H_2O_2$ leading to increased LIP levels, significantly contribute to the cancer cell-selective susceptibility to pharmacological ascorbate combined with standard radio-chemotherapy both in vitro and in vivo in NSCLC and GBM. In our model of selective ascorbate toxicity (FIG. 20), cancer cells possess increased levels of redox-active labile iron due to $O_2.^-$ and $H_2O_2$-mediated disruption of cellular iron homeostasis. Oxidation of ascorbate generates $H_2O_2$ which reacts with the larger LIP in cancer cells to mediate increased rates of Fenton chemistry and hydroxyl radical (.OH) formation to cause oxidative damage and induce cell death as well as further enhance the LIP. This most likely occurs at sites of macromolecule-associated weakly chelated, and therefore redox-active, iron due to the diffusion-limited kinetics of .OH species. In addition to increased basal LIP levels, ascorbate-generated $H_2O_2$ selectively increased cancer cell LIP, partially by disrupting Fe—S containing proteins, further exacerbating the differences in LIP available for oxidation reactions and ascorbate toxicity in cancer vs. normal cells.

Since cancer cells, relative to normal cells, have been hypothesized to demonstrate increased steady-state levels of $O_2.^-$ and $H_2O_2$ due to fundamental defects in oxidative metabolism (Bize et al., 1980; Spitz et al., 2000; Aykin-Burns et al., 2009; Caltagirone et al., 2001; Ibrahim et al., 2013; Pantopoulos et al., 1997; Oberley et al., 1980), the current findings combined with similar findings in pancreas and ovarian cancer (Monti et al., 2012; Welsh et al., 2013; Ma et al., 2014), continue to support the potential for the general application of pharmacological ascorbate in cancer therapy. Given these data, ascorbate may represent an easily implementable addition to current anti-cancer therapies and further large-scale clinical studies are warranted to determine the overall efficacy of ascorbate in NSCLC and GBM. Finally, manipulations of labile iron in cancer cells may represent both a target and a biomarker for predicting responses to pharmacological ascorbate in cancer therapy.

Experimental Procedures

Cell Culture

NSCLC cell lines H1299 and NCI-H292 and HEL 92.1.7 were obtained from the American Type Culture Collection (ATCC) and were grown in RPMI 1640 (Gibco) supplemented with 10% fetal bovine serum (FBS) (HyClone). Human bronchial epithelium primary cells (HBEpC) were maintained in HBE media and growth supplements (Cell Applications, Inc). GBM cell lines U87 and U118 (ATCC) and normal human astrocytes (NHA; Lonza), were grown in supplemented DMEM F12 (Gibco; 15% FBS, 10 μg/mL insulin, 7.5 ng/mL fibroblast growth factor (FGF), 1 mM sodium pyruvate, 15 mM HEPES buffer (pH 7.2), and 100 units/100 μg/mL penicillin-streptomycin). All cells were incubated at 4% $O_2$ in a humidity controlled environment (37° C., 5% $CO_2$; Forma Scientific). All cell lines were utilized before passage 20 and were treated in exponential growth phase at 50-75% confluence 2-3 days following plating. Doubling times of HBEpCs and NHAs were monitored and cells were utilized until doubling time increased by 50%.

Clonogenic Survival Assays

After treatment, cells were washed with PBS and clonogenic assay was completed in their respective media as previously described (Fath et al., 2011). Treatment conditions for individual experiments are as described in the figure legends and summarized in the Supplemental Experimental Procedures.

Murine Xenograft Models

Female 4-6 week old female athymic-nu/nu mice were purchased from Envigo (previously Harlan Laboratories) and housed in the Animal Care Facility at the University of Iowa (Iowa City, Iowa), and all procedures were approved by the University of Iowa Institutional Animal Care and Use Committee and conformed to NIH guidelines. $1 \times 10^6$ H292 or U87 cells were injected subcutaneously into the right rear flank and mice were euthanized and sacrificed when tumor length exceeded 1.5 cm in any dimension. Treatment regimens were as described in the text and are summarized in the Supplemental Experimental Procedures.

Ascorbate Quantification

Tumor xenografts were excised and flash frozen in liquid nitrogen until analysis. Mouse whole blood was collected by cardiac puncture, and plasma was collected after the sample was centrifuged at 500 g for 10 min and frozen until analysis. For patient samples, whole blood was collected from clinical trial patients (NaHeparin 75 USP units, BD Vacutainer® green top blood collection tube, 4 mL), and plasma was collected after centrifugation at 500 g for 10 min and aliquoted and stored at −80° C. until analysis. Total ascorbate for mouse samples and GBM subjects was quantified as previously described (Vislisel et al., 2007; Welsh et al., 2013). Total ascorbate in NSCLC subject's plasma was quantified as previously described (Witmer et al., 2016).

Human Tissue Sample Collection and Inclusion Metrics

Tumor and adjacent normal tissue was collected from patients with suspected or confirmed NSCLC through the IRB-approved University of Iowa Tissue Procurement Core and was frozen in Tissue-Tek® O.C.T. Compound (Sakura® Finetek, VWR). A board certified pathologist from the University of Iowa Hospital and Clinics histologically confirmed the NSCLC diagnosis. Samples were utilized for further studies if histology revealed >75% tumor or normal tissue.

Tissue DHE Staining and Quantification

From OCT-frozen patient tissue, 10 μm sections of both tumor and adjacent normal tissue were cut and placed on the same slide to control. Tissue sections were stained with 10 μM DHE for 30 min at 37° C. in PBS containing 5 mM sodium pyruvate prior to analysis by confocal microscopy. For treatment groups, tissue sections were pretreated for 30 min with 0.25 μM GC4419 SOD mimetic or, alternatively, as a positive control, tissue sections were treated with 10 μM antimycin A (AntA) and DHE for 15 min. Each image obtained was quantified by measuring the mean fluorescence intensity (MFI) of at least 200 cell nuclei, and normalized to untreated normal controls.

Tissue Labile Iron Quantification

Labile iron in patient NSCLC and adjacent normal tissue was quantified as previously described (Moser et al., 2014). Labile iron tissue content was normalized to total tissue protein by the Pierce™ BCA protein assay kit (Thermo-Fisher Scientific), which is not susceptible to interference from residual OCT as opposed to the Lowry method (data not shown).

Cellular Labile Iron Pool Quantification

The labile iron pool (LIP) was visualized using the fluorescent dye Calcein-AM as previously described (Epsztejn et al., 1997) with modifications. After labeling, samples were divided into two flow cytometry sample tubes, to which 100 μM 2',2'-bipyridyl (BIP) was added to one tube and analyzed by flow cytometry. BIP tubes were incubated for at least 15 minutes before analysis to allow for full chelation of intracellular labile iron. The LIP (A.U.)= $MFI_{BIP}-MFI_{NoBIP}$ was normalized against the control samples to calculate the relative labile iron pool.

Western Blots

Cells were lysed in cell lysis buffer (Cell Signaling) and analyzed by standard western blotting procedures. The membranes were incubated with primary antibodies: Ferritin Heavy Chain (1:1,000; AbCam, ab75972), Ferritin Light Chain (1:10,000; AbCam, ab109373), Transferrin Receptor (1:1000; Invitrogen, ref#136800). Actin served as a loading control (1:4,000; Sigma-Aldrich)

CRISPR/Cas9-Mediated Deletion of SOD2

The CRISPR/Cas9 system was utilized to delete mitochondrial SOD2 from HEL 92.1.7 cells as previously described in HEK293T cells (Cramer-Morales et al., 2015).

Enzyme Activity Assays

Exponentially growing cells were scraped and frozen as dry pellets until assayed for total activity. Aconitase activity was measured as the rate of appearance of NADPH (at 340 nm; Beckman DU 800 spectrophotometer, Brea, Calif.) for 45 min during the reaction of 200 μg total sample protein with 200 μM $NADP^+$ and 10 U isocitrate dehydrogenase as previously described (Case et al., 2011). Maximal ETC complex activity was measured as previously described (Birch-Machin et al., 1994). Complex I activity was quantified as the rate of rotenone-inhibitable NADH oxidation (320 nm; $\varepsilon=6.22$ mM$^{-1}$ cm$^{-1}$). Complex II activity as the difference in the rate of DCIP reduction in the presence and absence of succinate (at 600 nm; $\varepsilon=19.1$ mM$^{-1}$ cm$^{-1}$). Complex IV activity was assayed as the rate of oxidation of cytochrome c (500 nm; $\varepsilon=19.6$ mM$^{-1}$ cm$^{-1}$). Rates of activities were normalized to total protein by Lowry.

siRNA

For siRNA-mediated knockdown of TfR, we utilized a commercially available pre-validated siRNA construct (s727, Silencer® Select; Ambion, Life Technologies, ThermoFisher Scientific) as well as a scrambled siRNA transfection control (Silencer® Select Negative Control No. 1). Knockdown in each experiment was confirmed by western blot of immune-reactive TfR protein (representative image: FIG. 16M)

Phase I Clinical Trial of Pharmacological Ascorbate in Combination with Chemoradiation in GBM A phase 1 clinical trial was conducted at the University of Hospitals and Clinics to evaluate the safety of combining pharmacological ascorbate with standard radiation and temozolomide in glioblastoma (GBM) patients. Approval was sought, and obtained, from the University of Iowa Institutional Review Board (Biomedical IRB-01; IRB 201211713). This phase 1 study was registered with clinicaltrials.gov (NCT 01752491) prior to enrollment of the first subject. Newly diagnosed GBM patients referred for standard therapy (Stupp et al., 2005) were invited to participate.

The study was broken into two phases: radiation phase and adjuvant phase. Radiation phase was defined as the time period from day 1 of radiation through adjuvant cycle 1, day 1. Ascorbate infusions were three times weekly, with maximum infusion rate of 500 mL/hour. Radiation (61.2 Gy in 34 fractions) and temozolomide (75 mg/m$^2$ daily for a maximum of 49 days) followed the treatment paradigm put forth by Stupp et al. (Stupp et al., 2005) (FIG. 18A). After completing radiation, ascorbate infusions were reduced to twice weekly for the interim phase (4-5 weeks) with the dose remaining unchanged.

Adjuvant phase was defined as the time period from cycle 1 day 1 through cycle 6 day 28. During this phase, subjects underwent intrapatient ascorbate escalation utilizing Simon's Accelerated Titration Design (Simon et al., 1997). Prescribed doses utilized the same cohorts as the radiation phase. Subjects were dose-escalated after 2 infusions until a plasma level of 20 mM was achieved. Ascorbate infusions were performed twice weekly. Temozolomide was prescribed consistent with the Stupp regimen: 150 mg m$^{-2}$ for days 1 through 5 of a 28 day cycle. A one-time dose escalation was allowed to 200 mg/m$^2$ if cycle 1 was tolerated (FIG. 18A). Subjects were evaluated for disease progression every 2 cycles utilizing the MacDonald criteria (Macdonald et al., 1990).

All subjects agreed to, and participate in, lifelong follow-up for this study. Subject numbers are for convenience and not representative of case ID numbers. Subjects 12 and 13 (FIG. 26) are included in the toxicity analysis (FIGS. 27-28), but were not included in the progression free survival and overall survival analysis (FIG. 18A) because they received limited protocol-dictated therapy due to background disease. Due to the small number of subjects in the longevity analysis we reported the average progression free survival (PFS) and overall survival (OS); however for statistical consistency with Stupp et al., median PFS=9.4 m (range: 3.4-29.3 m) and median OS=15.5 m (range: 7.3-29.3 m).

Phase II Clinical Trial of Pharmacological Ascorbate in Combination with Chemotherapy as a First Line Treatment in Advanced Stage NSCLC This phase II clinical trial is being conducted at the University of Hospitals and Clinics to evaluate the efficacy of combining carboplatin and paclitaxel with pharmacological ascorbate in advanced stage NSCLC patients. Approval was sought, and obtained, from the University of Iowa Institutional Review Board (Biomedical IRB-01; IRB 201412760). This phase II clinical trial was registered with clinicaltrials.gov (NCT 02420314) prior to enrollment of the first subject. Newly diagnosed advanced stage NSCLC patients were invited to participate.

The study included treating patients with 4 cycles of carboplatin AUC 6 and paclitaxel 200 mg m$^{-2}$ every 21 days as first line chemotherapy combined with pharmacological ascorbate. Ascorbate was administered intravenously twice per week at a fixed dose of 75 gm per infusion for 6 treatments per each 21 days cycle of chemotherapy. Whole blood was collected from patients around infusions.

To date, no grade 3/4 toxicities attributed to ascorbate have occurred through 134 total infusions. The regimen is well tolerated and no patients have withdrawn consent due to toxicities. We have not seen any unexpected or unusual increase in Grade 3/4 toxicities as compared to previously published literature, although it remains too early for a direct comparison. Responses to therapy were determined per RECIST 1.1 criteria (Eisenhauer et al., 2009). Currently, four of six patients have completed the trial with imaging-confirmed partial responses to therapy. One additional patient demonstrated stable disease. Finally, one patient progressed with a new spinal lesion, although the target lesions are stable; this patient has been transitioned off of the trial. All subjects agreed to, and participate in, lifelong follow-up for this study.

Statistical Analysis

Data was expressed as mean±1 S.E.M., unless otherwise specified. For all analyses, significance was determined at $p<0.05$. All analyses, unless specified elsewhere, were performed in GraphPad Prism® (GraphPad Software, Inc). For analyses limited to two groups, Student's t test was utilized. To study differences between three or more groups, one-way ANOVA analysis with Tukey's post hoc test was used. Ascorbate toxicity curves (FIGS. 13A, 13B) were generated using IGOR Pro version 6.36 (WaveMetrics, Inc). For survival analyses (FIGS. 14A, 14B), the log-rank Mantel-Cox test was used. For NSCLC LIP curves (FIG. 17A) non-linear regression curves were compared by the extra sum-of-squares F test. For GBM and NSCLC-Ft LIP curves (FIGS. 17B, 17J) deviation from non-zero slope was determined from linear regression analyses. Box and whisker blot of patient plasma ascorbate concentrations (FIG. 18B) are determined by the Tukey method, where dots represent statistically significant outliers.

Supplemental Experimental Procedures

Chemicals and Reagents

Unless noted, reagents were obtained from Sigma-Aldrich (St. Louis, Mo.). L-ascorbic acid was purchased from Macron Chemicals (Center Valley, Pa.) while clinical preparations were purchased from Mylan Institutional (Galway, Ireland) or McGuff Pharmaceuticals, Inc. (Santa Clara, Calif.). Carboplatin chemotherapy was purchased from Hospira, Inc. (Lake Forest, Ill.). Ketamine was purchased from Mylan Institutional (Galway, Ireland) and xylazine was purchased from Lloyd Laboratories (Shenandoah, Iowa).

Ferrous ammonium sulfate was purchased from J. T. Baker (Center Valley, Pa.). GC4419 SOD mimetic was provided by Galera Therapeutics (Malvern, Pa.). Dihydroethidium and Calcein-AM fluorescent dyes were purchased from Life Technologies (Eugene, Oreg.).

Ascorbate and Ascorbate Exposure

L-ascorbic acid stock solution (approx. 1 M) was made in Nanopure® Type 1 water (18 MS2) with the pH adjusted to 7.0 with 1 M NaOH, stored in sealed glass tubes with minimal head space, and the precise concentration was confirmed spectrophotometrically as previously described (265 nm, ε=14.5 mM-1 cm-1) (Buettner, 1988). For all experiments directly comparing the effects of ascorbate on cancer and normal cells, ascorbate is dosed per cell due to previous literature demonstrating that $H_2O_2$ and ascorbate toxicity is dependent on this metric (Doskey et al., 2015; Spitz et al., 1987). Furthermore, the media conditions during cancer vs. normal comparisons are identical, as media constitution (i.e. serum, pyruvate and other α-ketoacids, metal ions, etc.) and media pH modulate ascorbate toxicity (Buettner, 1988; Spitz et al., 1987; Olney et al., 2013; Nath et al., 1995; Clément et al., 2001; Mojić et al., 2014). For clinical dosing, the studies utilize commercially available, prescription-only L-ascorbic acid for intravenous injection (500 mg mL-1).

Cell Culture

NSCLC cell lines H1299 and NCI-H292 and HEL 92.1.7 were obtained from the American Type Culture Collection (ATCC) and were grown in RPMI 1640 (Gibco) supplemented with 10% fetal bovine serum (FBS) (HyClone). Human bronchial epithelium primary cells (HBEpC) were maintained in HBE media and growth supplements (Cell Applications, Inc). GBM cell lines U87 and U118 (ATCC) and normal human astrocytes (NHA; Lonza), were grown in supplemented DMEM F12 (Gibco; 15% FBS, 10 μg/mL insulin, 7.5 ng/mL fibroblast growth factor (FGF), 1 mM sodium pyruvate, 15 mM HEPES buffer (pH 7.2), and 100 units/100 μg/mL penicillin-streptomycin). All cells were incubated at 4% $O_2$ in a humidity controlled environment (37° C., 5% $CO_2$; Forma Scientific). All cell lines were utilized before passage 20 and treated in exponential growth phase at 50-75% confluence. Doubling times of HBEpCs and NHAs were monitored and cells were utilized until doubling time increased by 50%.

Ionizing Radiation

Ionizing radiation (IR) was delivered in the Iowa Radiation and Free Radical Research Core facility using a Pantak Therapx DXT 300 X-ray machine operated at 200 kVp with added filtration of 0.35 mm Cu+1.5 mm Al, resulting in a beam quality of 0.95 mm Cu. For in vitro studies, cells were irradiated in 60 mm cell culture dishes. For in vivo murine xenograft studies, mice were anesthetized using an 87.5 mg kg-1 ketamine and 12.5 mg kg-1 xylazine mixture and placed in lead boxes with only their right flank exposed.

Clonogenic Survival Assays $1\text{-}2\times10^5$ cells were plated in 60 mm cell culture dishes and grown in their respective media for 48 h before exposed to experimental conditions. For radiochemotherapy sensitization experiments, the cells were sequentially exposed to 1 h chemotherapy, 1 h pharmacological ascorbate, and then 2 Gy IR. For bovine catalase experiments, catalase was added 1 min prior to ascorbate exposure. For AdGPx1 experiments, cells were supplemented with 50 nM sodium selenite following transduction and throughout clonogenic growth. For iron chelation or iron addition experiments, chelators were added 3 h prior to and during ascorbate exposure to ensure that labile metal ions were sufficiently bound. For experiments investigating the role of intracellular versus extracellular iron chelators, chelators were either added 3 h prior to ascorbate exposure and washed before ascorbate exposure, or media that was to be added later during ascorbate exposure was pre-chelated for 3 h at 37° C. For 2-DG experiments, 20 mM 2-DG was added only 15 min prior to ascorbate exposure to ensure minimal 2-DG-mediated effect of cellular redox potential. After treatment, cells were washed with PBS and clonogenic assay was completed in their respective media. Briefly, floating and attached cells were collected and total cells per plate were counted. An experimentally derived number of cells were plated into each well of a 6-well cell culture plate in their respective media. For HEL92.1.7 suspension cells, cells were seeded in a top layer of 0.4% (w/v) agarose to allow for quantifiable colony formation. After sufficient time (7-12 days, cell type-dependent), cells were fixed in 70% ethanol and stained with a Brilliant Blue methanol solution. Cell colonies containing greater than 50 cells were counted and utilized to calculate plating efficiency for each treatment group. Normalized survival fractions were calculated by comparing plating efficiencies of each treatment group against the control group within a given experiment.

Murine Xenograft Models

Female 4-6 week old female athymic-nu/nu mice were purchased from Envigo (previously Harlan Laboratories) and housed in the Animal Care Facility at the University of Iowa (Iowa City, Iowa), and all procedures were approved by the University of Iowa Institutional Animal Care and Use Committee and conformed to NIH guidelines. $1\times10^6$ H292 or U87 cells were injected subcutaneously into the right rear flank. Once tumors were established, treatment was initiated with daily ascorbate (4 g/kg or equivalent dose of NaCl, IP), weekly carboplatin (5 mg/kg for H292) or temozolomide (2.5 mg/kg for U87), and/or IR (12 Gy/2 frx). Ascorbate/NaCl and chemotherapy was continued for the full extent of the study. Tumors were measured every other day with Vernier calipers (volume=length×width×(width/2)) and mice were euthanized and sacrificed when tumor length exceeded 1.5 cm in any dimension.

Ascorbate Quantification

Tumor xenografts were excised and flash frozen in liquid nitrogen until analysis. Mouse whole blood was collected by cardiac puncture, and plasma was collected after the sample was centrifuged at 500 g for 10 min and frozen until analysis. For patient samples, whole blood was collected from clinical trial patients (NaHeparin 75 USP units, BD Vacutainer® green top blood collection tube, 4 mL), and plasma was collected after centrifugation at 500 g for 10 min and aliquoted and stored at −80° C. until analysis. Total ascorbate for mouse samples and GBM subjects was quantified as previously described (Vislisel et al., 2007; Welsh et al., 2013). Briefly, samples were extracted in a buffer containing 90% methanol and 10% water with 250 μM DETAPAC (90:10, v/v), mixed, and incubated on ice for 10 min to precipitate protein. The samples were clarified by centrifugation (16 g, 10 min) with an Eppendorf model 5415D Microfuge. Specifically, samples were diluted at a ratio of 50 μL of plasma to 450 μL extraction buffer. These samples were then further diluted another 77.5 to 105-fold (therefore, 775-1,050 fold overall) in a buffer containing 72% methanol and 28% water with 250 μM DETAPAC (72:28, v/v). L-ascorbic acid standards were prepared in 72% methanol and 28% water with 250 μM DETAPAC (72:28, v/v) with stock solution concentrations ranging from 2.5 to 50 μM. This protocol ensured that all samples had identical methanol content which is critical for accurate quantification (Vislisel et al., 2007). 100 µL aliquots of the samples or standards were placed in 96-well optical bottom black plates (Thermo Fisher Scientific, Rochester, N.Y., USA). The assay was initiated at room temperature by adding 100 µL of 2.3 mM 4-hydroxy-2,2,6,6-tetramethylpiperidinyloxyl (Tempol) in 2 M sodium acetate trihydrate buffer previously adjusted to pH 5.5 with acetic acid. The samples were then incubated for 10 min in the dark, allowing for Tempol-mediated oxidation of ascorbate to dehydroascorbate (DHA). Subsequently, 42 µL of 5.5 mM orthophenylenediamine (oPDA) in 2 M sodium acetate buffer (pH 5.5) was added to the samples. Kinetic measurements were immediately initiated and collected every 22 s using a TECAN SpectraFluor Plus plate reader (Tecan, Research Triangle Park, N.C., USA) for the fluorescent condensation product of the reaction of oPDA with DHA (3-dihydroxyethyl)furo[3,4-b]quinoxaline-1-one; $\lambda_{ex}$=345 nm, $\lambda_{em}$=425 nm). Plasma ascorbate concentrations were determined against the linear portions of the standard curve and corrected for previous dilutions. Total ascorbate in NSCLC subject's plasma was quantified as previously described (Witmer et al., 2016). Briefly, plasma samples were measured spectrophotometrically (265 nm; $\varepsilon$=13,000 M-1 cm-1) using an Implen Nanophotometer P-330 with a 250× dilution lid, path length=4.00×10-3 cm. The blank for each sample was a pair-'pre-infusion' plasma sample, which allowed removal of the background absorbance of plasma proteins and other constituents.

CSF Ascorbyl Radical Electron Paramagnetic Resonance (EPR)

CSF was collected from nude athymic female mice that had received daily IP injections of ascorbate (4 g kg$^{-1}$) for two weeks as previously described (Liu and Duff, 2008). Briefly, mice were anesthetized (17.5 mg ml$^{-1}$ ketamine/2.5 mg ml$^{-1}$ xylazine mixture), restrained in a stereotaxic frame with an acute head angle, and the dura mater covering the foramen magnum was surgically exposed. CSF was collected by capillary action following minimal puncture of the dura mater and frozen until EPR analysis. Ascorbyl radical EPR spectra were obtained by placing the capillary tube into the bottom of a 250 mm×3 mm (ID) thin walled quartz EPR tube (707-SQ-250M Wilmad-Lab Glass, Vineland, N.J.) centered in a Bruker HS EPR cavity (Bruker, Billerica, Mass.). Spectra of the ascorbyl radical (g=2.0052) were acquired by a Bruker EMX EPR spectrometer at room temperature while using a microwave power of 3.2 mW; frequency, 9.858 GHz; scanning 10 G with a sweep time of 20.972 s; receiver gain, 5.02×104; modulation frequency, 100 kHz; modulation amplitude, 0.70 G; signal channel time constant, 327.680 ms. Spectra were collected in the additive mode using 5 scans.

Adenovirus Transduction

Replication-incompetent adenoviral vectors, Ad-empty (AdE), AdCMV catalase (AdCat), AdCMV glutathione peroxidase 1 (AdGPx1), AdCMV SOD1 (AdSOD1), and AdCMV SOD2 (AdSOD2) vectors are previously described (Zwacka et al., 1998; Ahmad et al., 2005, 2008). AdFerritin heavy and light chain (AdFtH and AdFtL, respectively) were synthesized by ViraQuest (North Liberty, Iowa) using commercially available iron regulatory element (IRE)-lacking vectors (OriGene). All transductions were performed in serum-free DMEM for 8-12 h once cells reached 50-70% confluence. Cells were washed and grown in full media for an additional 36 hours before experiments were conducted. All transductions were confirmed by activity assay and/or western blot for each individual experiment.

Human Tissue Sample Collection and Inclusion Metrics

Tumor and adjacent normal was collected from patients with suspected or confirmed NSCLC patients through the IRB-approved University of Iowa Tissue Procurement Core and was frozen in Tissue-Tek® O.C.T. Compound (Sakura® Finetek, VWR) A board certified pathologist from the University of Iowa Hospital and Clinics histologically confirmed the NSCLC diagnosis. Samples were utilized for further studies if histology revealed >75% tumor or normal tissue, respectively, in adjacent tissue slices both before and after the samples were collected.

Tissue DHE Staining and Quantification

From OCT-frozen patient tissue, 10 µm sections of both tumor and adjacent normal tissue were cut and placed on the same slide to control. Tissue sections were stained with 10 DHE for 30 min in PBS+5 mM sodium pyruvate prior to analysis by confocal microscopy (Olympus FLUOVIEW FV1000). For treatment groups, tissue sections were pretreated for 30 min with 0.5 µM GC4419 SOD mimetic or, alternatively, as a positive control, tissue sections were co-treated with 10 µM antimycin A (AntA) during the last 15 min of DHE staining. Each image obtained was quantified by measuring the mean fluorescence intensity of at least 200 cell nuclei (ImageJ), and normalized to nuclei from untreated normal tissue cell nuclei.

Tissue Iron Quantification

Labile iron in patient NSCLC and adjacent normal tissue was quantified as previously described (Moser et al., 2014). Where ever possible, metal instrumentation was avoided to prevent contamination from adventitious labile iron. Briefly, tissue sections were homogenized in a 1.5 mL eppendorf tube by plastic pestle in 350 µL PBS (pH 6.5) that was previously treated with Chelex® 100 beads to remove any adventitious labile iron. To this homogenate, 2 mM DFO (final concentration) was added and samples were incubated on ice for 1 h and frozen at −80 C until analysis. For analysis, samples were placed in 4 mm O.D. EPR tubes (Wilmad-LabGlass, Vineland, N.J., 707-SQ-250M) and were flash frozen in liquid nitrogen. The samples were then analyzed for labile iron by using EPR (Bruker EMX EPR spectrometer), monitoring for the high spin ferrioxamine ($Fe^{3+}$−DFO) signal at g=4.3 at 100 K (Bruker ER4111VT variable temperature accessory) with the following EPR instrument parameters: center field 1575 G, sweep width 500 G, typical microwave frequency 9.766 GHz, power 20 mW, receiver gain 2×105, modulation frequency 100 kHz, modulation amplitude 2 G, time constant 163.84 ms, conversion time 20.48 ms, resolution 1024 points, and with 5 additive scans. All samples were analyzed three times, repositioning the sample in the cavity before initiating each additional scan. The mean signal intensity was quantified and the labile iron content was calculated using a standard curve (0-15 µM FAS with 1 mM DFO) and normalized to total tissue protein by the Pierce™ BCA protein assay kit (ThermoFisher Scientific), which is not susceptible to interference from residual OCT as opposed to the Lowry method (data not shown).

CRISPR/Cas9-Mediated Deletion of SOD2

Figure 24:
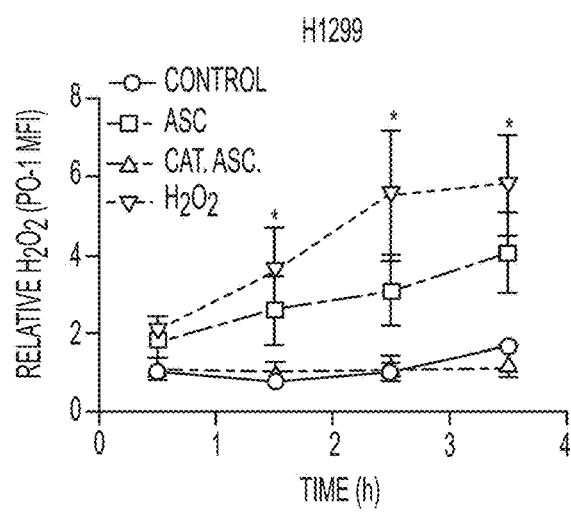
FIG. 24. (Related to FIGS. 17A-17N) Ascorbate-mediated oxidation of PO-1 is mediated by H2O2. As PO-1 is sensitive to oxidation by both $H_2O_2$ and peroxynitrite, $H_2O_2$ was confirmed as the causative species by addition of 50 U mL-1 bovine catalase 5 minutes before the addition of 15 pmol cell-1 ascorbate or 15 pmol cell-1 ascorbate alone. Addition of 100 µM genuine $H_2O_2$ was added every 30 min as a positive control. Cells were subsequently analyzed by flow cytometry. Data are represented as mean±SEM. *represents significant difference, at least p<0.05.

The CRISPR/Cas9 system was utilized to delete mitochondrial SOD2 from HEL 92.1.7 cells as previously described in HEK293T cells (Cramer-Morales et al., 2015). Briefly, cells were electroporated (200 V, 30 µF) with the custom synthesized pD130-GFP expression vector containing expression cassettes for green fluorescent protein (GFP), Cas9 endonuclease, and a CRISPR chimeric cDNA with a gRNA moiety designed to target SOD2 (DNA 2.0, Menlo Park, Calif.). Cells that transiently expressed GFP were sorted by flow cytometry and cloned. Deletion of SOD2 was confirmed by sequencing (data not shown), western blot, and activity assays (FIG. 24).

Cellular Labile Iron Pool Quantification

The labile iron pool (LIP) was visualized using the fluorescent dye Calcein-AM as previously described with modifications (Epsztejn et al., 1997). Briefly, after sample treatment, cells were trypsinized, spun at 1,200 rpm for 5 min, and resuspended at approximately $1 \times 10^6$ cells mL-1 in 500 nM Calcein-AM in PBS. Samples were incubated for 15 min at 4% $O_2$ in a humidity controlled environment (37° C., 5% $CO_2$). Subsequently, samples were pelleted, washed in PBS, and resuspended in 1 mL PBS before dividing each sample into two flow cytometry sample tubes, to which 100 µM 2',2'-bipyridyl (BIP) was added to one tube. Samples were kept at room temperature and analyzed on a LSR II Flow Cytometer (BD Biosciences; $\lambda$ex=488 nm, $\lambda$em=515/20 nm). BIP tubes were incubated for at least 15 minutes before analysis to allow for full chelation of intracellular labile iron. The LIP (A.U.)=MFIBIP−MFINoBIP was normalized against the control samples to calculate the relative labile iron pool.

Western Blots

Exponentially growing cells were washed with PBS before the addition of lysis buffer (Cell Signaling), incubated on ice for 5 minutes, and scraped. The lysate was collected and centrifuged to remove cellular debris. The protein concentrations were determined on the cleared lysate using the Bio-Rad DC Bradford Protein Assay (Bio-Rad Laboratories, Hercules, Calif. Total protein (25 ug) was electrophoresed on a 4-20% gradient gel (Bio-Rad) at 80 V for approximately 1 h. The separated proteins were transferred onto PVDF membrane (Millipore, Billerica, Calif.) and non-specific binding was blocked using 5% nonfat dry milk in PBS-Tween (0.2%) for 1 h at room temperature. The membranes were incubated with primary antibodies (Ferritin heavy chain, 1:1000, Ferritin light chain 1:10,000, both antibodies from Abcam, Cambridge, Mass., Transferrin receptor, 1:1000, Invitrogen, Camarillo, Calif.) at 4° C. overnight. Actin served as a loading control (1:4,000; Sigma-Aldrich). Following 3×5 min PBS-Tween washes, the membranes were blotted with secondary antibodies (1:25,000; Sigma-Aldrich, St. Louis, Mo.) that were conjugated with horseradish peroxidase for 1 hour. The washed membranes were incubated with Super Signal West Pico Chemiluminescent Substrate (Thermo Scientific, Rockford, Ill.) and exposed to CareStream BioMax MR Film (CareStream Health, Rochester, N.Y).

siRNA

For siRNA-mediated knockdown of TfR, we utilized a commercially available pre-validated siRNA construct (s727, Silencer® Select; Ambion, Life Technologies, ThermoFisher Scientific) as well as a scrambled siRNA transfection control (Silencer® Select Negative Control No. 1). Cells were plated and allowed to grow 36-48 h until they reached 30-40% confluence. siRNA (25 pmol per dish) and Lipofectamine® 2000 (10 µL per dish) were prepared as instructed in OptiMEM transfection media (Gibco). A master mix of siRNA (25 pmol per dish) and lipofectamine (10 µL per dish) were individual diluted in 500 µL OptiMEM per dish and allowed to incubate for 5 min at room temperature. These solutions were then combined, mixed gently, and allowed to incubate for an additional 20 min before adding 1 mL of the solution to each washed cell culture dish. The cells were exposed to the transfection medium for 8-12 h, washed, and grown in full media until 80-90% confluence. Further experiments were conducted as described above.

Because TfR mRNA is mostly regulated post-transcriptionally, and our endpoint was knockdown of TfR, knockdown in each experiment was confirmed by western blot of immune-reactive TfR protein (representative image: FIG. 16M).

Aconitase Activity

Exponentially growing cells were scraped and frozen as dry pellets until assayed for total aconitase activity adapted from as previously described (Case et al., 2011). Briefly, cell pellets were resuspended in 50 mM Tris-HCl, pH 7.4 with 0.6 mM $MnCl_2$ and 5 mM Na-citrate and sonicated 3×10 s each. Protein was quantified by the Lowry method (Lowry et al., 1951). Aconitase activity was measured as the rate of appearance of NADPH (at 340 nm; Beckman DU 800 spectrophotometer, Brea, Calif.) for 45 min during the reaction of 200 µg total sample protein with 200 µM NADP+ and 10 U isocitrate dehydrogenase.

ETC Complex Activity

Exponentially growing cells were scraped and frozen as dry pellets until assayed for protein content (Lowry) and maximal ETC complex activity as previously described (Birch-Machin et al., 1994). Briefly, dry cell pellets were resuspended in 20 mM potassium phosphate buffer and sonicated 3×10 s each. Rates of activities were normalized to total protein. Complex I activity was quantified as the rate of rotenone-inhibitable NADH oxidation (320 nm; $\epsilon$=6.22 mM-1 cm-1). Samples were assayed in the presence or absence of 200 µg mL-1 rotenone in 25 mM potassium phosphate working buffer (5 mM $MgCl_2$, 2 mM KCN, 2.5 mg mL-1 BSA, 0.13 mM NADH, 200 µg mL-1 antimycin A, 7.5 mM coenzyme Q1). Complex II activity was measured in the presence and absence of 0.2 M succinate in 25 mM potassium phosphate working buffer (5 mM $MgCl_2$, 2 mM KCN, 2.5 mg mL-1 BSA for 10 minutes at 30 C. After incubation, 200 µg mL-1 antimycin A, 200 µg mL-1 rotenone, 5 mM 2,6-dichloroindophenol (DCIP), and 7.5 mM coenzyme Q1 were added to each cuvette and incubated for 1 min before quantifying Complex II activity as the difference in the rate of DCIP reduction in the presence and absence of succinate (at 600 nm; c=19.1 mM-1 cm-1). Complex IV activity was assayed as the rate of oxidation of cytochrome c (500 nm; c=19.6 mM-1 cm-1). Whole cell lysates were assayed in 25 mM potassium phosphate buffer (0.5 mM n-dodecyl β-maltoside, 1.5 mM reduced cytochrome c).

Quantification of Intracellular $H_2O_2$ with PeroxyOrange-1

To visualize intracellular $H_2O_2$ levels, the selectively sensitive fluorescent probe PeroxyOrange-1 was utilized as previously described with modifications (Dickinson et al., 2010). $1 \times 10^5$ cells were plated and grown in their respective media for 48 h. The complete protocol was conducted in the dark with minimal ambient lighting. Cells were washed with PBS and incubated with 10 uM PO-1 in phenol red free RPMI supplemented with HBE growth supplements for 1 h at 37° C. Cells were then washed in PBS and placed back in phenol red free RPMI supplemented with HBE growth supplements. At this time, treatment with 15 pmol cell-1 ascorbate or 100 uM $H_2O_2$ (every 30 min) was initiated and cells were placed back at 37° C. At times indicated, cells were placed on ice for the remainder of the protocol, washed, and trypsinized with phenol red free 0.5% trypsin. After 15 min, cells still attached were scraped and all cells were collected in 15 mL conical vials containing PBS+10% FBS to neutralize the trypsin reaction. Cells were spun at 1200 rpm for 5 min at 4° C., resuspended in 300-500 uL PBS and were run on a LSR II Flow Cytometer (BD Biosciences) with $\lambda$ex=561 nm, $\lambda$em=585/20 nm. The mean fluorescence intensity (MFI) was analyzed (FlowJo™) and corrected for autoflourescence against unlabeled cells. Normalized MFI was calculated by comparing MFI for a given treatment group against control.

Phase I Clinical Trial of Pharmacological Ascorbate in Combination with Chemoradiation in GBM A phase 1 clinical trial was conducted at the University of Hospitals and Clinics to evaluate the safety of combining pharmacological ascorbate with standard radiation and temozolomide in glioblastoma (GBM) patients. Approval was sought, and obtained, from the University of Iowa Institutional Review Board (Biomedical IRB-01; IRB 201211713). This phase 1 study was registered with clinicaltrials.gov (NCT 01752491) prior to enrollment of the first subject. Newly diagnosed GBM patients referred for standard therapy (Stupp et al., 2005) were invited to participate. Post-consent screening procedures included evaluating for glucose-6-phosphatase dehydrogenase deficiency as well as osmolarity tolerance by challenging the consented subjects with a 15 g ascorbate infusion. The study was broken into two phases: radiation phase and adjuvant phase. Radiation phase was defined as the time period from day 1 of radiation through adjuvant cycle 1, day 1. Doses of pharmacologic ascorbate were escalated utilizing Storer's phase I clinical trial design BD (Storer, 1989). Cohorts were defined as 15 g, 25 g, 50 g, 62.5 g, 75 g, 87.5 g, 100 g, and 125 g. Pharmacologic ascorbate was combined with sterile water for a targeted osmolarity of 500-900 mOsm L-1. Ascorbate infusions were three times weekly, with maximum infusion rate of 500 mL/hour. Radiation (61.2 Gy in 34 fractions) and temozolomide (75 mg/m2 daily for a maximum of 49 days) followed the treatment paradigm put forth by Stupp et al. (Stupp et al., 2005) (FIG. 18A). After completing radiation, ascorbate infusions were reduced to twice weekly; dose remained unchanged. Adjuvant phase was defined as the time period from cycle 1 day 1 through cycle 6 day 28. During this phase, subjects underwent intrapatient escalation utilizing Simon's Accelerated Titration Design (Simon et al., 1997). Prescribed doses utilized the same cohorts as the radiation phase. Subjects were dose-escalated after 2 infusions until a plasma level of 20 mM was achieved. Ascorbate infusions were performed twice weekly. Temozolomide was prescribed consistent with the Stupp regimen: 150 mg m-2 for days 1 through 5 of a 28 day cycle. A one-time dose escalation was allowed to 200 mg/m2 if cycle 1 was tolerated (FIG. 18A). Subjects were evaluated for disease progression every 2 cycles utilizing the MacDonald criteria (Macdonald et al., 1990). Dose limiting toxicities (DLTs) for the study included grade 4 infection, grade 3 nausea or vomiting despite maximum supportive care, grade 4 neutropenia or thrombocytopenia, and serious adverse events (SAE) with causality to the investigational agent. In addition to DLT, criteria for removal included progressive disease, patient's refusal to continue treatment, and extraordinary medical circumstances (e.g., the constraints of the protocol are considered detrimental to patient health). All subjects agreed to, and participate in, lifelong follow-up for this study. Subject numbers are for convenience and not representative of case ID numbers. Subjects 12 and 13 (FIG. 26) are included in the toxicity analysis (FIGS. 27-28), but were not included in the progression free survival and overall survival analysis (FIG. 18A) because they received limited protocol-dictated therapy due to background disease. Due to the small number of subjects in the longevity analysis we reported the average progression free survival (PFS) and overall survival (OS); however for statistical consistency with Stupp et al., median PFS=9.4 m (range: 3.4-31.1 m) and median OS=15.5 m (range: 7.3-31.1 m). Estimated median overall survival (OS) as determined by the method of Kaplan-Meier is 28.4 months.

Phase II Clinical Trial of Pharmacological Ascorbate in Combination with Chemotherapy as a First Line Treatment in Advanced Stage NSCLC This phase II clinical trial is being conducted at the University of Hospitals and Clinics to evaluate the efficacy of combining carboplatin and paclitaxel with pharmacological ascorbate in advanced stage NSCLC patients. Approval was sought, and obtained, from the University of Iowa Institutional Review Board (Biomedical IRB-01; IRB 201412760). This phase II clinical trial was registered with clinicaltrials.gov (NCT 02420314) prior to enrollment of the first subject. Newly diagnosed advanced stage NSCLC patients were invited to participate. Post-consent screening procedures included evaluating for glucose-6-phosphatase dehydrogenase deficiency as well as osmolarity tolerance by challenging the consented subjects with a 15 g ascorbate infusion. The study included treating patients with 4 cycles of carboplatin AUC 6 and paclitaxel 200 mg m-2 every 21 days as first line chemotherapy combined with pharmacological ascorbate. Ascorbate was administered intravenously twice per week at a fixed dose of 75 gm per infusion for 6 treatments per each 21 days cycle of chemotherapy. Pharmacologic ascorbate was combined with sterile water for a targeted osmolarity of 500-900 mOsm/L. Blood ascorbate levels and measures of reactive oxygen species were collected from patients around infusions. So far, no grade 3/4 toxicities attributed to ascorbate have occurred through 134 total infusions. The regimen is well tolerated and no patients have withdrawn consent due to toxicities. We have not seen any unexpected or unusual increase in Grade 3/4 toxicities as compared to previously published literature, although it remains too early for a direct comparison. Responses to therapy were determined per RECIST 1.1 criteria (Eisenhauer et al., 2009). Currently, a total of eleven subjects have been recruited to the trial, seven of which are currently evaluable for response. Five of seven patients have completed the trial with imaging-confirmed partial responses to therapy. One additional patient demonstrated stable disease. Finally, one patient progressed with a new spinal lesion, although the target lesions are stable; this patient has been transitioned off of the trial. All subjects agreed to, and participate in, lifelong follow-up for this study.

SOD Activity Assay

MnSOD activity was measured in cell lysates as previously described (Spitz and Oberley, 2001). Briefly, dry cell pellets were homogenized in 50 mM phosphate buffer with 1.34 mM DETAPAC. To measure MnSOD activity only, the sample is incubated with 5 mM NaCN— for 30 min to inhibit CuZnSOD activity. To measure the MnSOD activity, the rate of nitroblue tetrazolium (NBT) reduction was measured during the reaction of 100 μL of increasing amounts of total sample protein (0-500 mg), 100 μL of 10-2 U mL-1 xanthine oxidase, and 800 μL of 50 mM phosphate buffer (1 mM DETAPAC, 0.13 mg mL-1 BSA, 1.0 U mL-1 catalase, 5.6×10-5 M NBT, 1×10-4 M xanthine, 5 mM NaCN—, 50 μM bathocuproine disulfonic acid) at 560 nm for 2 mM. One unit of SOD activity is measured as the amount of protein necessary to reach 50% of maximum inhibition of NBT reduction. To account for incomplete CN— mediated inhibition of CuZnSOD activity, MnSOD and CuZnSOD activity was more specifically differentiated by a SOD activity gel as adapted from techniques previously described (Ornstein, 1964). Briefly, a 12% polyacrylamide gel was made and pre-electrophoresed for 1 h at 40 A (188 mM Tris-base, 1.3 mM EDTA, pH 8.8). The following day, a 5% polyacrylamide stacking gel with 0.004% riboflavin-5'-phosphate with a 1.5 mm comb was solidified under a fluorescent light for 15-30 min. 100 μg total protein was electrophoresed for approximately 3 h at 40 A (50 mM Tris base, 300 mM glycine, 2.3 mM EDTA, pH 8.3) while the gel electrophoresis box was placed in an ice bath to maintain protein activity. The gels were then soaked in the staining solution (2.43 mM NBT, 28 mM TEMED, $2.8 \times 10^{-5}$ riboflavin-5'-phosphate in ddH2O) for 20 min at room temperature in the dark. The gels were then rinsed, placed in 50 mM phosphate buffer (pH 7.8) and exposed to fluorescent light to initiate superoxide production. Achromatic bands indicate the presence of SOD activity. Once developed, the gels were further developed at room temperature overnight and imaged.

Statistical Analysis

Data was expressed as mean±1 S.E.M., unless otherwise specified. For all analyses, significance was determined at $p<0.05$. All analyses, unless specified elsewhere, were performed in GraphPad Prism® (GraphPad Software, Inc). For analyses limited to two groups, Student's t test was utilized. To study differences between three or more groups, one-way ANOVA analysis with Tukey's post hoc test was used. Ascorbate toxicity curves (FIG. 1A, B) were generated using IGOR Pro version 6.36 (WaveMetrics, Inc). For survival analyses (FIG. 2A,B), the log-rank Mantel-Cox test was used. For NSCLC LIP curves (FIG. 5A) non-linear regression curves were compared by the extra sum-of-squares F test. For GBM and NSCLC-Ft LIP curves (FIG. 5B, J) deviation from non-zero slope was determined from linear regression analyses. Box and whisker blot of patient plasma ascorbate concentrations (FIG. 6B) are determined by the Tukey method, where dots represent statistically significant outliers.

Example 4 References

Ahmad, I. M., Aykin-Burns, N., Sim, J. E., Walsh, S. A., Higashikubo, R., Buettner, G. R., Venkataraman, S., Mackey, M. A., Flanagan, S. W., Oberley, L. W., et al. (2005). Mitochondrial $O_2^{.-}$ and $H_2O_2$ mediate glucose deprivation induced stress in human cancer cells. J. Biol. Chem. 280, 4254-4263.

Ahmad, I. M., Abdalla, M. Y., Aykin-Burns, N., Simons, A. L., Oberley, L. W., Domann, F. E., and Spitz, D. R. (2008). 2-Deoxyglucose combined with wild-type p53 overexpression enhances cytotoxicity in human prostate cancer cells via oxidative stress. Free Radic. Biol. Med. 44, 826-834.

Aykin-Burns, N., Ahmad, I. M., Zhu, Y., Oberley, L. W., and Spitz, D. R. (2009). Increased levels of superoxide and H2O2 mediate the differential susceptibility of cancer cells versus normal cells to glucose deprivation. Biochem. J. 418, 29-37.

Birch-Machin, M. A., Briggs, H. L., Saborido, A. A., Bindoff, L. A., and Turnbull, D. M. (1994). An evaluation of the measurement of the activities of complexes I-IV in the respiratory chain of human skeletal muscle mitochondria. Biochem. Med. Metab. Biol. 51, 35-42.

Bize, I. B., Oberley, L W., and Morris, H. P. (1980). Superoxide Dismutase and Superoxide Radical in Morris Hepatomas. Cancer Res. 40, 3686-3693.

Boyer, R. F., and McCleary, C. J. (1987). Superoxide ion as a primary reductant in ascorbate-mediated ferritin iron release. Free Radic. Biol. Med. 3, 389-395.

Buettner, G. R. (1986). Ascorbate autoxidation in the presence of iron and copper chelates. Free Radic. Res. Commun. 1, 349-353.

Buettner, G. R. (1988). In the absence of catalytic metals ascorbate does not autoxidize at pH 7: ascorbate as a test for catalytic metals. J. Biochem. Biophys. Methods 16, 27-40.

Buettner, G. R., and Jurkiewicz, B. A. (1996). Catalytic Metals, Ascorbate and Free Radicals: Combinations to Avoid. Radiat. Res. 145, 532-541.

Caltagirone, A., Weiss, G., and Pantopoulos, K. (2001). Modulation of cellular iron metabolism by hydrogen peroxide: Effects of H2O2 on the expression and function of iron-responsive element-containing mRNAs in B6 fibroblasts. J. Biol. Chem. 276, 19738-19745.

Cameron, E., and Pauling, L. (1976). Supplemental ascorbate in the supportive treatment of cancer: Prolongation of survival times in terminal human cancer. Proc. Natl. Acad. Sci. U.S.A. 73, 3685-3689.

Cameron, E., and Rotman, D. (1972). Asocrbic acid, cell proliferation, and cancer. The Lancet 299, 542.

Case, A. J., McGill, J. L., Tygrett, L. T., Shirasawa, T., Spitz, D. R., Waldschmidt, T. J., Legge, K. L., and Domann, F. E. (2011). Elevated mitochondrial superoxide disrupts normal T cell development, impairing adaptive immune responses to an influenza challenge. Free Radic. Biol. Med. 50, 448-458.

Chen, Q., Espey, M. G., Krishna, M. C., Mitchell, J. B., Corpe, C. P., Buettner, G. R., Shacter, E., and Levine, M. (2005). Pharmacologic ascorbic acid concentrations selectively kill cancer cells: action as a pro-drug to deliver hydrogen peroxide to tissues. Proc. Natl. Acad. Sci. U.S.A. 102, 13604-13609.

Chen, Q., Espey, M. G., Sun, A. Y., Lee, J.-H., Krishna, M. C., Shacter, E., Choyke, P. L., Pooput, C., Kirk, K. L., Buettner, G. R., et al. (2007). Ascorbate in pharmacologic concentrations selectively generates ascorbate radical and hydrogen peroxide in extracellular fluid in vivo. Proc. Natl. Acad. Sci. U.S.A. 104, 8749-8754.

Clément, M.-V., Ramalingam, J., Long, L. H., and Halliwell, B. (2001). The In Vitro Cytotoxicity of Ascorbate Depends on the Culture Medium Used to Perform the Assay and Involves Hydrogen Peroxide. Antioxid. Redox Signal. 3, 157-163.

Cramer-Morales, K., Heer, C. D., Mapuskar, K. A., and Domann, F. E. (2015). SOD2 targeted gene editing by CRISPR/Cas9 yields Human cells devoid of MnSOD. Free Radic. Biol. Med. 89, 379-386.

Creagan, E. T., Moertel, C. G., O'Fallon, J. R., Schutt, A. J., O'Connell, M. J., Rubin, J., and Frytak, S. (1979). Failure of high-dose vitamin C (ascorbic acid) therapy to benefit patients with advanced cancer. A controlled trial. N. Engl. J. Med. 301, 687-690.

Dickinson, B. C., Huynh, C., and Chang, C. J. (2010). A Palette of Fluorescent Probes with Varying Emission Colors for Imaging Hydrogen Peroxide Signaling in Living Cells. J. Am. Chem. Soc. 132, 5906-5915.

Doskey, C. M., van't Erve, T. J., Wagner, B. A., and Buettner, G. R. (2015). Moles of a Substance per Cell Is a Highly Informative Dosing Metric in Cell Culture. PloS One 10, e0132572.

Du, J., Martin, S. M., Levine, M., Wagner, B. A., Buettner, G. R., Wang, S., Taghiyev, A. F., Du, C., Knudson, C. M., and Cullen, J. J. (2010). Mechanisms of ascorbate-induced cytotoxicity in pancreatic cancer. Clin. Cancer Res. Off. J. Am. Assoc. Cancer Res. 16, 509-520.

Du, J., Wagner, B. A., Buettner, G. R., and Cullen, J. J. (2015). Role of labile iron in the toxicity of pharmacological ascorbate. Free Radic. Biol. Med. 84, 289-295.

Eisenhauer, E. A., Therasse, P., Bogaerts, J., Schwartz, L. H., Sargent, D., Ford, R., Dancey, J., Arbuck, S., Gwyther, S., Mooney, M., et al. (2009). New response evaluation criteria in solid tumours: revised RECIST guideline (version 1.1). Eur. J. Cancer Oxf. Engl. 1990 45, 228-247.

Epsztejn, S., Kakhlon, O., Glickstein, H., Breuer, W., and Cabantchik, Z. I. (1997). Fluorescence Analysis of the Labile Iron Pool of Mammalian Cells. Anal. Biochem. 248, 31-40.

Fath, M. A., Ahmad, I. M., Smith, C. J., Spence, J., and Spitz, D. R. (2011). Enhancement of carboplatin-mediated lung cancer cell killing by simultaneous disruption of glutathione and thioredoxin metabolism. Clin. Cancer Res. 17, 6206-6217.

Halliwell, B., and Gutteridge, J. M. C. (1990). [1] Role of free radicals and catalytic metal ions in human disease: An overview. B.-M. in Enzymology, ed. (Academic Press), pp. 1-85.

Ibrahim, W. H., Habib, H. M., Kamal, H., St Clair, D. K., and Chow, C. K. (2013). Mitochondrial superoxide mediates labile iron level: evidence from Mn-SOD-transgenic mice and heterozygous knockout mice and isolated rat liver mitochondria. Free Radic. Biol. Med. 65C, 143-149.

Kukulj, S., Jaganjac, M., Boranic, M., Krizanac, S., Santic, Z., and Poljak-Blazi, M. (2010). Altered iron metabolism, inflammation, transferrin receptors, and ferritin expression in non-small-cell lung cancer. Med. Oncol. Northwood Lond. Engl. 27, 268-277.

Liu, L., and Duff, K. (2008). A Technique for Serial Collection of Cerebrospinal Fluid from the Cisterna Magna in Mouse. J. Vis. Exp. JoVE.

Lowry, O. H., Rosebrough, N. J., Farr, A. L., and Randall, R. J. (1951). Protein measurement with the Folin phenol reagent. J. Biol. Chem. 193, 265-275.

Ma, Y., Chapman, J., Levine, M., Polireddy, K., Drisko, J., and Chen, Q. (2014). High-Dose Parenteral Ascorbate Enhanced Chemosensitivity of Ovarian Cancer and Reduced Toxicity of Chemotherapy. Sci. Transl. Med. 6, 222ra18-ra222ra18.

Macdonald, D. R., Cascino, T. L., Schold, S. C., and Cairncross, J. G. (1990). Response criteria for phase II studies of supratentorial malignant glioma. J. Clin. Oncol. Off. J. Am. Soc. Clin. Oncol. 8, 1277-1280.

McCarty, M. F., and Contreras F. (2014). Increasing Superoxide Production and the Labile Iron Pool in Tumor Cells may Sensitize Them to Extracellular Ascorbate. Front. Oncol. 4, 249.

Moertel, C. G., Fleming, T. R., Creagan, E. T., Rubin, J., O'Connell, M. J., and Ames, M. M. (1985). High-dose vitamin C versus placebo in the treatment of patients with advanced cancer who have had no prior chemotherapy. A randomized double-blind comparison. N. Engl. J. Med. 312, 137-141.

Mojić, M., Bogdanović Pristov, J., Maksimović-Ivanić, D., Jones, D. R., Stanić, M., Mijatović, S., and Spasojević, I. (2014). Extracellular iron diminishes anticancer effects of vitamin C: an in vitro study. Sci. Rep. 4, 5955.

Monti, D. A., Mitchell, E., Bazzan, A. J., Littman, S., Zabrecky, G., Yeo, C. J., Pillai, M. V., Newberg, A. B., Deshmukh, S., and Levine, M. (2012). Phase I evaluation of intravenous ascorbic acid in combination with gemcitabine and erlotinib in patients with metastatic pancreatic cancer. PloS One 7, e29794.

Moser, J. C., Rawal, M., Wagner, B. A., Du, J., Cullen, J. J., and Buettner, G. R. (2014). Pharmacological ascorbate and ionizing radiation (IR) increase labile iron in pancreatic cancer. Redox Biol. 2, 22-27.

Nath, K. A., Ngo, E. O., Hebbel, R. P., Croatt, A. J., Zhou, B., and Nutter, L. M. (1995). alpha-Ketoacids scavenge H2O2 in vitro and in vivo and reduce menadione-induced DNA injury and cytotoxicity. Am. J. Physiol. 268, C227-C236.

Oberley, L. W., Oberley, T. D., and Buettner, G. R. (1980). Cell differentiation, aging and cancer: the possible roles of superoxide and superoxide dismutases. Med. Hypotheses 6, 249-268.

Olney, K. E., Du, J., van't Erve, T. J., Witmer, J. R., Sibenaller, Z. A., Wagner, B. A., Buettner, G. R., and Cullen, J. J. (2013). Inhibitors of hydroperoxide metabolism enhance ascorbate-induced cytotoxicity. Free Radic. Res. 47, 154-163.

Ornstein, L. (1964). Disc electrophoresis. I. Background and history. Ann. N. Y. Acad. Sci. 121, 321-349.

Padayatty, S. J., Sun, H., Wang, Y., Riordan, H. D., Hewitt, S. M., Katz, A., Wesley, R. A., and Levine, M. (2004). Vitamin C pharmacokinetics: implications for oral and intravenous use. Ann. Intern. Med. 140, 533-537.

Pantopoulos, K., Mueller, S., Atzberger, A., Ansorge, W., Stremmel, W., and Hentze, M. W. (1997). Differences in the regulation of iron regulatory protein-1 (IRP-1) by extra- and intracellular oxidative stress. J. Biol. Chem. 272, 9802-9808.

Riordan, N. H., Riordan, H. D., Meng, X., Li, Y., and Jackson, J. A. (1995). Intravenous ascorbate as a tumor cytotoxic chemotherapeutic agent. Med. Hypotheses 44, 207-213.

Sandler, A., Gray, R., Perry, M. C., Brahmer, J., Schiller, J. H., Dowlati, A., Lilenbaum, R., and Johnson, D. H. (2006). Paclitaxel-carboplatin alone or with bevacizumab for non-small-cell lung cancer. N. Engl. J. Med. 355, 2542-2550.

Schiller, J. H., Harrington, D., Belani, C. P., Langer, C., Sandler, A., Krook, J., Zhu, J., Johnson, D. H., and Eastern Cooperative Oncology Group (2002). Comparison of four chemotherapy regimens for advanced non-small-cell lung cancer. N. Engl. J. Med. 346, 92-98.

Simon, R., Freidlin, B., Rubinstein, L., Arbuck, S. G., Collins, J., and Christian, M. C. (1997). Accelerated titration designs for phase I clinical trials in oncology. J. Natl. Cancer Inst. 89, 1138-1147.

Spitz, D. R., and Oberley, L. W. (2001). Measurement of MnSOD and CuZnSOD Activity in Mammalian Tissue Homogenates. In Current Protocols in Toxicology, L. G. Costa, E. Hodgson, D. A. Lawrence, and D. J. Reed, eds. (Hoboken, N.J., USA: John Wiley & Sons, Inc).

Spitz, D. R., Dewey, W. C., and Li, G. C. (1987). Hydrogen peroxide or heat shock induces resistance to hydrogen peroxide in Chinese hamster fibroblasts. J. Cell. Physiol. 131, 364-373.

Spitz, D. R., Sim, J. E., Ridnour, L. A., Galoforo, S. S., and Lee, Y. J. (2000). Glucose deprivation-induced oxidative stress in human tumor cells. A fundamental defect in metabolism? Ann. N. Y. Acad. Sci. 899, 349-362.

Storer, B. E. (1989). Design and analysis of phase I clinical trials. Biometrics 45, 925-937.

Stupp, R., Mason, W. P., van den Bent, M. J., Weller, M., Fisher, B., Taphoorn, M. J. B., Belanger, K., Brandes, A. A., Marosi, C., Bogdahn, U., et al. (2005). Radiotherapy plus Concomitant and Adjuvant Temozolomide for Glioblastoma. N. Engl. J. Med. 352, 987-996.

Szatrowski, T. P., and Nathan, C. F. (1991). Production of large amounts of hydrogen peroxide by human tumor cells. Cancer Res. 51, 794-798.

Torti, S. V., and Torti, F. M. (2013). Iron and cancer: more ore to be mined. Nat. Rev. Cancer 13, 342-355.

Verrax, J., and Calderon, P. B. (2009). Pharmacologic concentrations of ascorbate are achieved by parenteral administration and exhibit antitumoral effects. Free Radic. Biol. Med. 47, 32-40.

Vislisel, J. M., Schafer, F. Q., and Buettner, G. R. (2007). A simple and sensitive assay for ascorbate using a plate reader. Anal. Biochem. 365, 31-39.

Welsh, J. L., Wagner, B. A., van't Erve, T. J., Zehr, P. S., Berg, D. J., Halfdanarson, T. R., Yee, N. S., Bodeker, K. L., Du, J., Roberts, L. J., 2nd, et al. (2013). Pharmacological ascorbate with gemcitabine for the control of metastatic and node-positive pancreatic cancer (PACMAN): results from a phase I clinical trial. Cancer Chemother. Pharmacol. 71, 765-775.

Witmer, J. R., Wetherell, B. J., Wagner, B. A., Du, J., Cullen, J. J., and Buettner, G. R. Direct spectrophotometric measurement of supra-physiological levels of ascorbate in plasma. Redox Biol.

Yun, J., Mullarky, E., Lu, C., Bosch, K. N., Kavalier, A., Rivera, K., Roper, J., Chio, I. I. C., Giannopoulou, E. G., Rago, C., et al. (2015). Vitamin C selectively kills KRAS and BRAF mutant colorectal cancer cells by targeting GAPDH. Science aaa5004.

Zwacka, R. M., Dudus, L., Epperly, M. W., Greenberger, J. S., and Engelhardt, J. F. (1998). Redox gene therapy protects human IB-3 lung epithelial cells against ionizing radiation-induced apoptosis. Hum. Gene Ther. 9, 1381-1386.

EXAMPLE 5

Lung cancer is the leading cause of cancer mortality in the world causing approximately 1.3 million deaths per year (ACS Cancer facts and figures 2013). Approximately 85% of all lung cancers are histologically classified as non-small cell lung cancer (NSCLC). The standard treatment for NSCLC includes a combination of surgery, chemotherapy and/or radiation therapy. Despite advances in NSCLC treatment including improved radiation therapy techniques and development of new chemotherapy and biological agents, the 5 year overall survival continues to be poor at approximately 14%. Therefore, additional approaches with limited toxicity that enhance chemo-radiation sensitivity are needed. The NSCLC market is expected to reach $7.9 billion in 2020 with a CAGR of 6.6%. One approach with minimal toxicity that exploits fundamental differences in oxidative metabolism between cancer cells and normal cells is pharmacological ascorbate (also known as intravenous (IV) high dose Vitamin C).

Pharmacological ascorbate was first proposed as an anti-cancer therapy in the 1970s when Dr. Linus Pauling showed that high doses of ascorbate given both intravenously (IV) and orally increased survival in terminal cancer patients of a variety of cancer types by an average of 300 days. However, two randomized trials in the 1980s comparing oral ascorbate alone to placebo showed no therapeutic benefit, and interest in ascorbate waned as an anti-cancer agent. It is now known that only IV delivery achieves blood ascorbate concentrations that reach effective therapeutic levels (≈20 millimolar). In contrast, oral ascorbate is only able to achieve concentrations 1000 times lower, which does not act as an effective anti-cancer agent. Since the 1990s, several groups have demonstrated pharmacological doses of ascorbate are selectively toxic to many cancer types while being relatively non-toxic to normal cells. Furthermore, clinical trials at the University of Iowa in stage IV (metastatic) pancreas cancer patients combining pharmacological ascorbate with the chemotherapy agent, gemcitabine, demonstrated the excellent tolerability and suggested the potential efficacy of this treatment combination.

Side effects attributed to the combination of ascorbate and gemcitabine were rare and included diarrhea and dry mouth; furthermore, the average survival in these stage IV pancreas cancer patients increased from 7 months to 14 months when treated with pharmacological ascorbate and gemcitabine. In addition, a phase I clinical trial combining pharmacological ascorbate with radiation and temozolomide chemotherapy in glioblastoma multiforme (GBM) patients is nearing completion. There were no adverse events attributed to pharmacological ascorbate in combination radiation and temozolomide. Furthermore, patient outcome data appear promising with mean progression free survival as of 7/28/15 at 14 months vs. 7 months for historical controls and 10 of 11 patients that completed the radiation phase of the trial still living (manuscript in preparation). A phase II clinical trial assessing the efficacy of pharmacological ascorbate in combination with radiation and temozolomide is currently under development. Moreover, a phase II clinical trial assessing the efficacy of pharmacological ascorbate combined with carbotaxol chemotherapy in NSCLC patients is currently accruing at the University of Iowa Hospitals and Clinics (www.clinicaltrials.gov NCT02420314).

Figure 30:
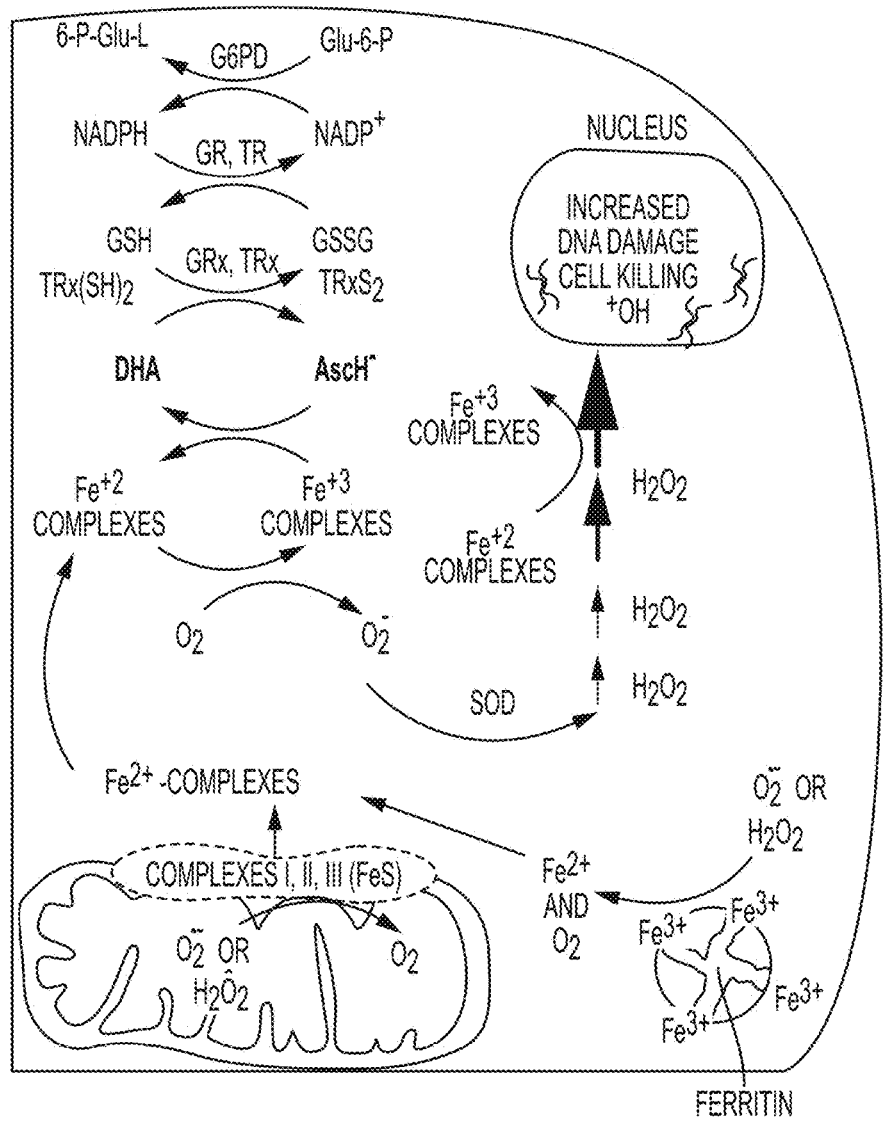
FIG. 30. Theoretical model for the increased generation of cancer cell oxidative stress via generation of hydrogen peroxide ($H_2O_2$) by pharmacological ascorbate (AscH-Cancer cells demonstrate increased steady-state levels of superoxide ($O_2.^-$) and $H_2O_2$ generating oxidative stress in cancer cells. $O_2.^-$ and $H_2O_2$ can react with iron (Fe) bound to proteins to release free iron ($Fe^{2+}$) which is capable of redox cycling to $Fe^{3+}$. This facilitates the production of increasing $H_2O_2$ levels further stressing the cancer cell. We hypothesize that this mechanism may explain why cancer cells generate excess amounts of $H_2O_2$ in the presence of pharmacological ascorbate and hence is capable of enhancing radiation and chemotherapy sensitization, relative to normal cells.

Pharmacological ascorbate is hypothesized to be selectively cytotoxic to cancer cells, as opposed to normal cells, via the generation of $H_2O_2$ which increases oxidative stress in cancer cells. However, the exact details of how pharmacological ascorbate is selectively toxic to cancer cells have yet to be conclusively elucidated. Relative to normal cells, cancer cells demonstrate alterations in $O_2$ metabolism leading to increased levels of reactive oxygen species, including superoxide and hydrogen peroxide ($O_2.^-$ and $H_2O_2$) as well as increased levels of redox active iron. One proposed mechanism for ascorbate's cancer cell specific toxicity is based on this difference in oxidative metabolism between cancer and normal cells (FIG. 30). High levels of superoxide and $H_2O_2$ in cancer cells are believed to mediate the release of protein bound ferrous iron ($Fe^{+2}$) that is then able to undergo redox cycling in the presence of ascorbate generating large amounts of intracellular $H_2O_2$ (FIG. 30). $H_2O_2$ can then be directly toxic to cancer cells by oxidizing amino acids on critical protein targets or producing the highly reactive hydroxyl radical (.OH), which can damage DNA. Because cancer cells (relative to normal) have higher fluxes of $O_2.^-$ and $H_2O_2$ under basal steady-state conditions, high doses of ascorbate can readily facilitate the release of iron leading to cancer cell specific increases in $H_2O_2$ production that enhances sensitivity to standard cancer therapies including radiation and chemotherapy.

We have recently discovered that high levels of ethylenediaminetetraacedic acid (EDTA) further enhance pharmacological ascorbate's cancer cell specific toxicity (see Examples above). EDTA is an iron chelator that is commonly used medically for mercury and lead poisoning. EDTA binds to the free iron but still allows for $Fe^{2+}$ to $Fe^{3+}$ redox cycling resulting in increased generation of $O_2.^-$ and $H_2O_2$. Thus, EDTA combined with pharmacological ascorbate increases cancer cell specific toxicity. Pre-clinical studies with radio-isotope labeled ($^{14}C$) EDTA demonstrate that EDTA it is retained with cancer cells following exposure and that pretreatment with EDTA followed by ascorbate exposure is sufficient for enhanced toxicity. Given the resurgence and excitement of using pharmacological ascorbate in combination with standard cancer therapies, the combination of EDTA with pharmacological ascorbate is extremely valuable for improving responses as well as readily translatable to clinical trial. Since it is not obvious that the characteristic of EDTA redox cycling could have such therapeutic effects this is also a very novel and not at all intuitive approach given the state of the art.

EDTA Combined with Pharmacological Ascorbate Enhances Radiation and Chemotherapy Sensitivity Via Enhancement of Oxidative Stress In Vivo in Lung Cancer Xenograft Models.

Human NSCLC cell lines, NCI-H292 and H1299 are injected into the flanks of nude mice. Flank xenografts are useful because they allow for caliper tumor measurements and also allows for shielding of the body during radiation treatment. Once the tumors reach 2-4 mm in diameter, nine mice are assigned to the following treatment groups: (1) saline (control), (2) ascorbate (4 g/kg), (3) carboplatin (carbo) at 75 mg/kg, (4) radiation (IR) at 12 Gray in 6 fractions over a period of two weeks, (5) EDTA (50 mg/kg/day), (6) EDTA+Asc, (7) carbo+IR+Asc, (8) EDTA+carbo+IR+Asc, (9) Deferoxamine, an iron chelator which prevents redox cycling of iron (75 mg/kg), (10) Deferoxamine+Asc, (11) Deferoxamine+carbo+IR+Asc. Tumor size is measured and volumes calculated daily. The mice are monitored for tumor growth rates, toxicity, and survival. Causal relationships between increased oxidative stress and improved outcomes are confirmed in mice given deferoxamine, which prevents iron redox cycling. Each xenograft experiment is repeated three times.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating a hyperproliferative disorder in a mammal, comprising administering to the mammal a combination of ascorbate, a chelating agent and an anti-cancer therapy, wherein the hyperproliferative disorder is non-small cell lung cancer, and pharmacological doses of ascorbate, calcium disodium EDTA, paclitaxel, and carboplatin are administered, wherein the ascorbate is administered at a dose of about 75 g-100 g infusion 2-5 times per week, calcium disodium EDTA is administered at a dose of about 35-50 mg/kg per day, paclitaxel is administered at a dose of about 200 mg/m$^2$ every 3 weeks, and carboplatin is administered at a dose of about AUC (area under the curve) 6 every 3 weeks.

2. The method of claim 1, wherein the ascorbate and a chelating agent are administered for more than a month.

3. The method of claim 1, wherein the ascorbate and calcium disodium EDTA is administered intravenously.

4. The method of claim 1, wherein:
 a) ascorbate or the pharmaceutically acceptable salt thereof and chelating agent are administered simultaneously with the one or more anti-cancer therapies; or
 b) ascorbate or the pharmaceutically acceptable salt thereof and chelating agent and the one or more anti-cancer therapies are administered sequentially; or
 c) administration of the one or more anti-cancer therapies begins about 1 to about 10 days before administration of the ascorbate or the pharmaceutically acceptable salt thereof and chelating agent; or
 d) administration of ascorbate or the pharmaceutically acceptable salt thereof and chelating agent begins about 1 to about 10 days before administration of the one or more anti-cancer therapies; or
 e) administration of ascorbate or the pharmaceutically acceptable salt thereof and chelating agent and administration of the one or more anti-cancer therapies begins on the same day.

5. The method of claim 1, wherein the anti-cancer therapy is chemotherapy, immunotherapy, biologic therapy, or radiation therapy.

6. The method of claim 5, wherein the radiation therapy is external beam or targeted radionuclide based therapy.

7. The combination of claim 6, wherein the radiation therapy is administered at a dose of about 1.8 to 2 Gy for 25 or more fractions.

8. A method for treating a hyperproliferative disorder in a mammal, comprising administering to the mammal a combination of ascorbate, a chelating agent and an anti-cancer therapy, wherein the hyperproliferative disorder is sarcoma, and pharmacological doses of ascorbate, calcium disodium EDTA, and adriamycin or gemcitabine are administered.

9. The method of claim 8, wherein the ascorbate is administered at a dosage of at least 75 g/day and the chelating agent is administered at a dosage of at least 35 mg/day.

10. The method of claim 8, wherein the ascorbate is administered at a dose of about 75 g-100 g infusion 2-5 times per week, the calcium disodium EDTA is administered at a dose of about 35-50 mg/kg per day, and adriamycin is administered at a dose of about 75 mg/m$^2$ every 3 weeks or gemcitabine is administered at a dose of about 1000 mg/m$^2$ on day 1, day 8, and day 15, and then repeated after 3 weeks.

11. The method of claim 8, wherein the ascorbate and a chelating agent are administered for more than a month.

12. The method of claim 8, wherein the ascorbate and calcium disodium EDTA is administered intravenously.

13. The method of claim 8, wherein:
   a) ascorbate or the pharmaceutically acceptable salt thereof and chelating agent are administered simultaneously with the one or more anti-cancer therapies; or
   b) ascorbate or the pharmaceutically acceptable salt thereof and chelating agent and the one or more anti-cancer therapies are administered sequentially; or
   c) administration of the one or more anti-cancer therapies begins about 1 to about 10 days before administration of the ascorbate or the pharmaceutically acceptable salt thereof and chelating agent; or
   d) administration of ascorbate or the pharmaceutically acceptable salt thereof and chelating agent begins about 1 to about 10 days before administration of the one or more anti-cancer therapies; or
   e) administration of ascorbate or the pharmaceutically acceptable salt thereof and chelating agent and administration of the one or more anti-cancer therapies begins on the same day.

14. The method of claim 8, wherein the anti-cancer therapy is chemotherapy, immunotherapy, biologic therapy, or radiation therapy.

15. The method of claim 14, wherein the radiation therapy is external beam or targeted radionuclide based therapy.

16. The combination of claim 14, wherein the radiation therapy is administered at a dose of about 1.8 to 2 Gy for 25 or more fractions.

* * * * *